(12) United States Patent
Fischer et al.

(10) Patent No.: US 10,611,779 B2
(45) Date of Patent: Apr. 7, 2020

(54) FUSED BICYCLIC HETEROCYCLE DERIVATIVES AS PESTICIDES

(71) Applicants: Bayer CropScience Aktiengesellschaft, Monheim am Rhein (DE); Bayer Aktiengesellschaft, Leverkusen (DE)

(72) Inventors: Ruediger Fischer, Pulheim (DE); Dominik Hager, Monheim (DE); Laura Hoffmeister, Duesseldorf (DE); Nina Kausch-Busies, Bergisch Gladbach (DE); Marc Mosrin, Cologne (DE); David Wilcke, Duesseldorf (DE); Matthieu Willot, Duesseldorf (DE); Kerstin Ilg, Cologne (DE); Ulrich Goergens, Ratingen (DE); Andreas Turberg, Haan (DE)

(73) Assignees: Bayer CropScience Aktiengesellschaft, Monheim am Rhein (DE); Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 16/333,385

(22) PCT Filed: Sep. 15, 2017

(86) PCT No.: PCT/EP2017/073290
§ 371 (c)(1),
(2) Date: Mar. 14, 2019

(87) PCT Pub. No.: WO2018/050825
PCT Pub. Date: Mar. 22, 2018

(65) Prior Publication Data
US 2019/0248811 A1    Aug. 15, 2019

(30) Foreign Application Priority Data
Sep. 19, 2016 (EP) .................................. 16189445

(51) Int. Cl.
*A01N 43/90* (2006.01)
*C07D 519/00* (2006.01)

(52) U.S. Cl.
CPC ........... *C07D 519/00* (2013.01); *A01N 43/90* (2013.01)

(58) Field of Classification Search
CPC ..... C07D 519/00; C07D 487/04; A01N 43/90
See application file for complete search history.

(56) References Cited

U.S. PATENT DOCUMENTS

| 8,552,017 | B2* | 10/2013 | Ivashchenko | ........ | C07D 471/14 514/267 |
| 8,569,318 | B2* | 10/2013 | Ivashchenko | ........ | C07D 471/14 514/267 |
| 9,271,500 | B2 | 3/2016 | Takahashi et al. | | |
| 9,936,703 | B2 | 4/2018 | Yonemura et al. | | |
| 10,087,192 | B2 | 10/2018 | Fischer et al. | | |
| 10,188,108 | B2 | 1/2019 | Fischer et al. | | |
| 2013/0079350 | A1* | 3/2013 | Ivashchenko | ....... | C07D 487/04 514/252.16 |
| 2014/0364444 | A1 | 12/2014 | Takyo et al. | | |
| 2017/0073342 | A1 | 3/2017 | Fischer et al. | | |
| 2017/0088548 | A1* | 3/2017 | Mueller | ............... | C07D 471/04 |
| 2017/0265474 | A1* | 9/2017 | Arlt | ....................... | C07D 513/04 |
| 2017/0325458 | A1* | 11/2017 | Jeschke | .................. | A01N 43/36 |
| 2017/0325459 | A1* | 11/2017 | Bretschneider | ....... | C07D 417/04 |
| 2018/0016273 | A1 | 1/2018 | Fischer et al. | | |
| 2018/0022760 | A1 | 1/2018 | Kudo et al. | | |
| 2018/0282319 | A1* | 10/2018 | Jeschke | ................ | C07D 471/04 |
| 2018/0282347 | A1* | 10/2018 | Arlt | ...................... | C07D 498/04 |
| 2019/0062344 | A1* | 2/2019 | Kudo | .................... | C07D 487/04 |
| 2019/0239510 | A1* | 8/2019 | Willot | .................. | C07D 519/00 |
| 2019/0274306 | A1* | 9/2019 | Kausch-Busies | .... | C07D 471/04 |
| 2019/0313643 | A1* | 10/2019 | Hoffmeister | ........... | A01N 47/02 |

FOREIGN PATENT DOCUMENTS

| EP | 3241830 A1 | 11/2017 |
| EP | 3305786 A2 | 4/2018 |
| JP | 2016-047064 | * 3/2016 |
| JP | 2016-054191 | * 5/2016 |
| JP | 2016-199515 | * 10/2016 |
| JP | 2016-255131 | * 12/2016 |
| WO | 2010/125985 A1 | 11/2010 |

(Continued)

OTHER PUBLICATIONS

CAS Abstract of US 20190062344 (2019) (Year: 2019).*

(Continued)

*Primary Examiner* — Alexander R Pagano
(74) *Attorney, Agent, or Firm* — McBee Moore & Vanik IP, LLC

(57) ABSTRACT

The invention relates to novel compounds of the formula (I)

(I)

in which Q, Aa, Ab, Ac, Ad, $R^1$ and n have the definitions given above, to their use as acaricides and/or insecticides for controlling animal pests and to processes and intermediates for their preparation.

14 Claims, No Drawings

(56) References Cited

FOREIGN PATENT DOCUMENTS

| | | |
|---|---|---|
| WO | 2012/074135 A1 | 6/2012 |
| WO | 2012/086848 A1 | 6/2012 |
| WO | 2013/018928 A1 | 2/2013 |
| WO | 2014/148451 A1 | 9/2014 |
| WO | 2015/000715 A1 | 1/2015 |
| WO | 2015/071180 A1 | 5/2015 |
| WO | 2015/121136 A1 | 8/2015 |
| WO | 2013/191113 A1 | 5/2016 |
| WO | 2016/091731 A1 | 6/2016 |
| WO | 2016/107742 A1 | 7/2016 |
| WO | 2016/124557 A1 | 8/2016 |
| WO | 2016/124563 A1 | 8/2016 |
| WO | 2016/162318 A1 | 10/2016 |
| WO | 2014/142292 A1 | 2/2017 |
| WO | 2017093180 A1 | 6/2017 |
| WO | 2017/125340 A1 | 7/2017 |
| WO | 2017144341 A1 | 8/2017 |
| WO | 2016/129684 A1 | 11/2017 |
| WO | 2018015289 A1 | 1/2018 |
| WO | 2018033455 A1 | 2/2018 |
| WO | 2018/095953 A1 | 5/2018 |
| WO | 2017155103 A1 | 1/2019 |

OTHER PUBLICATIONS

Machine Translation of JP 2016-255131 (Dec. 28, 2016) (Year: 2016).*

Machine Translation of JP 2016-054191 (May 17, 2016) (Year: 2016).*

Machine Translation of JP 2016-199515 (Oct. 7, 2016) (Year: 2016).*

Machine Translation of JP 2016-047064 (Mar. 10, 2016) (Year: 2016).*

PCT International Search Report for PCT/EP2017/070224, dated Nov. 15, 2017.

* cited by examiner

1

FUSED BICYCLIC HETEROCYCLE DERIVATIVES AS PESTICIDES

CROSS-REFERENCE TO RELATED APPLICATIONS

This application is a National Stage entry of International Application No. PCT/EP2017/073290, filed Sep. 15, 2017, which claims priority to European Patent Application No. 16189445.6, filed Sep. 19, 2016.

BACKGROUND

Field

The present invention relates to novel fused bicyclic heterocycle derivatives of the formula (I), to their use as acaricides and/or insecticides for controlling animal pests, particularly arthropods and especially insects and arachnids, and to processes and intermediates for their preparation.

Description of Related Art

Fused bicyclic heterocycle derivatives having insecticidal properties have already been described in the literature, for example in WO 2010/125985, WO 2012/074135, WO 2012/086848, WO 2013/018928, WO 2013/191113, WO 2014/142292, WO 2014/148451, WO 2015/000715, WO 2016/124563, WO 2016/124557, WO 2016/162318, WO 2017/093180, EP 16152384.0, EP 16156911.6, EP16168252.1, WO 2015/121136, WO2016/107742, WO2016/091731, WO 2016/129684, EP 16180168.3, EP 16180170.9, EP 16184163.0, EP 16200177.0.

However, some of the active ingredients already known from the documents cited above have disadvantages in use, whether in that they have only a narrow spectrum of application or in that they do not have satisfactory insecticidal or acaricidal activity.

SUMMARY

Novel fused bicyclic heterocycle derivatives have now been found, these having advantages over the compounds already known, examples of which include better biological or environmental properties, a wider range of application methods, better insecticidal or acaricidal action, and good compatibility with crop plants. The fused bicyclic heterocycle derivatives can be used in combination with further agents for improving efficacy, especially against insects that are difficult to control.

The present invention therefore provides novel compounds of the formula (I)

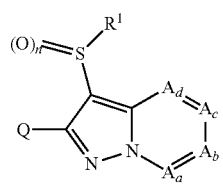

(I)

in which (configuration 1)
Aa is nitrogen or =C($R^{10}$)—,
Ab is nitrogen or =C($R^{11}$)—,
Ac is nitrogen or =C($R^{12}$)—,
Ad is nitrogen or =C($R^{13}$)—,
where not more than two of Aa, Ab, Ac and Ad can be nitrogens,
$R^1$ is ($C_1$-$C_6$)-alkyl, ($C_1$-$C_6$)-haloalkyl, ($C_1$-$C_6$)-cyanoalkyl, ($C_1$-$C_6$)-hydroxyalkyl, ($C_1$-$C_6$)-alkoxy-($C_1$-$C_6$)-alkyl, ($C_1$-$C_6$)-haloalkoxy-($C_1$-$C_6$)-alkyl, ($C_2$-$C_6$)-alkenyl, ($C_2$-$C_6$)-alkenyloxy-($C_1$-$C_6$)-alkyl, ($C_2$-$C_6$)-haloalkenyloxy-($C_1$-$C_6$)-alkyl, ($C_2$-$C_6$)-haloalkenyl, ($C_2$-$C_6$)-cyanoalkenyl, ($C_2$-$C_6$)-alkynyl, ($C_2$-$C_6$)-alkynyloxy-($C_1$-$C_6$)-alkyl, ($C_2$-$C_6$)-haloalkynyloxy-($C_1$-$C_6$)-alkyl, ($C_2$-$C_6$)-haloalkynyl, ($C_2$-$C_6$)-cyanoalkynyl, ($C_3$-$C_8$)-cycloalkyl, ($C_3$-$C_8$)-cycloalkyl-($C_3$-$C_8$)-cycloalkyl, ($C_1$-$C_6$)-alkyl-($C_3$-$C_8$)-cycloalkyl, halo-($C_3$-$C_8$)-cycloalkyl, amino, ($C_1$-$C_6$)-alkylamino, di-($C_1$-$C_6$)-alkyl-amino, ($C_3$-$C_8$)-cycloalkylamino, ($C_1$-$C_6$)-alkylcarbonylamino, ($C_1$-$C_6$)-alkylthio-($C_1$-$C_6$)-alkyl, ($C_1$-$C_6$)-haloalkylthio-($C_1$-$C_6$)-alkyl, ($C_1$-$C_6$)-alkylsulfinyl-($C_1$-$C_6$)-alkyl, ($C_1$-$C_6$)-haloalkylsulfinyl-($C_1$-$C_6$)-alkyl, ($C_1$-$C_6$)-alkylsulfonyl-($C_1$-$C_6$)-alkyl, ($C_1$-$C_6$)-haloalkylsulfonyl-($C_1$-$C_6$)-alkyl, ($C_1$-$C_6$)-alkoxy-($C_1$-$C_6$)-alkylthio-($C_1$-$C_6$)-alkyl, ($C_1$-$C_6$)-alkoxy-($C_1$-$C_6$)-alkylsulfinyl-($C_1$-$C_6$)-alkyl, ($C_1$-$C_6$)-alkoxy-($C_1$-$C_6$)-alkylsulfonyl-($C_1$-$C_6$)-alkyl, ($C_1$-$C_6$)-alkylcarbonyl-($C_1$-$C_6$)-alkyl, ($C_1$-$C_6$)-haloalkylcarbonyl-($C_1$-$C_6$)-alkyl, ($C_1$-$C_6$)-alkoxycarbonyl-($C_1$-$C_6$)-alkyl, ($C_1$-$C_6$)-haloalkoxycarbonyl-($C_1$-$C_6$)-alkyl, ($C_1$-$C_6$)-alkylsulfonylamino, aminosulfonyl-($C_1$-$C_6$)-alkyl, ($C_1$-$C_6$)-alkylaminosulfonyl-($C_1$-$C_6$)-alkyl, di-($C_1$-$C_6$)-alkylaminosulfonyl-($C_1$-$C_6$)-alkyl,
or is in each case optionally identically or differently mono- or poly-aryl-, -hetaryl- or -heterocyclyl-substituted ($C_1$-$C_6$)-alkyl, ($C_1$-$C_6$)-alkoxy, ($C_2$-$C_6$)-alkenyl, ($C_2$-$C_6$)-alkynyl, ($C_3$-$C_8$)-cycloalkyl, where aryl, hetaryl or heterocyclyl may each optionally be mono- or polysubstituted identically or differently by halogen, cyano, nitro, hydroxyl, amino, carboxyl, carbamoyl, aminosulfonyl, ($C_1$-$C_6$)-alkyl, ($C_3$-$C_6$)-cycloalkyl, ($C_1$-$C_6$)-alkoxy, ($C_1$-$C_6$)-haloalkyl, ($C_1$-$C_6$)-haloalkoxy, ($C_1$-$C_6$)-alkylthio, ($C_1$-$C_6$)-alkylsulfinyl, ($C_3$-$C_6$)-alkylsulfonyl, ($C_1$-$C_6$)-alkylsulfimino, ($C_1$-$C_6$)-alkylsulfimino-($C_1$-$C_6$)-alkyl, ($C_1$-$C_6$)-alkylsulfimino-($C_2$-$C_6$)-alkylcarbonyl, ($C_1$-$C_6$)-alkylsulfoximino, ($C_1$-$C_6$)-alkylsulfoximino-($C_1$-$C_6$)-alkyl, ($C_1$-$C_6$)-alkylsulfoximino-($C_2$-$C_6$)-alkylcarbonyl, ($C_1$-$C_6$)-alkoxycarbonyl, ($C_1$-$C_6$)-alkylcarbonyl, ($C_3$-$C_6$)-trialkylsilyl or benzyl, or
$R^1$ is aryl, hetaryl or heterocyclyl, each of which is optionally mono- or polysubstituted identically or differently by halogen, cyano, nitro, hydroxyl, amino, carboxyl, carbamoyl, ($C_1$-$C_6$)-alkyl, ($C_3$-$C_8$)-cycloalkyl, ($C_1$-$C_6$)-alkoxy, ($C_1$-$C_6$)-haloalkyl, ($C_1$-$C_6$)-haloalkoxy, ($C_1$-$C_6$)-alkylthio, ($C_1$-$C_6$)-alkylsulfinyl, ($C_1$-$C_6$)-alkylsulfonyl, ($C_1$-$C_6$)-alkylsulfimino, ($C_1$-$C_6$)-alkylsulfimino-($C_1$-$C_6$)-alkyl, ($C_1$-$C_6$)-alkylsulfimino-($C_2$-$C_6$)-alkylcarbonyl, ($C_1$-$C_6$)-alkylsulfoximino, ($C_1$-$C_6$)-alkylsulfoximino-($C_1$-$C_6$)-alkyl, ($C_1$-$C_6$)-alkylsulfoximino-($C_2$—C)-alkylcarbonyl, ($C_1$-$C_6$)-alkoxycarbonyl, ($C_1$-$C_6$)-alkylcarbonyl, ($C_3$-$C_8$)-trialkylsilyl, (=O) (in the case of heterocyclyl only) or (=O)$_2$ (in the case of heterocyclyl only),
$R^{10}$, $R^{11}$, $R^{12}$, $R^{13}$ are independently hydrogen, cyano, halogen, nitro, acetyl, hydroxyl, amino, SCN, tri-($C_1$-$C_6$)-alkylsilyl, ($C_3$-$C_8$)-cycloalkyl, ($C_3$-$C_8$)-cycloalkyl-($C_3$-$C_8$)-cycloalkyl, ($C_1$-$C_6$)-alkyl-($C_3$-$C_8$)-cycloalkyl, halo-($C_3$-$C_8$)-cycloalkyl, ($C_1$-$C_6$)-alkyl, ($C_1$-$C_6$)-haloalkyl, ($C_1$-$C_6$)-cyanoalkyl, ($C_1$-$C_6$)-hydroxyalkyl, hydroxycarbonyl-($C_1$-$C_6$)-alkoxy, ($C_1$-$C_6$)-alkoxycarbonyl-($C_1$-$C_6$)-alkyl, ($C_1$-$C_6$)-alkoxy-($C_1$-$C_6$)-alkyl, ($C_2$-$C_6$)-alkenyl, $(C_2-C_6)$-haloalkenyl, $(C_2-C_6)$-cyanoalkenyl, $(C_2-C_6)$-alkynyl, $(C_2-C_6)$-haloalkynyl, $(C_2-C_6)$-cyanoalkynyl, $(C_1-C_6)$-alkoxy, $(C_1-C_6)$-haloalkoxy, $(C_1-C_6)$-cyanoalkoxy, $(C_1-C_6)$-alkoxycarbonyl-$(C_1-C_6)$-alkoxy, $(C_1-C_6)$-alkoxy-$(C_1-C_6)$-alkoxy, $(C_1-C_6)$-alkylhydroxyimino, $(C_1-C_6)$-alkoxyimino, $(C_1-C_6)$-alkyl-$(C_1-C_6)$-alkoxyimino, $(C_1-C_6)$-haloalkyl-$(C_1-C_6)$-alkoxyimino, $(C_1-C_6)$-alkylthio, $(C_1-C_6)$-haloalkylthio, $(C_1-C_6)$-alkoxy-$(C_1-C_6)$-alkylthio, $(C_1-C_6)$-alkylthio-$(C_1-C_6)$-alkyl, $(C_1-C_6)$-alkylsulfinyl, $(C_1-C_6)$-haloalkylsulfinyl, $(C_1-C_6)$-alkoxy-$(C_1-C_6)$-alkylsulfinyl, $(C_1-C_6)$-alkylsulfinyl-$(C_1-C_6)$-alkyl, $(C_1-C_6)$-alkylsulfonyl, $(C_1-C_6)$-haloalkylsulfonyl, $(C_1-C_6)$-alkoxy-$(C_1-C_6)$-alkylsulfonyl, $(C_1-C_6)$-alkylsulfonyl-$(C_1-C_6)$-alkyl, $(C_1-C_6)$-alkylsulfonyloxy, $(C_1-C_6)$-alkylcarbonyl, $(C_1-C_6)$-alkylthiocarbonyl, $(C_1-C_6)$-haloalkylcarbonyl, $(C_1-C_6)$-alkylcarbonyloxy, $(C_1-C_6)$-alkoxycarbonyl, $(C_1-C_6)$-haloalkoxy carbonyl, aminocarbonyl, $(C_1-C_6)$-alkylaminocarbonyl, $(C_1-C_6)$-alkylaminothiocarbonyl, di-$(C_1-C_6)$-alkylaminocarbonyl, di-$(C_1-C_6)$-alkylaminothiocarbonyl, $(C_2-C_6)$-alkenylaminocarbonyl, di-$(C_2-C_6)$-alkenylaminocarbonyl, $(C_3-C_8)$-cycloalkylaminocarbonyl, $(C_1-C_6)$-alkylsulfonylamino, $(C_1-C_6)$-alkylamino, di-$(C_1-C_6)$-alkylamino, aminosulfonyl, $(C_1-C_6)$-alkylaminosulfonyl, di-$(C_1-C_6)$-alkylaminosulfonyl, $(C_1-C_6)$-alkylsulfoximino, aminothiocarbonyl, $(C_1-C_6)$-alkylaminothiocarbonyl, di-$(C_1-C_6)$-alkylaminothiocarbonyl, $(C_3-C_8)$-cycloalkylamino, NHCO—$(C_1-C_6)$-alkyl ($(C_1-C_6)$-alkylcarbonylamino), or are in each case optionally singly or multiply, identically or differently substituted aryl or hetaryl, where (in the case of hetaryl) at least one carbonyl group may optionally be present and/or where possible substituents in each case are as follows: cyano, carboxyl, halogen, nitro, acetyl, hydroxyl, amino, SCN, tri-$(C_1-C_6)$alkylsilyl, $(C_3-C_8)$cycloalkyl, $(C_3-C_8)$cycloalkyl-$(C_3-C_8)$cycloalkyl, $(C_1-C_6)$alkyl-$(C_3-C_8)$cycloalkyl, halo$(C_3-C_8)$cycloalkyl, $(C_1-C_6)$alkyl, $(C_1-C_6)$haloalkyl, $(C_1-C_6)$cyanoalkyl, $(C_1-C_6)$hydroxyalkyl, hydroxycarbonyl-$(C_1-C_6)$-alkoxy, $(C_1-C_6)$alkoxycarbonyl-$(C_1-C_6)$alkyl, $(C_1-C_6)$alkoxy-$(C_1-C_6)$alkyl, $(C_2-C_6)$alkenyl, $(C_2-C_6)$haloalkenyl, $(C_2-C_6)$cyanoalkenyl, $(C_2-C_6)$alkynyl, $(C_2-C_6)$haloalkynyl, $(C_2-C_6)$cyanoalkynyl, $(C_1-C_6)$alkoxy, $(C_1-C_6)$haloalkoxy, $(C_1-C_6)$cyanoalkoxy, $(C_1-C_6)$alkoxycarbonyl-$(C_1-C_6)$alkoxy, $(C_1-C_6)$alkoxy-$(C_1-C_6)$alkoxy, $(C_1-C_6)$alkylhydroxyimino, $(C_1-C_6)$alkoxyimino, $(C_1-C_6)$alkyl-$(C_1-C_6)$alkoxyimino, $(C_1-C_6)$haloalkyl-$(C_1-C_6)$alkoxyimino, $(C_1-C_6)$alkylthio, $(C_1-C_6)$haloalkylthio, $(C_1-C_6)$alkoxy-$(C_1-C_6)$alkylthio, $(C_1-C_6)$alkylthio-$(C_1-C_6)$alkyl, $(C_1-C_6)$alkylsulfinyl, $(C_1-C_6)$haloalkylsulfinyl, $(C_1-C_6)$alkoxy-$(C_1-C_6)$alkylsulfinyl, $(C_1-C_6)$alkylsulfinyl-$(C_1-C_6)$alkyl, $(C_1-C_6)$alkylsulfonyl, $(C_1-C_6)$haloalkylsulfonyl, $(C_1-C_6)$alkoxy-$(C_1-C_6)$alkylsulfonyl, $(C_1-C_6)$alkylsulfonyl-$(C_1-C_6)$alkyl, $(C_1-C_6)$alkylsulfonyloxy, $(C_1-C_6)$alkylcarbonyl, $(C_1-C_6)$haloalkylcarbonyl, $(C_1-C_6)$alkylcarbonyloxy, $(C_1-C_6)$alkoxycarbonyl, $(C_1-C_6)$haloalkoxycarbonyl, aminocarbonyl, $(C_1-C_6)$alkylaminocarbonyl, di-$(C_1-C_6)$alkylaminocarbonyl, $(C_2-C_6)$alkenylaminocarbonyl, di-$(C_2-C_6)$-alkenylaminocarbonyl, $(C_3-C_8)$cycloalkylaminocarbonyl, $(C_1-C_6)$alkylsulfonylamino, $(C_1-C_6)$alkylamino, di-$(C_1-C_6)$alkylamino, aminosulfonyl, $(C_1-C_6)$alkylaminosulfonyl, di-$(C_1-C_6)$alkylaminosulfonyl, $(C_1-C_6)$alkylsulfoximino, aminothiocarbonyl, $(C_1-C_6)$alkylaminothiocarbonyl, di-$(C_1-C_6)$alkylaminothiocarbonyl, $(C_3-C_8)$cycloalkylamino, $(C_1-C_6)$alkylcarbonylamino, where only one or two of the $R^{10}$, $R^{11}$, $R^{12}$, $R^{13}$ radicals is/are a substituent other than hydrogen, Q is a partly saturated or saturated heterocyclic or heteroaromatic 8-, 9-, 10-, 11- or 12-membered fused bicyclic or tricyclic ring system where at least one carbonyl group may optionally be present and/or where the ring system is optionally mono- or polysubstituted identically or differently, and where the substituents may independently be selected from cyano, halogen, nitro, acetyl, hydroxyl, amino, SCN, tri-$(C_1-C_6)$-alkylsilyl, $(C_3-C_8)$-cycloalkyl, $(C_3-C_8)$-cycloalkyl-$(C_3-C_8)$-cycloalkyl, $(C_1-C_6)$-alkyl-$(C_3-C_8)$-cycloalkyl, halo-$(C_3-C_8)$-cycloalkyl, $(C_3-C_6)$-alkyl, $(C_1-C_6)$-haloalkyl, $(C_3-C_8)$-cyanoalkyl, $(C_1-C_6)$-hydroxyalkyl, hydroxycarbonyl-$(C_3-C_6)$-alkoxy, $(C_1-C_6)$-alkoxycarbonyl-$(C_1-C_6)$-alkyl, $(C_1-C_6)$-alkoxy-$(C_1-C_6)$-alkyl, $(C_2-C_6)$-alkenyl, $(C_2-C_6)$-haloalkenyl, $(C_2-C_6)$-cyanoalkenyl, $(C_2-C_6)$-alkynyl, $(C_2-C_6)$-alkynyloxy-$(C_1-C_4)$-alkyl, $(C_2-C_6)$-haloalkynyl, $(C_2-C_6)$-cyanoalkynyl, $(C_1-C_6)$-alkoxy, $(C_1-C_6)$-haloalkoxy, $(C_1-C_6)$-haloalkoxy-$(C_1-C_6)$-alkyl, $(C_2-C_6)$-alkenyloxy-$(C_1-C_6)$-alkyl, $(C_2-C_6)$-haloalkenyloxy-$(C_1-C_6)$-alkyl, $(C_1-C_6)$-cyanoalkoxy, $(C_1-C_6)$-alkoxycarbonyl-$(C_1-C_6)$-alkoxy, $(C_1-C_6)$-alkoxy-$(C_1-C_6)$-alkoxy, $(C_1-C_6)$-alkylhydroxyimino, $(C_1-C_6)$-alkoxyimino, $(C_1-C_6)$-alkyl-$(C_1-C_6)$-alkoxyimino, $(C_1-C_6)$-haloalkyl-$(C_1-C_6)$-alkoxyimino, $(C_1-C_6)$-alkylthio, $(C_1-C_6)$-haloalkylthio, $(C_1-C_6)$-alkoxy-$(C_1-C_6)$-alkylthio, $(C_1-C_6)$-alkylthio-$(C_1-C_6)$-alkyl, $(C_4-C_6)$-alkylsulfinyl, $(C_1-C_6)$-haloalkylsulfinyl, $(C_1-C_6)$-alkoxy-$(C_1-C_6)$-alkylsulfinyl, $(C_1-C_6)$-alkylsulfinyl-$(C_1-C_6)$-alkyl, $(C_1-C_6)$-alkylsulfonyl, $(C_1-C_6)$-haloalkylsulfonyl, $(C_1-C_6)$-alkoxy-$(C_1-C_6)$-alkylsulfonyl, $(C_1-C_6)$-alkylsulfonyl-$(C_1-C_6)$-alkyl, $(C_1-C_6)$-alkylsulfonyloxy, $(C_1-C_6)$-alkylcarbonyl, $(C_1-C_6)$-alkylcarbonyl-$(C_1-C_6)$-alkyl, $(C_1-C_6)$-alkylthiocarbonyl, $(C_1-C_6)$-haloalkylcarbonyl, $(C_1-C_6)$-alkylcarbonyloxy, $(C_1-C_6)$-alkoxycarbonyl, $(C_1-C_6)$-haloalkoxycarbonyl, aminocarbonyl, $(C_1-C_6)$-alkylaminocarbonyl, $(C_1-C_6)$-alkylaminothiocarbonyl, di-$(C_1-C_6)$-alkyl-aminocarbonyl, di-$(C_1-C_6)$-alkyl-aminothiocarbonyl, $(C_2-C_6)$-alkenylaminocarbonyl, di-$(C_2-C_6)$-alkenylaminocarbonyl, $(C_3-C_8)$-cycloalkylaminocarbonyl, $(C_1-C_6)$-alkylsulfonylamino, $(C_1-C_6)$-alkylamino, di-$(C_1-C_6)$-alkylamino, aminosulfonyl, $(C_1-C_6)$-alkylaminosulfonyl, di-$(C_1-C_6)$-alkylaminosulfonyl, $(C_1-C_6)$-alkylsulfoximino, aminothiocarbonyl, $(C_1-C_6)$-alkylaminothiocarbonyl, di-$(C_1-C_6)$-alkyl-aminothiocarbonyl, $(C_3-C_8)$-cycloalkylamino, NHCO—$(C_1-C_6)$-alkyl ($(C_1-C_6)$-alkylcarbonylamino), or where the substituents may independently be selected from phenyl or a 5- or 6-membered heteroaromatic ring, where phenyl or the ring may optionally be mono- or polysubstituted identically or differently by $C_1-C_6$-alkyl, $C_2-C_6$-alkenyl, $C_2-C_6$-alkynyl, $C_3-C_6$-cycloalkyl, $C_1-C_6$-haloalkyl, $C_1-C_6$-haloalkenyl, $C_2-C_6$-haloalkynyl, $C_3-C_6$-halocycloalkyl, halogen, CN, $NO_2$, $C_3-C_4$-alkoxy, $C_1-C_4$-haloalkoxy, n is 0, 1 or 2.

It has additionally been found that the compounds of the formula (I) have very good efficacy as pesticides, preferably as insecticides and/or acaricides, and additionally generally have very good plant compatibility, in particular with respect to crop plants.

DETAILED DESCRIPTION OF A PREFERRED EMBODIMENT

The compounds according to the invention are defined in general terms by the formula (I). Preferred substituents or ranges of the radicals given in the formulae mentioned above and below are illustrated hereinafter:

Configuration 2

Aa is preferably nitrogen or =C($R^{10}$)—,
Ab is preferably nitrogen or =C($R^{11}$)—,
Ac is preferably nitrogen or =C($R^{12}$)—,
Ad is preferably nitrogen or =C($R^{13}$)—,
where not more than two of Aa, Ab, Ac and Ad can be nitrogens, $R^1$ is preferably ($C_1$-$C_4$)alkyl, ($C_1$-$C_4$)hydroxyalkyl, ($C_1$-$C_4$)haloalkyl, ($C_1$-$C_4$)cyanoalkyl, ($C_1$-$C_4$)alkoxy-($C_1$-$C_4$)alkyl, ($C_1$-$C_4$)haloalkoxy-($C_1$-$C_4$)alkyl, ($C_2$-$C_4$)alkenyl, ($C_2$-$C_4$)alkenyloxy-($C_1$-$C_4$)alkyl, ($C_2$-$C_4$)haloalkenyloxy-($C_1$-$C_4$)alkyl, ($C_2$-$C_4$)haloalkenyl, ($C_2$-$C_4$)cyanoalkenyl, ($C_2$-$C_4$)alkynyl, ($C_2$-$C_4$)alkynyloxy-($C_1$-$C_4$)alkyl, ($C_2$-$C_4$)haloalkynyloxy-($C_1$-$C_4$)alkyl, ($C_2$-$C_4$)haloalkynyl, ($C_2$-$C_4$)cyanoalkynyl, ($C_3$-$C_6$)cycloalkyl, ($C_3$-$C_6$)cycloalkyl($C_3$-$C_6$)cycloalkyl, ($C_1$-$C_4$)alkyl-($C_3$-$C_6$)cycloalkyl, halo($C_3$-$C_6$)cycloalkyl, ($C_1$-$C_4$)alkylamino, di-($C_1$-$C_4$)alkyl-amino, ($C_3$-$C_6$)cycloalkylamino, ($C_1$-$C_4$)alkylcarbonylamino, ($C_1$-$C_4$)alkylthio-($C_1$-$C_4$)alkyl, ($C_1$-$C_4$)haloalkylthio-($C_1$-$C_4$)alkyl, ($C_1$-$C_4$)alkylsulfinyl-($C_1$-$C_4$)alkyl, ($C_1$-$C_4$)haloalkylsulfinyl-($C_1$-$C_4$)alkyl, ($C_1$-$C_4$)alkylsulfonyl-($C_1$-$C_4$)alkyl, ($C_1$-$C_4$)alkylcarbonyl-($C_1$-$C_4$)alkyl, ($C_1$-$C_4$)haloalkylcarbonyl-($C_1$-$C_4$)alkyl, ($C_1$-$C_4$)alkylsulfonylamino, or is in each case optionally identically or differently mono- or di-aryl-, -hetaryl- or -heterocyclyl-substituted ($C_1$-$C_4$)alkyl, ($C_1$-$C_4$)alkoxy, ($C_2$-$C_4$)alkenyl, ($C_2$-$C_4$)alkynyl, ($C_3$-$C_6$)cycloalkyl, where aryl, hetaryl or heterocyclyl may each optionally identically or differently be mono- or disubstituted by halogen, cyano, carbamoyl, aminosulfonyl, ($C_1$-$C_4$)alkyl, ($C_3$-$C_4$)cycloalkyl, ($C_1$-$C_4$)alkoxy, ($C_1$-$C_4$)haloalkyl, ($C_1$-$C_4$)haloalkoxy, ($C_1$-$C_4$)alkylthio, ($C_1$-$C_4$)alkylsulfinyl, ($C_1$-$C_4$)alkylsulfonyl, ($C_1$-$C_4$)alkylsulfimino, or $R^1$ is preferably aryl, hetaryl or heterocyclyl, each of which is optionally mono- or disubstituted identically or differently by halogen, cyano, carbamoyl, ($C_1$-$C_4$)-alkyl, ($C_3$-$C_6$)-cycloalkyl, ($C_1$-$C_4$)-alkoxy, ($C_1$-$C_4$)-haloalkyl, ($C_1$-$C_4$)-haloalkoxy, ($C_1$-$C_4$)-alkylthio, ($C_1$-$C_4$)-alkylsulfinyl, ($C_3$-$C_4$)-alkylsulfonyl, ($C_1$-$C_4$)-alkylsulfimino, ($C_1$-$C_4$)-alkylsulfoximino, ($C_1$-$C_4$)-alkylcarbonyl, ($C_3$-$C_4$)-trialkylsilyl, (=O) (in the case of heterocyclyl only) or (=O)$_2$ (in the case of heterocyclyl only), $R^{10}$, $R^{11}$, $R^{12}$, $R^{13}$, are preferably independently hydrogen, cyano, halogen, nitro, acetyl, hydroxyl, amino, SCN, tri-($C_1$-$C_4$)alkylsilyl, ($C_3$-$C_6$)cycloalkyl, ($C_3$-$C_6$)cycloalkyl-($C_3$-$C_6$)cycloalkyl, ($C_1$-$C_4$)alkyl-($C_3$-$C_6$)cycloalkyl, halo($C_3$-$C_6$)cycloalkyl, ($C_1$-$C_4$)alkyl, ($C_1$-$C_4$)haloalkyl, ($C_1$—C)cyanoalkyl, ($C_1$-$C_4$)hydroxyalkyl, ($C_1$-$C_4$)alkoxy-($C_1$-$C_4$)alkyl, ($C_2$-$C_4$)alkenyl, ($C_2$-$C_4$)haloalkenyl, ($C_2$-$C_4$)cyanoalkenyl, ($C_2$-$C_4$)alkynyl, ($C_2$-$C_4$)haloalkynyl, ($C_2$-$C_4$)cyanoalkynyl, ($C_1$-$C_4$)alkoxy, ($C_1$-$C_4$)haloalkoxy, ($C_1$-$C_4$)cyanoalkoxy, ($C_1$-$C_4$)alkoxy-($C_1$-$C_4$)alkoxy, ($C_1$-$C_4$)alkylhydroxyimino, ($C_1$-$C_4$)alkoxyimino, ($C_1$-$C_4$)alkyl-($C_1$-$C_4$)alkoxyimino, ($C_1$-$C_4$)haloalkyl-($C_1$-$C_4$)alkoxyimino, ($C_1$-$C_4$)alkylthio, ($C_1$-$C_4$)haloalkylthio, ($C_1$-$C_4$)alkylthio-($C_1$-$C_4$)alkyl, ($C_1$-$C_4$)alkylsulfinyl, ($C_1$-$C_4$)haloalkylsulfinyl, ($C_1$-$C_4$)alkylsulfinyl-($C_1$-$C_4$)alkyl, ($C_1$-$C_4$)alkylsulfonyl, ($C_1$-$C_4$)haloalkylsulfonyl, ($C_1$-$C_4$)alkylsulfonyl-($C_1$-$C_4$)alkyl, ($C_1$-$C_4$)alkylsulfonyloxy, ($C_1$-$C_4$)alkylcarbonyl, ($C_1$-$C_4$)haloalkylcarbonyl, aminocarbonyl, aminothiocarbonyl, ($C_1$-$C_4$)alkylaminocarbonyl, di-($C_1$-$C_4$)alkylaminocarbonyl, ($C_1$-$C_4$)alkylsulfonylamino, ($C_1$-$C_4$)alkylamino, di-($C_1$-$C_4$)alkylamino, aminosulfonyl, ($C_1$-$C_1$)alkylaminosulfonyl, di-($C_1$-$C_4$)alkylaminosulfonyl, aminothiocarbonyl, NHCO—($C_1$-$C_4$)alkyl (($C_1$-$C_4$)alkylcarbonylamino), and also preferably are phenyl or hetaryl, each of which is optionally mono- or disubstituted identically or differently, where (in the case of hetaryl) at least one carbonyl group may optionally be present and/or where possible substituents are in each case as follows: cyano, halogen, nitro, acetyl, amino, ($C_3$-$C_6$)cycloalkyl, ($C_3$-$C_6$)cycloalkyl-($C_3$-$C_6$)cycloalkyl, ($C_1$-$C_4$)alkyl-($C_3$-$C_6$)cycloalkyl, halo-($C_3$-$C_6$)cycloalkyl, ($C_1$-$C_4$)alkyl, ($C_1$-$C_4$)haloalkyl, ($C_1$-$C_4$)cyanoalkyl, ($C_1$-$C_4$)hydroxyalkyl, ($C_1$-$C_4$)alkoxy-($C_1$-$C_4$)alkyl, ($C_2$-$C_4$)alkenyl, ($C_2$-$C_4$)haloalkenyl, ($C_2$-$C_4$)cyanoalkenyl, ($C_2$-$C_4$)alkynyl, ($C_2$-$C_4$)haloalkynyl, ($C_2$-$C_4$)cyanoalkynyl, ($C_1$-$C_4$)alkoxy, ($C_1$-$C_4$)haloalkoxy, ($C_1$-$C_4$)cyanoalkoxy, ($C_1$-$C_4$)alkoxy-($C_1$-$C_4$)alkoxy, ($C_1$-$C_4$)alkylhydroxyimino, ($C_1$-$C_4$)alkoxyimino, ($C_1$-$C_4$)alkyl-($C_1$-$C_4$)alkoxyimino, ($C_1$-$C_4$)haloalkyl-($C_1$-$C_4$)alkoxyimino, ($C_1$-$C_4$)alkylthio, ($C_1$-$C_4$)haloalkylthio, ($C_1$-$C_4$)alkylthio-($C_1$-$C_4$)alkyl, ($C_1$-$C_4$)alkylsulfinyl, ($C_1$-$C_4$)haloalkylsulfinyl, ($C_1$-$C_4$)alkylsulfinyl-($C_1$-$C_4$)alkyl, ($C_1$-$C_4$)alkylsulfonyl, ($C_1$-$C_4$)haloalkylsulfonyl, ($C_1$-$C_4$)alkylsulfonyl-($C_1$-$C_4$)alkyl, ($C_1$-$C_4$)alkylsulfonyloxy, ($C_1$-$C_4$)alkylcarbonyl, ($C_1$-$C_4$)haloalkylcarbonyl, aminocarbonyl, ($C_1$-$C_4$)alkylaminocarbonyl, di-($C_1$-$C_4$)alkylaminocarbonyl, ($C_1$-$C_4$)alkylsulfonylamino, ($C_1$-$C_4$)alkylamino, di-($C_1$-$C_4$)alkylamino, aminosulfonyl, ($C_1$-$C_4$)alkylaminosulfonyl, di-($C_1$-$C_4$)alkylaminosulfonyl, NHCO—($C_1$-$C_4$)alkyl (($C_1$-$C_4$)alkylcarbonylamino), where only one or two of the $R^{10}$, $R^{11}$, $R^{12}$, $R^{13}$ radicals is/are a substituent other than hydrogen, Q is preferably a heteroaromatic 8-, 9-, 10-, 11- or 12-membered fused bicyclic or tricyclic ring system, where the ring system is optionally mono- or polysubstituted identically or differently and where the substituents may independently be selected from cyano, halogen, nitro, acetyl, hydroxyl, amino, SCN, tri-($C_1$-$C_6$)-alkylsilyl, ($C_3$-$C_8$)-cycloalkyl, ($C_3$-$C_8$)-cycloalkyl-($C_3$-$C_8$)-cycloalkyl, ($C_1$-$C_6$)-alkyl-($C_3$-$C_8$)-cycloalkyl, halo-($C_3$-$C_8$)-cycloalkyl, ($C_1$-$C_6$)-alkyl, ($C_1$-$C_6$)-haloalkyl, ($C_1$-$C_6$)-cyanoalkyl, ($C_1$-$C_6$)-hydroxyalkyl, ($C_1$-$C_6$)-alkoxy-($C_1$-$C_6$)-alkyl, ($C_2$-$C_6$)-alkenyl, ($C_2$-$C_6$)-haloalkenyl, ($C_2$-$C_6$)-cyanoalkenyl, ($C_2$-$C_6$)-alkynyl, ($C_2$-$C_6$)-alkynyloxy-($C_1$-$C_4$)-alkyl, ($C_2$-$C_6$)-haloalkynyl, ($C_1$-$C_6$)-alkoxy, ($C_1$-$C_6$)-haloalkoxy, ($C_1$-$C_6$)-haloalkoxy-($C_1$-$C_6$)-alkyl, ($C_2$-$C_6$)-alkenyloxy-($C_1$-$C_6$)-alkyl, ($C_2$-$C_6$)-haloalkenyloxy-($C_1$-$C_6$)-alkyl, ($C_1$-$C_6$)-cyanoalkoxy, ($C_1$-$C_6$)-alkoxy-($C_1$-$C_6$)-alkoxy, ($C_1$-$C_6$)-alkylhydroxyimino, ($C_1$-$C_6$)-alkoxyimino, ($C_1$-$C_6$)-alkyl-($C_1$-$C_6$)-alkoxyimino, ($C_1$-$C_6$)-alkylthio, ($C_1$-$C_6$)-haloalkylthio, ($C_1$-$C_6$)-alkoxy-($C_1$-$C_6$)-alkylthio, ($C_1$-$C_6$)-alkylthio-($C_1$-$C_6$)-alkyl, ($C_1$-$C_6$)-alkylsulfinyl, ($C_1$-$C_6$)-haloalkylsulfinyl, ($C_1$-$C_6$)-alkoxy-($C_1$-$C_6$)-alkylsulfinyl, ($C_1$-$C_6$)-alkylsulfinyl-($C_1$-$C_6$)-alkyl, ($C_1$-$C_6$)-alkyl sulfonyl, ($C_1$-$C_6$)-haloalkylsulfonyl, ($C_1$-$C_6$)-alkoxy-($C_1$-$C_6$)-alkylsulfonyl, ($C_1$-$C_6$)-alkylsulfonyl-($C_1$-$C_6$)-alkyl, ($C_1$-$C_6$)-alkylsulfonyloxy, ($C_1$-$C_6$)-alkylcarbonyl, ($C_1$-$C_6$)-alkylcarbonyl-($C_1$-$C_6$)-alkyl, ($C_1$-$C_6$)-alkylthiocarbonyl, ($C_1$-$C_6$)-haloalkylcarbonyl, ($C_1$-$C_6$)-alkylcarbonyloxy, ($C_1$-$C_6$)-alkoxycarbonyl, ($C_1$-$C_6$)-haloalkoxycarbonyl, aminocarbonyl, ($C_1$-$C_6$)-alkylaminocarbonyl, ($C_1$-$C_6$)-alkylaminothiocarbonyl, di-($C_1$-$C_6$)-alkylaminocarbonyl, di-($C_1$-$C_6$)-alkylaminothiocarbonyl, ($C_3$-$C_8$)-cycloalkylaminocarbonyl, ($C_1$-$C_6$)-alkylsulfonylamino, ($C_1$-$C_6$)-alkylamino, di-($C_1$-$C_6$)-alkylamino, aminosulfonyl, ($C_1$-

$C_6$)-alkylaminosulfonyl, di-($C_1$-$C_6$)-alkylaminosulfonyl, ($C_1$-$C_6$)-alkylsulfoximino, aminothiocarbonyl, ($C_1$-$C_6$)-alkylaminothiocarbonyl, di-($C_1$-$C_6$)-alkylaminothiocarbonyl, ($C_3$-$C_8$)-cycloalkylamino, NHCO—($C_1$-$C_6$)-alkyl (($C_1$-$C_6$)-alkylcarbonylamino), or where the substituents may independently be selected from phenyl or a 5- or 6-membered heteroaromatic ring, where phenyl or the ring may optionally be mono- or polysubstituted identically or differently by $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, $C_1$-$C_4$-alkoxy, $C_1$-$C_4$-haloalkoxy, n is preferably 0, 1 or 2.

Configuration 3

Aa is more preferably nitrogen or =C($R^{10}$)—,
Ab is more preferably nitrogen or =C($R^{11}$)—,
Ac is more preferably nitrogen or =C($R^{12}$)—,
Ad is more preferably nitrogen or =C($R^{13}$)—,
where not more than two of Aa, Ab, Ac and Ad can be nitrogens, $R^1$ is more preferably ($C_1$-$C_4$)alkyl, ($C_1$-$C_4$)hydroxyalkyl, ($C_1$-$C_4$)haloalkyl, ($C_2$-$C_4$)alkenyl, ($C_2$-$C_4$)haloalkenyl, ($C_2$-$C_4$)alkynyl, ($C_2$-$C_4$)haloalkynyl, ($C_3$-$C_6$)cycloalkyl, ($C_1$-$C_4$)alkylthio-($C_1$-$C_4$)alkyl, ($C_1$-$C_4$)alkylsulfinyl-($C_1$-$C_4$)alkyl or ($C_1$-$C_4$)alkylsulfonyl-($C_1$-$C_4$)alkyl, $R^{10}$, $R^{11}$, $R^{12}$, $R^{13}$, are more preferably independently hydrogen, cyano, halogen, nitro, hydroxyl, amino, SCN, tri-($C_1$-$C_4$)alkylsilyl, ($C_3$-$C_6$)cycloalkyl, ($C_3$-$C_6$)cycloalkyl-($C_3$-$C_6$)cycloalkyl, ($C_1$-$C_4$)alkyl-($C_3$-$C_6$)cycloalkyl, halo($C_3$-$C_6$)cycloalkyl, ($C_1$-$C_4$)alkyl, ($C_1$-$C_4$)haloalkyl, ($C_1$-$C_4$)cyanoalkyl, ($C_1$-$C_4$)alkoxy-($C_1$-$C_4$)alkyl, ($C_2$-$C_4$)alkenyl, ($C_2$-$C_4$)haloalkenyl, ($C_2$-$C_4$)cyanoalkenyl, ($C_2$-$C_4$)alkynyl, ($C_2$-$C_4$)haloalkynyl, ($C_2$-$C_4$)cyanoalkynyl, ($C_1$-$C_4$)alkoxy, ($C_1$-$C_4$)haloalkoxy, ($C_1$-$C_4$)cyanoalkoxy, ($C_1$-$C_1$)alkylhydroxyimino, ($C_1$-$C_4$)alkoxyimino, ($C_1$-$C_4$)alkyl-($C_1$-$C_4$)alkoxyimino, ($C_1$-$C_4$)alkylthio, ($C_1$-$C_4$)haloalkylthio, ($C_1$-$C_4$)alkylsulfinyl, ($C_1$-$C_4$)haloalkylsulfinyl, ($C_1$-$C_4$)alkylsulfonyl, ($C_1$-$C_4$)haloalkylsulfonyl, ($C_1$-$C_4$)alkylsulfonyloxy, ($C_1$-$C_4$)alkylcarbonyl, ($C_1$-$C_4$)haloalkylcarbonyl, aminocarbonyl, ($C_4$-$C_4$)alkylaminocarbonyl, di-($C_1$-$C_4$)alkylaminocarbonyl, ($C_1$-$C_4$)alkylsulfonylamino, ($C_1$-$C_4$)alkylamino, di-($C_1$-$C_4$)alkylamino, aminosulfonyl, ($C_1$-$C_4$)alkylaminosulfonyl, di-($C_1$-$C_4$)alkylaminosulfonyl, NHCO—($C_1$-$C_4$)alkyl (($C_1$-$C_4$)alkylcarbonylamino), and also more preferably are phenyl or hetaryl, each of which is optionally mono- or disubstituted identically or differently, where (in the case of hetaryl) at least one carbonyl group may optionally be present and/or where possible substituents are in each case as follows: cyano, halogen, ($C_3$-$C_6$)cycloalkyl, ($C_3$-$C_6$)cycloalkyl-($C_3$-$C_6$)cycloalkyl, ($C_1$-$C_4$)alkyl-($C_3$-$C_6$)cycloalkyl, halo($C_3$-$C_6$)cycloalkyl, ($C_1$-$C_4$)alkyl, ($C_1$-$C_4$)haloalkyl, ($C_1$-$C_4$)cyanoalkyl, ($C_2$-$C_4$)alkenyl, ($C_2$-$C_4$)haloalkenyl, ($C_2$-$C_4$)cyanoalkenyl, ($C_2$-$C_4$)alkynyl, ($C_2$-$C_4$)haloalkynyl, ($C_2$-$C_4$)cyanoalkynyl, ($C_1$-$C_4$)alkoxy, ($C_1$-$C_4$)haloalkoxy, ($C_1$-$C_4$)alkylhydroxyimino, ($C_1$-$C_4$)alkoxyimino, ($C_1$-$C_4$)alkyl-($C_1$-$C_4$)alkoxyimino, ($C_1$-$C_4$)alkylthio, ($C_1$-$C_4$)haloalkylthio, ($C_1$-$C_4$)alkylsulfinyl, ($C_1$-$C_4$)haloalkylsulfinyl, ($C_1$-$C_4$)alkylsulfonyl, ($C_1$-$C_4$)haloalkylsulfonyl, ($C_1$-$C_4$)alkylsulfonyloxy, ($C_1$-$C_4$)alkylcarbonyl, ($C_1$-$C_4$)haloalkylcarbonyl, aminocarbonyl, ($C_1$-$C_4$)alkylaminocarbonyl, ($C_1$-$C_4$)alkylsulfonylamino, ($C_1$-$C_4$)alkylamino, di-($C_1$-$C_4$)alkylamino, aminosulfonyl, ($C_1$-$C_4$)alkylaminosulfonyl, di-($C_1$-$C_4$)alkylaminosulfonyl, NHCO—($C_1$-$C_4$)alkyl (($C_1$-$C_4$)alkylcarbonylamino), where only one or two of the $R^{10}$, $R^{11}$, $R^{12}$, $R^{13}$ radicals is/are a substituent other than hydrogen, Q is more preferably a heteroaromatic 9-membered or 12-membered fused bicyclic or tricyclic ring system from the group of Q1 to Q20,

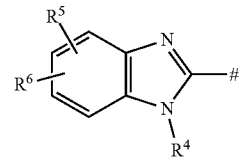

Q1

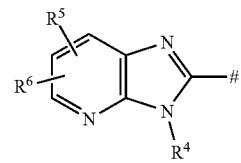

Q2

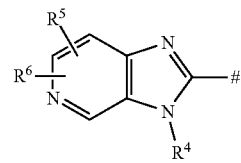

Q3

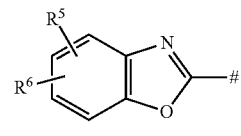

Q4

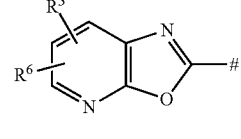

Q5

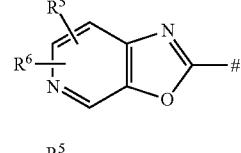

Q6

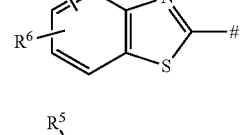

Q7

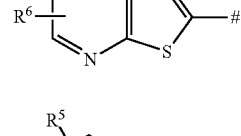

Q8

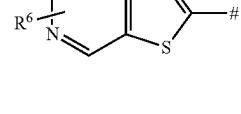

Q9

Q10

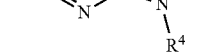

Q11

Q14

Q15

Q16

Q17

Q18

Q19

Q20

R⁴ is more preferably ($C_1$-$C_4$)-alkyl, ($C_1$-$C_4$)-haloalkyl, ($C_1$-$C_4$)-cyanoalkyl, ($C_1$-$C_4$)-hydroxyalkyl, ($C_1$-$C_4$)-alkoxy-($C_1$-$C_4$)-alkyl, ($C_1$-$C_4$)-haloalkoxy-($C_1$-$C_4$)-alkyl, ($C_2$-$C_4$)-alkenyl, ($C_2$-$C_4$)-alkenyloxy-($C_1$-$C_4$)-alkyl, ($C_2$-$C_4$)-haloalkenyloxy-($C_1$-$C_4$)-alkyl, ($C_2$-$C_4$)-haloalkenyl, ($C_2$-$C_4$)cyanoalkenyl, ($C_2$-$C_4$)-alkynyl, ($C_2$-$C_4$)-alkynyloxyl-($C_1$-$C_4$)-alkyl, ($C_2$-$C_4$)-haloalkynyl, ($C_3$-$C_6$)-cycloalkyl, ($C_3$-$C_6$)-cycloalkyl-($C_3$-$C_6$)-cycloalkyl, ($C_1$-$C_4$)-alkyl-($C_3$-$C_6$)-cycloalkyl, halo-($C_3$-$C_6$)-cycloalkyl, ($C_1$-$C_4$)-alkylthio-($C_1$-$C_4$)-alkyl, ($C_1$-$C_4$)-alkylsulfinyl-($C_1$-$C_4$)-alkyl, ($C_1$-$C_4$)-alkylsulfonyl-($C_1$-$C_4$)-alkyl or ($C_1$-$C_4$)-alkylcarbonyl-($C_1$-$C_4$)-alkyl, $R^5$, $R^6$ are independently more preferably hydrogen, cyano, halogen, ($C_1$-$C_4$)-alkyl, ($C_1$-$C_4$)-haloalkyl, ($C_2$-$C_4$)-alkenyl, ($C_2$-$C_4$)-haloalkenyl, ($C_1$-$C_4$)-alkynyl, ($C_2$-$C_4$)-haloalkynyl, ($C_3$-$C_6$)-cycloalkyl, ($C_3$-$C_6$)-cycloalkyl-($C_3$-$C_6$)-cycloalkyl, ($C_1$-$C_4$)-alkyl-($C_3$-$C_6$)-cycloalkyl, ($C_1$-$C_4$)-alkoxy, ($C_1$-$C_4$)-haloalkoxy, ($C_1$-$C_4$)-alkoxyimino, ($C_1$-$C_4$)-alkylthio, ($C_1$-$C_4$)-haloalkylthio, ($C_1$-$C_4$)-alkylsulfinyl, ($C_1$-$C_4$)-haloalkylsulfinyl, ($C_1$-$C_4$)-alkylsulfonyl, ($C_1$-$C_4$)-haloalkylsulfonyl, ($C_1$-$C_4$)-alkylsulfonyloxy, ($C_1$-$C_4$)-alkylcarbonyl, ($C_1$-$C_4$)-haloalkylcarbonyl, aminocarbonyl, ($C_4$-$C_4$)-alkylaminocarbonyl, di-($C_1$-$C_4$)-alkylaminocarbonyl, ($C_1$-$C_4$)-alkylsulfonylamino, ($C_1$-$C_4$)-alkylamino, di-($C_1$-$C_4$)-alkylamino, aminosulfonyl, ($C_1$-$C_4$)-alkylaminosulfonyl or di-($C_1$-$C_4$)-alkylaminosulfonyl, n is more preferably 0, 1 or 2.

Configuration 4-1

Aa is even more preferably nitrogen or =C($R^{10}$)—,

Ab is even more preferably nitrogen or =C($R^{11}$)—,

Ac is even more preferably nitrogen or =C($R^{12}$)—,

Ad is even more preferably nitrogen or =C($R^{13}$)—, where not more than two of Aa, Ab, Ac and Ad can be nitrogens, $R^1$ is even more preferably methyl, ethyl, n-propyl, isopropyl, cyclopropyl, n-butyl, isobutyl, tert-butyl, cyclobutyl, fluoromethyl, difluoromethyl, trifluoromethyl, fluoroethyl, difluoroethyl, trifluoroethyl, tetrafluoroethyl or pentafluoroethyl, $R^{10}$, $R^{11}$, $R^{12}$, $R^{13}$ are even more preferably independently hydrogen, cyano, halogen, ($C_1$-$C_4$)alkyl, ($C_1$-$C_4$)haloalkyl, ($C_1$-$C_4$)alkoxy, ($C_1$-$C_4$)haloalkoxy, ($C_1$-$C_4$)alkylthio, ($C_1$-$C_4$)alkylsulfinyl, ($C_1$-$C_4$)alkylsulfonyl, ($C_1$-$C_4$)haloalkylthio, ($C_1$-$C_4$)haloalkylsulfinyl, ($C_1$-$C_4$)haloalkylsulfonyl or NHCO—($C_1$-$C_4$)alkyl (($C_1$-$C_4$)alkylcarbonylamino), where only one or two of the $R^{10}$, $R^{11}$, $R^{12}$, $R^{13}$ radicals is/are a substituent other than hydrogen, Q is even more preferably a heteroaromatic 9-membered or 12-membered fused bicyclic or tricyclic ring system from the group of Q2, Q3, Q5, Q6, Q8, Q9, Q10, Q11, Q14, Q15, Q16 or Q19,

Q2

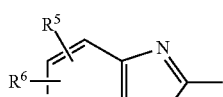

Q3

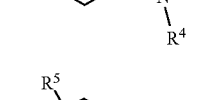

Q5

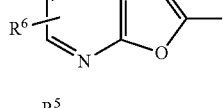

Q6

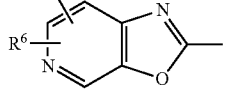

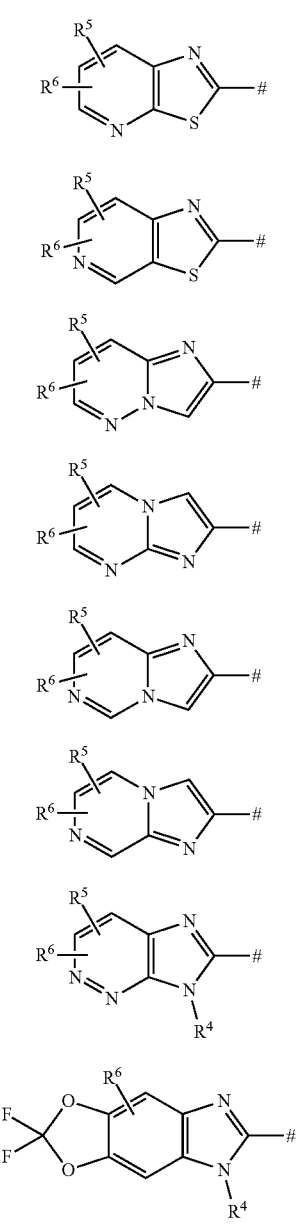

R⁴ is even more preferably $(C_1-C_4)$-alkyl or $(C_1-C_4)$-alkoxy-$(C_1-C_4)$-alkyl, R⁵ is even more preferably hydrogen, cyano, halogen, $(C_1-C_4)$alkyl, $(C_1-C_4)$haloalkyl, $(C_3-C_6)$cycloalkyl, $(C_3-C_6)$cycloalkyl-$(C_3-C_6)$cycloalkyl, $(C_1-C_4)$alkyl-$(C_3-C_6)$cycloalkyl, $(C_1-C_4)$alkoxy, $(C_1-C_4)$haloalkoxy, $(C_1-C_4)$alkoxyimino, $(C_1-C_4)$alkylthio, $(C_1-C_4)$haloalkylthio, $(C_1-C_4)$alkylsulfinyl, $(C_1-C_4)$haloalkylsulfinyl, $(C_1-C_4)$alkylsulfonyl, $(C_1-C_4)$haloalkylsulfonyl, $(C_1-C_4)$alkylcarbonyl, $(C_1-C_4)$haloalkylcarbonyl, $(C_1-C_4)$alkylaminocarbonyl, di-$(C_1-C_4)$alkylaminocarbonyl, $(C_1-C_4)$alkylsulfonylamino, $(C_1-C_4)$alkylaminosulfonyl or di-$(C_1-C_4)$alkylaminosulfonyl, R⁶ is even more preferably hydrogen.

n is even more preferably 0, 1 or 2.

Configuration 4-2

Aa, Ab, Ac, Ad, Q, R¹, R⁴, R⁵, R⁶ and n have the definitions given in configuration 4-1, and R¹⁰, R¹¹, R¹², R¹³ are even more preferably independently hydrogen, cyano, halogen, $(C_1-C_4)$alkyl, $(C_3-C_6)$cycloalkyl, aminocarbonyl, $(C_1-C_4)$haloalkyl, $(C_1-C_4)$alkoxy, $(C_1-C_4)$haloalkoxy, $(C_1-C_4)$alkylthio, $(C_1-C_4)$alkylsulfinyl, $(C_1-C_4)$alkylsulfonyl, $(C_1-C_4)$haloalkylthio, $(C_1-C_4)$haloalkylsulfinyl, $(C_1-C_4)$haloalkylsulfonyl or NHCO—$(C_1-C_4)$alkyl ($(C_1-C_4)$alkylcarbonylamino), where only one or two of the R¹⁰, R¹¹, R¹², R¹³ radicals is/are a substituent other than hydrogen.

Configuration 5-1

Aa is particularly nitrogen or =C(R¹⁰)—,

Ab is particularly nitrogen or =C(R¹¹)—,

Ac is particularly nitrogen or =C(R¹²)—,

Ad is particularly nitrogen or =C(R¹³)—, where not more than two of Aa, Ab, Ac and Ad can be nitrogens, R¹ is particularly methyl, ethyl, n-propyl, i-propyl or cyclopropyl, R¹⁰, R¹¹, R¹², R¹³ are particularly independently hydrogen, fluorine, chlorine, bromine, iodine, cyano, methyl, ethyl, trifluoromethyl, trifluoromethoxy, trifluoromethylthio, trifluoromethylsulfinyl, trifluoromethylsulfonyl or methoxy, where only one or two of the R¹⁰, R¹¹, R¹², R¹³ radicals is/are a substituent other than hydrogen, Q is particularly a heteroaromatic 9-membered fused bicyclic ring system from the group of Q2, Q3, Q10, Q14 or Q16,

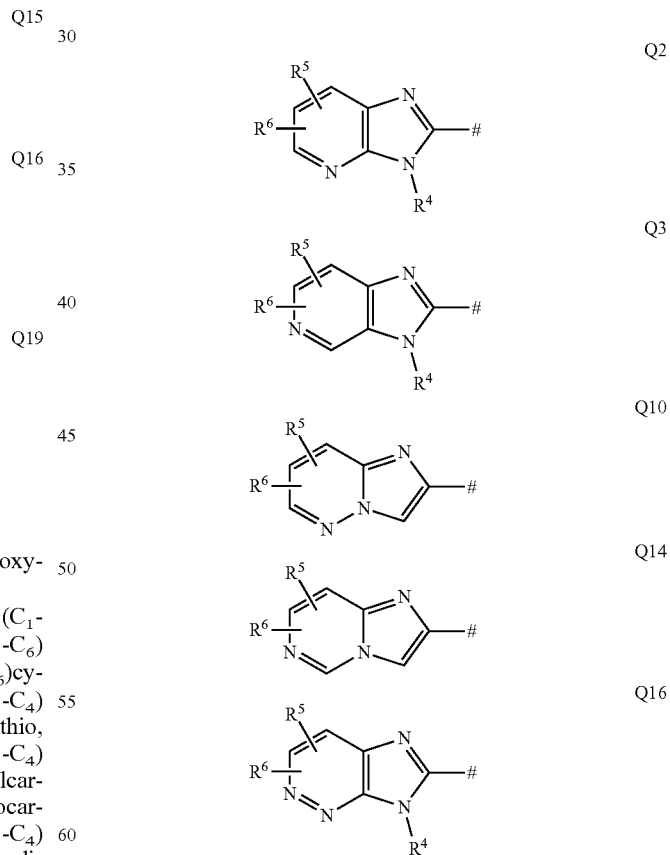

R⁴ is particularly methyl, ethyl, isopropyl, methoxymethyl or methoxyethyl,

R⁵ is even more preferably fluorine, chlorine, bromine, fluoromethyl, difluoromethyl, trifluoromethyl, fluoroethyl ($CH_2CFH_2$, $CHFCH_3$), difluoroethyl ($CF_2CH_3$, CH$_2$CHF$_2$, CHFCFH$_2$), trifluoroethyl (CH$_2$CF$_3$, CHFCHF$_2$, CF$_2$CFH$_2$), tetrafluoroethyl (CHFCF$_3$, CF$_2$CHF$_2$), pentafluoroethyl, trifluoromethoxy, difluorochloromethoxy, dichlorofluoromethoxy, trifluoromethylthio, trifluoromethylsulfinyl or trifluoromethylsulfonyl, R$^6$ is particularly hydrogen, n is particularly 0, 1 or 2.

Configuration 5-2

Aa, Ab, Ac, Ad, Q, R$^1$, R$^4$, R$^5$, R$^6$ and n have the definitions given in configuration 5-1, and R$^{10}$, R$^{11}$, R$^{12}$, R$^{13}$ are particularly independently hydrogen, fluorine, chlorine, bromine, iodine, cyano, methyl, ethyl, cyclopropyl, aminocarbonyl, trifluoromethyl, trifluoromethoxy, trifluoromethylthio, trifluoromethylsulfinyl, trifluoromethylsulfonyl or methoxy, where only one or two of the R$^{10}$, R$^{11}$, R$^{12}$, R$^{13}$ radicals is/are a substituent other than hydrogen.

Configuration 6-1

Aa is especially =C(R$^{10}$)—,

Ab is especially =C(R$^{11}$)—,

Ac is especially =C(R$^{12}$)—,

Ad is especially nitrogen or =C(R$^{13}$)—,

R$^1$ is especially ethyl,

R$^{10}$ is especially hydrogen or methyl,

R$^{11}$ is especially hydrogen, chlorine or trifluoromethyl,

R$^{12}$ is especially hydrogen or methyl,

R$^{13}$ is especially hydrogen,

Q is especially a heteroaromatic 9-membered fused bicyclic ring system from the group of Q2 or Q3,

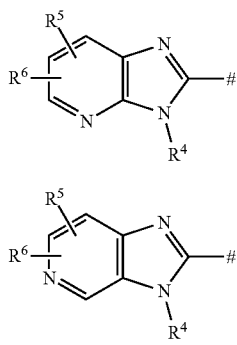

Q2

Q3

R$^4$ is especially methyl,

R$^5$ is especially trifluoromethyl or pentafluoroethyl,

R$^6$ is especially hydrogen, n is especially 0 or 2.

Configuration 6-2

Aa is especially =C(R$^{10}$)—,

Ab is especially =C(R$^{10}$)—,

Ac is especially =C(R$^{12}$)—,

Ad is especially nitrogen or =C(R$^{13}$)—,

R$^1$ is especially ethyl,

R$^{10}$ is especially hydrogen or methyl,

R$^{11}$ is especially hydrogen,

R$^{12}$ is especially hydrogen or methyl,

R$^{13}$ is especially hydrogen,

Q is especially a heteroaromatic 9-membered fused bicyclic ring system from the group of Q3, R$^4$ is especially methyl, R$^5$ is especially trifluoromethyl, R$^6$ is especially hydrogen, n is especially 2.

Configuration 6-3

Aa is especially =C(R$^{10}$)—,

Ab is especially =C(R$^{11}$)—,

Ac is especially =C(R$^{12}$)—,

Ad is especially nitrogen or =C(R$^{13}$)—,

R$^1$ is especially ethyl,

R$^{10}$ is especially hydrogen or methyl,

R$^{11}$ is especially hydrogen, chlorine, cyano, aminocarbonyl (—C(O)NH$_2$) or cyclopropyl, R$^{12}$ is especially hydrogen or methyl, R$^{13}$ is especially hydrogen, Q is especially a heteroaromatic 9-membered fused bicyclic ring system from the group of Q2 or Q3, R$^4$ is especially methyl, R$^5$ is especially trifluoromethyl, R$^6$ is especially hydrogen, n is especially 2.

The substituent Aa is identical to the substituent A$_a$; the substituent Ab is identical to the substituent A$_b$, the substituent Ac is identical to the substituent A$_c$, the substituent Ad is identical to the substituent A$_d$.

In a preferred embodiment, the invention relates to compounds of the formula (I) where Q is

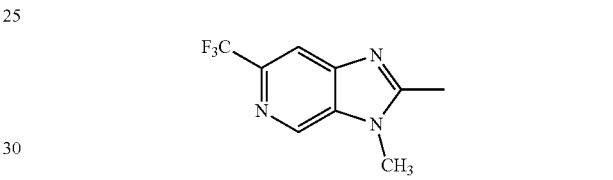

and Aa, Ab, Ac, Ad, R$^1$, R$^{10}$, R$^{11}$, R$^{12}$, R$^{13}$ and n have the definitions described in configuration (1) or configuration (2) or configuration (3) or configuration (4-1) or configuration (4-2) or configuration (5-1) or configuration (5-2) or configuration (6-1) or configuration (6-2) or configuration (6-3).

In a preferred embodiment, the invention relates to compounds of the formula (I) where Q is

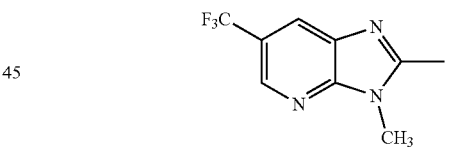

and Aa, Ab, Ac, Ad, R$^1$, R$^{10}$, R$^{11}$, R$^{12}$, R$^{13}$ and n have the definitions described in configuration (1) or configuration (2) or configuration (3) or configuration (4-1) or configuration (4-2) or configuration (5-1) or configuration (5-2) or configuration (6-1) or configuration (6-2) or configuration (6-3).

In a preferred embodiment, the invention relates to compounds of the formula (I) where Aa is =C(R$^{10}$)—, Ab is =C(R$^{11}$)—, Ac is =C(R$^{12}$)—, Ad is =C(R$^{13}$)—, and Q, R$^1$, R$^{10}$, R$^{11}$, R$^{12}$, R$^{13}$ and n have the definitions described in configuration (1) or configuration (2) or configuration (3) or configuration (4-1) or configuration (4-2) or configuration (5-1) or configuration (5-2) or configuration (6-1) or configuration (6-2) or configuration (6-3).

In a preferred embodiment, the invention relates to compounds of the formula (I) where
Aa is $=C(R^{10})$—,
Ab is $=C(R^{11})$—,
Ac is $=C(R^{12})$—,
Ad is nitrogen,
and Q, $R^1$, $R^{10}$, $R^{11}$, $R^{12}$ and n have the definitions described in configuration (1) or configuration (2) or configuration (3) or configuration (4-1) or configuration (4-2) or configuration (5-1) or configuration (5-2) or configuration (6-1) or configuration (6-2) or configuration (6-3).

In the preferred definitions, unless stated otherwise, halogen is selected from the group of fluorine, chlorine, bromine and iodine, preferably in turn from the group of fluorine, chlorine and bromine.

aryl (including as part of a larger unit, for example arylalkyl) is selected from the group of phenyl, benzyl, naphthyl, anthryl, phenanthrenyl, and is preferably in turn phenyl, hetaryl (synonymous with heteroaryl, including as part of a larger unit, for example hetarylalkyl) is selected from the group of furyl, thienyl, pyrrolyl, pyrazolyl, imidazolyl, triazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, tetrazolyl, pyridyl, pyrimidyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazole, quinolinyl, isoquinolinyl, cinnolinyl, phthalazinyl, quinazolinyl, quinoxalinyl, naphthyridinyl, benzotriazinyl, purinyl, pteridinyl and indolizinyl, heterocyclyl is a saturated 4-, 5- or 6-membered ring containing 1 or 2 nitrogen atoms and/or one oxygen atom and/or one sulfur atom, for example azetidinyl, pyrrolidinyl, piperidinyl, oxetanyl, tetrahydrofuranyl, tetrahydropyranyl, dioxanyl, thietanyl, tetrahydrothiophenyl, tetrahydrothiopyranyl, piperazinyl, morpholinyl and thiomorpholinyl.

In the particularly preferred definitions, unless stated otherwise, halogen is selected from the group of fluorine, chlorine, bromine and iodine, preferably in turn from the group of fluorine, chlorine and bromine.

aryl (including as part of a larger unit, for example arylalkyl) is selected from the group of phenyl, benzyl, naphthyl, anthryl, phenanthrenyl, and is preferably in turn phenyl, hetaryl (including as part of a larger unit, for example hetarylalkyl) is selected from the group consisting of pyridyl, pyrimidyl, pyrazinyl, pyridazinyl, pyrazolyl, imidazolyl, triazolyl, thiazolyl and tetrazolyl, heterocyclyl is selected from the group consisting of oxetanyl, tetrahydrofuryl and piperazinyl.

In the context of the present invention, unless defined differently elsewhere, the term "alkyl", either on its own or else in combination with further terms, for example haloalkyl, is understood to mean a radical of a saturated aliphatic hydrocarbon group which has 1 to 12 carbon atoms and may be branched or unbranched. Examples of $C_1$-$C_{12}$-alkyl radicals are methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1-ethylpropyl, 1,2-dimethylpropyl, hexyl, n-heptyl, n-octyl, n-nonyl, n-decyl, n-undecyl and n-dodecyl. Among these alkyl radicals, particular preference is given to $C_1$-$C_6$-alkyl radicals. Special preference is given to $C_1$-$C_4$-alkyl radicals.

According to the invention, unless defined differently elsewhere, the term "alkenyl", either on its own or else in combination with further terms, is understood to mean a straight-chain or branched $C_2$-$C_2$-alkenyl radical which has at least one double bond, for example vinyl, allyl, 1-propenyl, isopropenyl, 1-butenyl, 2-butenyl, 3-butenyl, 1,3-butadienyl, 1-pentenyl, 2-pentenyl, 3-pentenyl, 4-pentenyl, 1,3-pentadienyl, 1-hexenyl, 2-hexenyl, 3-hexenyl, 4-hexenyl, 5-hexenyl and 1,4-hexadienyl. Among these, preference is given to $C_2$-$C_6$-alkenyl radicals and particular preference to $C_2$-$C_4$-alkenyl radicals.

According to the invention, unless defined differently elsewhere, the term "alkynyl", either on its own or else in combination with further terms, is understood to mean a straight-chain or branched $C_2$-$C_{12}$-alkynyl radical which has at least one triple bond, for example ethynyl, 1-propynyl and propargyl.

Among these, preference is given to $C_3$-$C_6$-alkynyl radicals and particular preference to $C_3$-$C_4$-alkynyl radicals. The alkynyl radical may also contain at least one double bond.

According to the invention, unless defined differently elsewhere, the term "cycloalkyl", either on its own or else in combination with further terms, is understood to mean a $C_3$-$C_8$-cycloalkyl radical, for example cyclopropyl, cyclobutyl, cyclopentyl, cyclohexyl, cycloheptyl and cyclooctyl. Among these, preference is given to $C_3$-$C_6$-cycloalkyl radicals.

The term "alkoxy", either on its own or else in combination with further terms, for example haloalkoxy, is understood in the present case to mean an O-alkyl radical, where the term "alkyl" is as defined above.

Halogen-substituted radicals, for example haloalkyl, are mono- or polyhalogenated, up to the maximum number of possible substituents. In the case of polyhalogenation, the halogenation, the halogen atoms may be identical or different. Halogen here is fluorine, chlorine, bromine or iodine, especially fluorine, chlorine or bromine.

Unless stated otherwise, optionally substituted radicals may be mono- or poly substituted, where the substituents in the case of poly substitutions may be the same or different.

The radical definitions or illustrations given in general terms or listed within ranges of preference apply correspondingly to end products and to starting materials and intermediates. These radical definitions can be combined with one another as desired, i.e. including combinations between the respective ranges of preference.

Preference according to the invention is given to using compounds of the formula (I) which contain a combination of the meanings listed above as being preferred.

Particular preference according to the invention is given to using compounds of the formula (I) which contain a combination of the meanings listed above as being particularly preferred.

Very particular preference according to the invention is given to using compounds of the formula (I) which contain a combination of the definitions listed above as being very particularly preferred.

Most preference according to the invention is given to using compounds of the formula (I) which contain a combination of the meanings listed above as being most preferable.

Especially used according to the invention are compounds of the formula (I) which contain a combination of the meanings listed above as being especially emphasized.

Depending on the nature of the substituents, the compounds of the formula (I) may take the form of geometric and/or optically active isomers or corresponding isomer mixtures in different compositions.

These stereoisomers are, for example, enantiomers, diastereomers, atropisomers or geometric isomers. The invention therefore encompasses pure stereoisomers and any desired mixtures of these isomers.

The inventive compounds of the formula (I) can be obtained by the processes shown in the following schemes:

Process A

The compounds of the formula (I) in which Q is Q1 to Q9 and Q19 can be prepared by known methods, for example analogously to the processes described in WO02009/131237, WO2010/125985, WO2011/043404, WO2011/040629, WO2012/086848, WO2013/018928, WO2015/000715, WO2015/121136, WO 2016/124563 or WO 2016/124557.

Compounds of the formula (II) are either commercially available or can be prepared by known methods, for example analogously to the processes described in US2003/69257, WO2006/65703, WO02009/131237, WO2010/125985, WO2011/043404, WO2011/040629, WO02012/086848, WO2013/018928 or WO2015/000715.

Carboxylic acids of the formula (III) are either commercially available or can be prepared by known methods. Possible preparation routes are described in the processes G and H.

The reaction of the compounds of the formula (II) with carboxylic acids of the formula (III) can be carried out neat or in a solvent, preference being given to conducting the reaction in a solvent selected from customary solvents that are inert under the prevailing reaction conditions. Preference is given to ethers, for example diisopropyl ether, dioxane, tetrahydrofuran, 1,2-dimethoxyethane; halogenated hydrocarbons, for example dichloromethane, chloroform, carbon

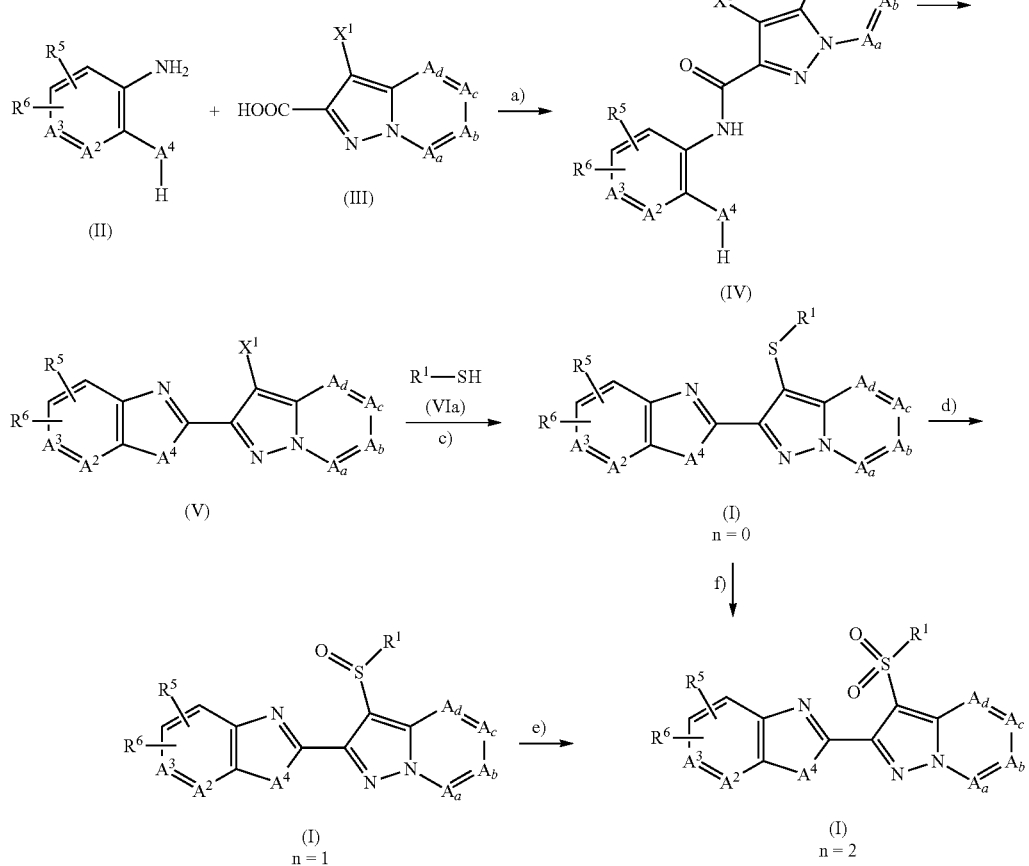

The radicals $R^1$, $R^4$, $R^5$, $R^6$, Aa, Ab, Ac, Ad and n have the definitions described above, $A^2$ and $A^3$ are CH or N (where $A^2$ and $A^3$ cannot simultaneously be N), $A^4$ is O, S or N—$R^4$ and $X^1$ is halogen.

Step a)

The compounds of the formula (IV) can be prepared in analogy to the process described in U.S. Pat. No. 5,576,335 by the reaction of compounds of the formula (II) with carboxylic acids of the formula (III) in the presence of a condensing agent or a base.

tetrachloride, 1,2-dichloroethane or chlorobenzene; nitriles, for example acetonitrile or propionitrile; aromatic hydrocarbons, for example toluene or xylene; aprotic polar solvents, for example N,N-dimethylformamide or N-methylpyrrolidone, or nitrogen compounds, for example pyridine.

Suitable condensing agents are, for example, carbodiimides such as 1-(3-dimethylaminopropyl)-3-ethylcarbodiimide hydrochloride (EDCI) or 1,3-dicyclohexylcarbodiimide.

Suitable bases are inorganic bases which are typically used in such reactions. Preference is given to using bases selected by way of example from the group consisting of acetates, phosphates, carbonates and hydrogencarbonates of alkali metals or alkaline earth metals. Particular preference is given here to sodium acetate, sodium phosphate, potassium phosphate, caesium carbonate, sodium carbonate, potassium carbonate, sodium hydrogencarbonate, potassium hydrogencarbonate.

The reaction can be effected under reduced pressure, at standard pressure or under elevated pressure and at temperatures of 0° C. to 180° C.; with preference, the reaction is carried out at standard pressure and temperatures of 20 to 140° C.

Step b)

The compounds of the formula (V) can be prepared by condensing the compounds of the formula (IV), for example analogously to the processes described in WO2009/131237, WO02010/125985, WO2011/043404, WO2011/040629, WO2012/086848, WO02013/018928, WO2015/000715 or WO 2015/121136.

The conversion to compounds of the formula (V) can be carried out neat or in a solvent, preference being given to conducting the reaction in a solvent selected from customary solvents that are inert under the prevailing reaction conditions. Preference is given to ethers, for example diisopropyl ether, dioxane, tetrahydrofuran, 1,2-dimethoxyethane, tert-butyl methyl ether; halogenated hydrocarbons, for example dichloromethane, chloroform, carbon tetrachloride, 1,2-dichloroethane or chlorobenzene; nitriles, for example acetonitrile or propionitrile; aromatic hydrocarbons, for example toluene or xylene; aprotic polar solvents, for example N,N-dimethylformamide or N-methylpyrrolidone, or nitrogen compounds, for example pyridine.

The reaction can be carried out in the presence of a condensing agent, an acid, a base or a chlorinating agent.

Examples of suitable condensing agents are carbodiimides such as 1-(3-dimethylaminopropyl)-3-ethylcarbodiimide hydrochloride (EDCI) or 1,3-dicyclohexylcarbodiimide; anhydrides such as acetic anhydride, trifluoroacetic anhydride; a mixture of triphenylphosphine, a base and carbon tetrachloride, or a mixture of triphenylphosphine and an azo diester, for example diethylazodicarboxylic acid.

Examples of suitable acids which can be used in the reaction described are sulfonic acids such as para-toluenesulfonic acid; carboxylic acids such as acetic acid, or polyphosphoric acids.

Examples of suitable bases are nitrogen heterocycles such as pyridine, picoline, 2,6-lutidine, 1,8-diazabicyclo[5.4.0]-7-undecene (DBU); tertiary amines such as triethylamine and N,N-diisopropylethylamine; inorganic bases such as potassium phosphate, potassium carbonate and sodium hydride.

An example of a suitable chlorinating agent is phosphorus oxychloride.

The reaction can be conducted under reduced pressure, at standard pressure or under elevated pressure, and at temperatures of 0° C. to 200° C.

Step c)

The compounds of the formula (I) where n is 0 can be prepared by reacting the compounds of the formula (V) with the compounds of the formula (VIa) in the presence of a base.

Mercaptan derivatives of the formula (Via), for example methyl mercaptan, ethyl mercaptan or isopropyl mercaptan, are either commercially available or can be prepared by known methods, for example analogously to the processes described in US2006/25633, US2006/111591, U.S. Pat. No. 2,820,062, Chemical Communications, 13 (2000), 1163-1164 or Journal of the American Chemical Society, 44 (1922), 1329.

The conversion to compounds of the formula (I) where n is 0 can be carried out neat or in a solvent, preference being given to conducting the reaction in a solvent selected from customary solvents that are inert under the prevailing reaction conditions. Preference is given to ethers, for example diisopropyl ether, dioxane, tetrahydrofuran, 1,2-dimethoxyethane, tert-butyl methyl ether; nitriles, for example acetonitrile or propionitrile; aromatic hydrocarbons, for example toluene or xylene; aprotic polar solvents, for example N,N-dimethylformamide, N-methylpyrrolidone or dimethyl sulfoxide.

Examples of suitable bases are inorganic bases from the group consisting of acetates, phosphates, hydrogencarbonates and carbonates of alkali metals or alkaline earth metals. Preference is given here to caesium carbonate, sodium carbonate, potassium carbonate and sodium hydrogencarbonate. Further suitable bases are alkali metal hydrides, for example sodium hydride.

The reaction can be conducted under reduced pressure, at standard pressure or under elevated pressure, and at temperatures of 0° C. to 200° C.

In the reaction described, $X^1$ is preferably a fluorine or chlorine atom.

As an alternative, if X1 is bromine, another option is trans-metallation with a suitable lithium base, followed by reaction with the appropriate commercially available disulfide. In this regard, see Bioorganic and Medicinal Chemistry Letters, 20 (2010), 2770-2775.

Suitable lithium bases are, for example, n-butyllithium.

The conversion to compound of the formula (I) where n is 0 can be conducted in neat form or in a solvent, preference being given to conducting the reaction in a solvent selected from customary solvents that are inert under the prevailing reaction conditions. Preference is given to ethers, for example diisopropyl ether, dioxane, tetrahydrofuran, 1,2-dimethoxyethane, tert-butyl methyl ether.

The reaction can be conducted under reduced pressure, at standard pressure or under elevated pressure, at temperatures of 0° C. to 200° C.

The reaction can be conducted in a microwave.

Step d)

The compounds of the formula (I) where n is 1 can be prepared by oxidizing the compounds of the formula (I) where n is 0. The oxidation is generally carried out in a solvent selected from customary solvents which are inert under the prevailing reaction conditions. Preference is given to halogenated hydrocarbons, for example dichloromethane, chloroform, carbon tetrachloride, 1,2-dichloroethane or chlorobenzene; alcohols such as methanol or ethanol; formic acid, acetic acid, propionic acid or water.

Examples of suitable oxidizing agents are hydrogen peroxide, meta-chloroperbenzoic acid or sodium periodate.

The reaction can be conducted under reduced pressure, at standard pressure or under elevated pressure, and at temperatures of −20° C. to 120° C.

Step e)

The compounds of the formula (I) where n is 2 can be prepared by oxidizing the compounds of the formula (I) where n is 1. The oxidation is generally carried out in a solvent. Preference is given to halogenated hydrocarbons, for example dichloromethane, chloroform, carbon tetrachloride, 1,2-dichloroethane or chlorobenzene; alcohols such as methanol or ethanol; formic acid, acetic acid, propionic acid or water.

Examples of suitable oxidizing agents are hydrogen peroxide and meta-chloroperbenzoic acid.

The reaction can be conducted under reduced pressure, at standard pressure or under elevated pressure, and at temperatures of −20° C. to 120° C.

Step f)

The compounds of the formula (I) where n is 2 can also be prepared in a one-step process by oxidizing the compounds of the formula (I) where n is 0. The oxidation is generally carried out in a solvent. Preference is given to halogenated hydrocarbons, for example dichloromethane, chloroform, carbon tetrachloride, 1,2-dichloroethane or chlorobenzene; alcohols such as methanol or ethanol; formic acid, acetic acid, propionic acid or water.

Examples of suitable oxidizing agents are hydrogen peroxide and meta-chloroperbenzoic acid.

The reaction can be conducted under reduced pressure, at standard pressure or under elevated pressure, and at temperatures of −20° C. to 120° C.

Process B

The compounds of the formula (I) in which Q represents Q10, Q11, Q14 or Q15 can be prepared by known methods, for example analogously to the processes described in US2009/203705, US2012/258951, WO2013/3298 or J. Med. Chem. 31, (1988), 1590.

The radicals $R^1$, $R^5$, $R^6$, Aa, Ab, Ac, Ad and n have the definitions described above. $A^2$, $A^3$, $A^4$ and $A^5$ are CH or N (where $A^2$, $A^3$, $A^4$ and $A^5$ are not all N) and $X^1$ is halogen.

Step a)

Carboxylic acids of the formula (III) are converted in analogy to the process described in WO02011/75643 or EP2671582 in the presence of O,N-dimethylhydroxylamine hydrochloride to Weinreb amides of the formula (VI).

Carboxylic acids of the formula (III) are either commercially available or can be prepared by known methods. Possible preparation routes are described in processes G and H.

Step b, c)

Compounds of the formula (VI) can then be converted by known methods, for example in analogy to the process described in WO02011/75643, with a Grignard reagent, for example methylmagnesium bromide, to ketones of the formula (VII). Compounds of the formula (VIII) are obtainable by subsequent halogenation analogously, for example, to the known method described in US2012/302573.

Step d)

The compounds of the formula (X) can be prepared by cyclizing the compounds of the formula (VIII) with amines of the formula (IX). The cyclization is effected, for example, in ethanol, acetonitrile or N,N-dimethylformamide by

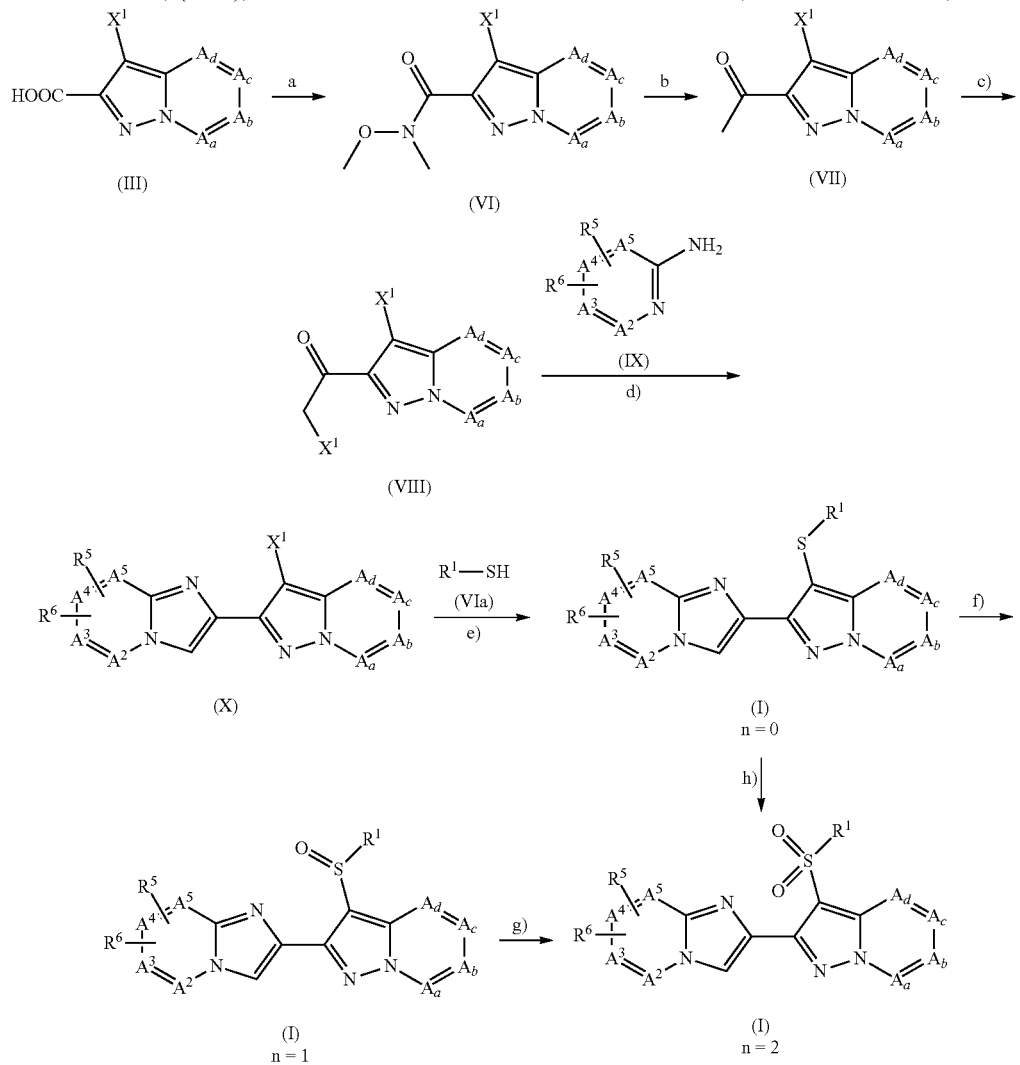

known methods in analogy to the processes described, for example, in WO2005/66177, WO2012/88411, WO2013/3298, US2009/203705, US2012/258951, WO2012/168733, WO2014/187762 or J. Med. Chem. 31 (1988) 1590-1595.

The compounds of the formula (IX) are commercially available.

Step e)

The compounds of the formula (I) where n is 0 can be prepared by reacting the compounds of the formula (V) with the compounds of the formula (VIa) in the presence of a base.

Mercaptan derivatives of the formula (VIa), for example methyl mercaptan, ethyl mercaptan or isopropyl mercaptan, are either commercially available or can be prepared by known methods, for example analogously to the processes described in US2006/25633, US2006/111591, U.S. Pat. No. 2,820,062, Chemical Communications, 13 (2000), 1163 or Journal of the American Chemical Society, 44 (1922), 1329.

The conversion to compound of the formula (I) where n is 0 can be conducted in neat form or in a solvent, preference being given to conducting the reaction in a solvent selected from customary solvents that are inert under the prevailing reaction conditions. Preference is given to ethers, for example diisopropyl ether, dioxane, tetrahydrofuran, 1,2-dimethoxyethane, tert-butyl methyl ether; nitriles, for example acetonitrile or propionitrile; aromatic hydrocarbons, for example toluene or xylene; aprotic polar solvents, for example N,N-dimethylformamide, N-methylpyrrolidone or dimethyl sulfoxide.

Examples of suitable bases are inorganic bases from the group consisting of acetates, phosphates, hydrogencarbonates and carbonates of alkali metals or alkaline earth metals. Preference is given here to caesium carbonate, sodium carbonate, potassium carbonate and sodium hydrogencarbonate. Further suitable bases are alkali metal hydrides, for example sodium hydride.

The reaction can be conducted under reduced pressure, at standard pressure or under elevated pressure and at temperatures of 0° C. to 200° C.

In the reaction described, $X^1$ is preferably a fluorine or chlorine atom.

As an alternative, if X1 is bromine, another option is trans-metallation with a suitable lithium base, followed by reaction with the appropriate commercially available disulfide. In this regard, see Bioorganic and Medicinal Chemistry Letters, 20 (2010), 2770-2775.

Suitable lithium bases are, for example, n-butyllithium.

The conversion to compound of the formula (I) where n is 0 can be conducted in neat form or in a solvent, preference being given to conducting the reaction in a solvent selected from customary solvents that are inert under the prevailing reaction conditions. Preference is given to ethers, for example diisopropyl ether, dioxane, tetrahydrofuran, 1,2-dimethoxyethane, tert-butyl methyl ether.

The reaction can be conducted under reduced pressure, at standard pressure or under elevated pressure, and at temperatures of 0° C. to 200° C.

The reaction can be conducted in a microwave.

Step f, g)

The compounds of the formula (I) where n is 1 can be prepared by oxidizing the compounds of the formula (I) where n is 0. The oxidation is carried out by known methods using a suitable oxidizing agent, for example hydrogen peroxide, meta-chloroperbenzoic acid or sodium periodate.

The compounds of the formula (I) where n is 2 can be prepared by oxidizing the compounds of the formula (I) where n is 1.

The oxidation is generally carried out in a solvent. Preference is given to halogenated hydrocarbons, for example dichloromethane, chloroform, carbon tetrachloride, 1,2-dichloroethane or chlorobenzene; alcohols such as methanol or ethanol; formic acid, acetic acid, propionic acid or water. Examples of suitable oxidizing agents are hydrogen peroxide and meta-chloroperbenzoic acid.

Step h)

The compounds of the formula (I) where n is 2 can also be prepared in a one-step process by oxidizing the compounds of the formula (I) where n is 0. The oxidation is generally carried out in a solvent. Preference is given to halogenated hydrocarbons, for example dichloromethane, chloroform, carbon tetrachloride, 1,2-dichloroethane or chlorobenzene; alcohols such as methanol or ethanol; formic acid, acetic acid, propionic acid or water. Examples of suitable oxidizing agents are hydrogen peroxide and meta-chloroperbenzoic acid.

Process C

The compounds of the formula (I) in which Q is Q16 can be prepared by known methods, for example analogously to the processes described in WO2014/142292.

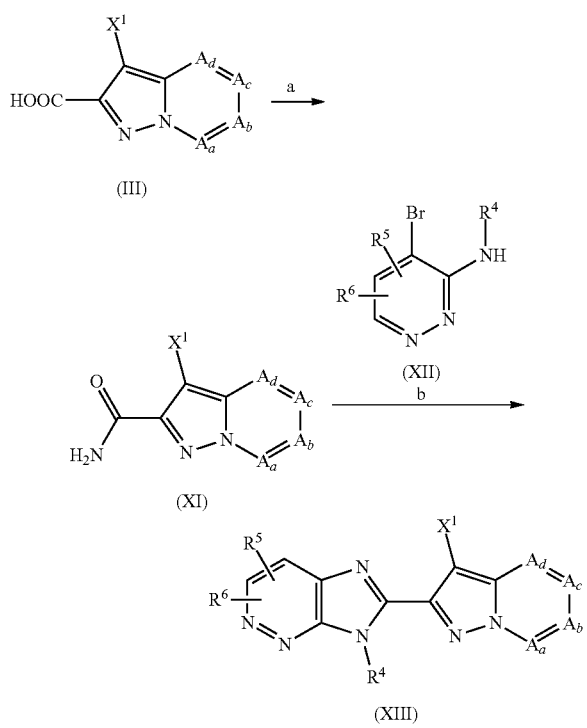

The $R^4$, $R^5$, $R^6$, Aa, Ab, Ac and Ad radicals have the definitions described above. $X^1$ is halogen.

Step a)

The compounds of the formula (XI) can be prepared in analogy to the process described in U.S. Pat. No. 5,374,646 or *Bioorganic and Medicinal Chemistry Letters* (2003), 13, 1093 by reacting compounds of the formula (III) with an ammonia source in the presence of a condensing agent.

Carboxylic acids of the formula (III) are either commercially available or can be prepared by known methods. Possible preparation routes are described in processes G and H.

In most cases, the ammonia source used is ammonium hydroxide.

The reaction of the compounds of the formula (III) with the ammonia source is preferably carried out in a solvent selected from customary solvents which are inert under the prevailing reaction conditions.

Preference is given to ethers, for example dioxane or tetrahydrofuran.

A suitable condensing agent is, for example, carbonyldiimidazole.

The reaction can be carried out under reduced pressure, at atmospheric pressure or under elevated pressure. Preferably, the reaction is carried out at atmospheric pressure and temperatures from 20 to 70° C.

Step b)

The compounds of the formula (XIII) can be prepared in analogy to the process described in WO2014/142292 by reacting compounds of the formula (XI) with compounds of the formula (XII) in the presence of a palladium catalyst in basic media.

Compounds of the formula (XII) can be prepared, for example, analogously to the processes described in WO2014/142292. A palladium catalyst used may, for example, be [1,1'-bis-(diphenylphosphino)ferrocene]dichloropalladium(II). Frequently, the bases used are inorganic bases such as potassium tert-butoxide.

The reaction is carried out in a solvent. Frequently, toluene is used.

The reaction can be carried out under reduced pressure, at atmospheric pressure or under elevated pressure. Preferably, the reaction is carried out at atmospheric pressure and temperatures from 20 to 110° C.

The further conversion of compounds of the formula (XIII) to compounds of the formula (I) is carried out analogously to process A.

Process D

The compounds of the formula (I) in which Q represents Q12, Q13, Q17 and Q18 can be prepared by known methods, for example analogously to the processes described in WO2010/091310, WO 2012/66061 or WO2013/099041.

example analogously to the processes described in WO2005/100353, WO 2012/66061 or in European Journal of Medicinal Chemistry 45 (2010), 2214.

Compounds of the formula (XVIII) are either commercially available or can be prepared by known methods, for example by synthesis of compounds of the formula (XVIII) in which $X^2$ is halogen and hydrogen is initially at the $X^1$ position, analogously to the processes described in Synthesis 47 (2015), 3221-3230, Chemical & Pharmaceutical Bulletin 34 (1986), 1023-1031 or WO2013/43521, and then the hydrogen is exchanged for a halogen in position $X^1$ with, for example, N-bromosuccinimide analogously to the method described in WO2009/70567.

The bases used are usually inorganic bases such as sodium hydride, potassium carbonate or caesium carbonate.

The conversion to compounds of the formula (XIX) is usually carried out in a solvent, preferably in a nitrile, for example acetonitrile or propionitrile, or in an aprotic polar solvent, for example N,N-dimethylformamide or N-methylpyrrolidone.

The reaction can be conducted under reduced pressure, at standard pressure or under elevated pressure, and at temperatures of 0° C. to 200° C.

Alternatively, the reaction of compounds of the formula (XVII) with compounds of the formula (XVIII) to give compounds of the formula (XIX) can also be carried out by palladium-catalysed N-arylation, e.g. analogously to the processes described in Angewandte Chemie Int. Ed. (2011), 50, 8944.

The further conversion of compounds of the formula (XIX) to compounds of the formula (I) is carried out analogously to process A.

Process E

As an alternative to process D, compounds of the formula (I) in which Q is Q17, Q18 and Q20 can be prepared as follows:

The $R^5$, $R^6$, Aa, Ab, Ac and Ad radicals have the definitions described above. $A^2$, and $A^3$ are CH or N. $X^1$ and $X^2$ are halogen.

Step a)

The compounds of the formula (XIX) can be prepared by reacting compounds of the formula (XVII) with compounds of the formula (XVIII) under basic conditions, for example analogously to the processes described in WO2010/091310, WO 2012/66061 or WO2013/099041.

Compounds of the formula (XVII) are either commercially available or can be prepared by known methods, for The $R^5$, $R^6$, Aa, Ab, Ac and Ad radicals have the definitions described above, $X^1$ is halogen, $A^2$, $A^3$ are nitrogen or CH.

Step a)

Compounds of the formula (XXII) can be prepared by condensation of compounds of the formula (XX) with compounds of the formula (XXI), as described in *Chemical Communications*, 2011, 47, 10133, WO2012/66061 A1, 2012, *Tetrahedron*, (1992), 48, 3091.

Compounds of the formula (XX) are either commercially available or can be prepared by known methods; see, for example, methods analogous to WO2012/66061 or *Australian Journal of Chemistry*, (1980), 33, 91.

Compounds of the formula (XXI) are either commercially available or can be prepared by known methods, for example analogously to the methods described in US2007/82902, US2012/122888 or Chemical and Pharmaceutical Bulletin 21 (1973), 2146-2160.

The condensation can be effected in neat form or in a solvent, preference being given to conducting the reaction in a solvent selected from customary solvents that are inert under the prevailing reaction conditions. Preference is given to alcohols such as ethanol or methanol or ethers such as THF.

The reaction is catalysed by use of Brønsted or Lewis acids, particular preference being given to using acetic acid and titanium salts such as titanium tetrachloride or titanium tetraethoxide.

Step b)

Analogously to WO2012/66061, or *Organic Letters*, (2011), 13, 3542, compounds of the formula (XXII) can be cyclized to compounds of the formula (XXIII). The cyclisation can be effected in neat form or in a solvent, preference being given to conducting the reaction in a solvent selected from customary solvents that are inert under the prevailing reaction conditions. Particular preference is given to high-boiling solvents such as toluene or DMSO.

The reaction can be conducted under reduced pressure, under standard pressure or under elevated pressure, and at temperatures of 0° C. to 200° C. Preference is given to a temperature greater than 100° C.

The reaction can be catalysed by addition of a copper(I) salt.

The further conversion of compounds of the formula (XXIII) to compounds of the formula (I) is effected analogously to process A.

Process F

Compounds of the formula (I) where n is 2 can alternatively be prepared in a one-stage process from compounds of the formula (V), (X), (XIII), (XIX) or (XXIII). The process is described with reference to the conversion of compounds of the formula (V) to compounds of the formula (I) from process A.

The $R^1$, $R^4$, $R^5$, $R^6$, Aa, Ab, Ac, and Ad radicals have the definitions described above, $A^2$ and $A^3$ are CH or N (where $A^2$ and $A^3$ cannot simultaneously be N), $A^4$ is O, S or N—$R^4$ and $X^1$ is halogen (preferably bromine or iodine). M is an alkali metal (preferably sodium or potassium).

Compounds of the formula (I) where n is 2 can be prepared in a one-stage process from compounds of the formula (V), for example in analogy to the processes described in Journal of Organic Chemistry 70 (2005) 2696-2700, by a halogen-sulfone exchange with a compound of the formula (VIb). The exchange is generally conducted in a solvent. Preference is given to using polar aprotic solvents, for example dimethyl sulfoxide and N,N-dimethylformamide.

The reaction is generally catalysed by addition of a copper(I) salt, for example copper(I) iodide.

Compounds of the formula (VIb) are either commercially available or can be prepared by known methods, for example analogously to the processes described in Organic Synthesis 57 (1977) 88-92; Tetrahedron Letters 9 (1979) 821-824 and Bulletin de la Societe Chimique de France 4 (1958) 447-450.

Examples of suitable sulfur reagents are salts of sulfinic acid.

The reaction can be conducted under reduced pressure, under standard pressure or under elevated pressure, and at temperatures of −20° C. to 120° C.

Process G

Carboxylic acids of the formula (III) are either commercially available or can be prepared by known methods, for example from pyridines of the formula (XXIV) analogously to the processes described in WO2011/15343, WO2014/14874 or WO2010/34738.

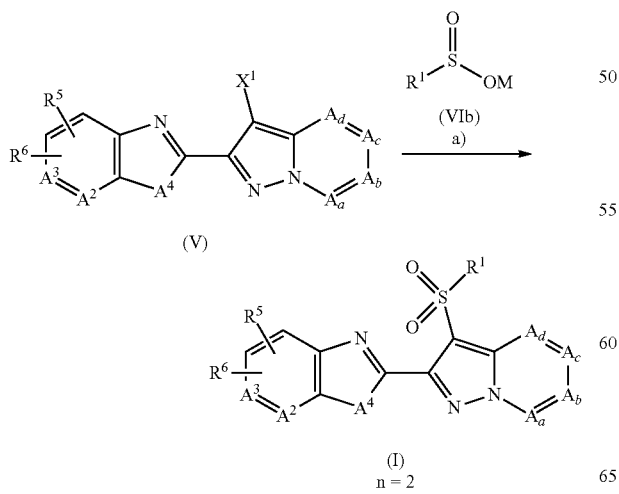

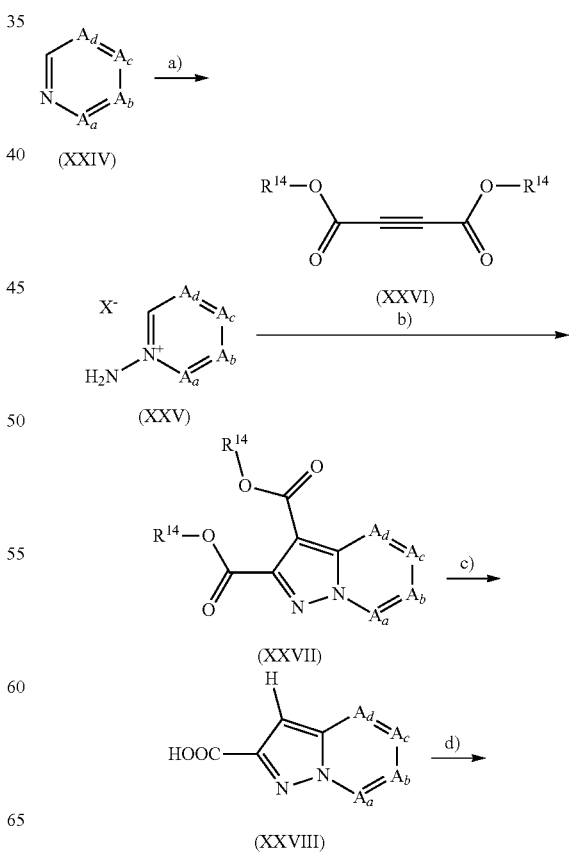

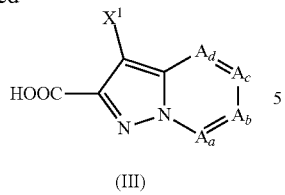

(III)

The Aa, Ab, Ac and Ad radicals have the definitions described above, X⁻ is a halide ion, preferably iodide, $X^1$ is halogen and $R^{14}$ is $(C_1-C_4)$alkyl.

Step a)

The compounds of the formula (XXV) can be converted to an N-iminopyridinium intermediate in analogy to the processes described in WO2011/15343, WO2014/14874 or WO2010/34738, by reaction of compounds of the formula (XXIV) with hydroxylamine-O-sulfonic acid in the presence of a base, for example potassium carbonate, and said intermediate is converted in a second step to the 1-aminopyridinium derivative of the formula (XXV) in the presence of an acid, for example hydriodic acid (HI), in a suitable solvent, for example ethanol. The pyridine derivatives of the formula (XXIV) are commercially available.

Steps b) and c)

Compounds of the formula (XXVII) can be prepared in analogy to the processes described in WO2011/15343, WO2014/14874 or WO2010/34738 from compounds of the formula (XXV) in a 1,3-dipolar cycloaddition with an alkyne of the formula (XXVI). If isomers form, these can be separated into the individual isomers by chromatographic methods. In this way, the diester of the formula (XXVII) can be obtained in isomerically pure form. By heating in a suitable acid, for example aqueous sulfuric acid, it is possible to convert compounds of the formula (XXVII) to acids of the formula (XXVIII) by decarboxylation and simultaneous hydrolysis of the ester function.

Step d)

Compounds of the formula (III) can be prepared by standard processes via a halogenation, for example in analogy to the processes described in WO2011/50284 or WO2016/12896, for example with N-chlorosuccinimide or N-bromosuccinimide as halogenating agent in a suitable solvent, for example dichloromethane or 1,2-dichloroethane.

Process H

In a further process, it is possible to prepare carboxylic acids of the formula (III) from 2-formylpyridine derivatives of the formula (XXIX), analogously to the processes described in Journal of Medicinal Chemistry 56 (2013), 9635-9645, Synthesis 16 (2005), 2751-2757 or WO2009/29625.

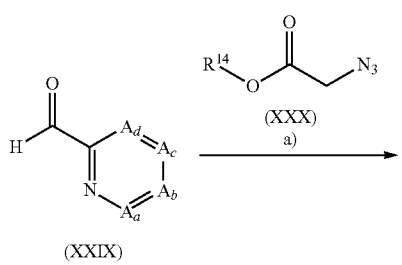

(XXIX)

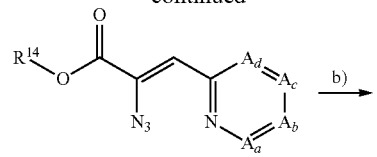

(XXXI)

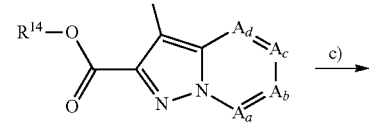

(XXXII)

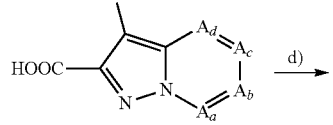

(XXVIII)

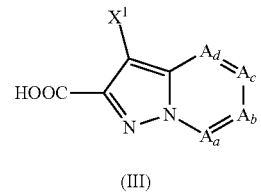

(III)

The Aa, Ab, Ac and Ad radicals have the definitions described above, $X^1$ is halogen and $R^{14}$ is $(C_1-C_4)$alkyl.

Step a)

The compounds of the formula (XXXI) can be prepared in analogy to the processes described in Journal of Medicinal Chemistry 56 (2013), 9635-9645, Synthesis 16 (2005), 2751-2757 or WO2009/29625, by reaction of compounds of the formula (XXIX) with an alkyl azidoacetate derivative of the formula (XXX) in the presence of a suitable base, for example sodium methoxide, in a suitable solvent, for example methanol. The compounds of the formula (XXIX) are commercially available or can be prepared by standard processes.

Step b)

Compounds of the formula (XXXII) can be prepared in analogy to the processes described in Journal of Medicinal Chemistry 56 (2013), 9635-9645, Synthesis 16 (2005), 2751-2757 or WO2009/29625, by cyclization of compounds of the formula (XXXI) in a suitable solvent, for example xylene. The reaction can be conducted under reduced pressure, under standard pressure or under elevated pressure, and at elevated temperatures. Preference is given to a temperature greater than 100° C.

Steps c, d)

The ester of the formula (XXXII) can be converted to the acid of the formula (XXVIII) using standard methods, for example with an alkali metal hydroxide as base, such as sodium hydroxide or lithium hydroxide, in an alcohol as solvent, for example ethanol or a mixture of tetrahydrofuran and water.

The further conversion to compounds of the formula (III) is effected by standard methods via a halogenation analogously to the manner described in process G.

Methods and Uses

The invention also relates to methods for controlling animal pests, in which compounds of the formula (I) are allowed to act on animal pests and/or their habitat. The control of the animal pests is preferably carried out in agriculture and forestry, and in material protection. This preferably excludes methods for surgical or therapeutic treatment of the human or animal body and diagnostic methods carried out on the human or animal body.

The invention further relates to the use of the compounds of the formula (I) as pesticides, especially crop protection compositions.

In the context of the present application, the term "pesticide" in each case also always encompasses the term "crop protection composition".

The compounds of the formula (I), given good plant tolerance, favourable endotherm toxicity and good environmental compatibility, are suitable for protecting plants and plant organs against biotic and abiotic stress factors, for increasing harvest yields, for improving the quality of the harvested material and for controlling animal pests, especially insects, arachnids, helminths, especially nematodes and molluscs, which are encountered in agriculture, in horticulture, in animal husbandry, in aquatic cultures, in forests, in gardens and leisure facilities, in the protection of stored products and of materials, and in the hygiene sector.

In the context of the present patent application, the term "hygiene" should be understood to mean any and all measures, provisions and procedures which have the aim of preventing diseases, especially infection diseases, and which serve to protect the health of humans and animals and/or protect the environment and/or maintain cleanliness. According to the invention, this especially includes measures for cleaning, disinfection and sterilization, for example of textiles or hard surfaces, especially surfaces made of glass, wood, cement, porcelain, ceramic, plastic or else metal(s), in order to ensure that these are free of hygiene pests and/or their secretions. The scope of protection of the invention in this regard preferably excludes surgical or therapeutic treatment procedures to be applied to the human body or the bodies of animals, and diagnostic procedures which are carried out on the human body or the bodies of animals.

The term "hygiene sector" covers all areas, technical fields and industrial applications in which these hygiene measures, provisions and procedures are important, for example with regard to hygiene in kitchens, bakeries, airports, bathrooms, swimming pools, department stores, hotels, hospitals, stables, animal keeping, etc.

The term "hygiene pest" should therefore be understood to mean one or more animal pests whose presence in the hygiene sector is problematic, especially for reasons of health. A main aim is therefore that of avoiding, or limiting to a minimum degree, the presence of hygiene pests and/or the exposure to these in the hygiene sector. This can especially be achieved through the use of a pesticide which can be used both for prevention of infestation and for prevention of an existing infestation. It is also possible to use formulations which prevent or reduce exposure to pests. Hygiene pests include, for example, the organisms mentioned below.

The term "hygiene protection" thus covers all acts by which these hygiene measures, provisions and procedures are maintained and/or improved.

The compounds of the formula (I) can preferably be used as pesticides. They are active against normally sensitive and resistant species and also against all or specific stages of development. The abovementioned pests include:

pests from the phylum of the Arthropoda, especially from the class of the Arachnida, for example *Acarus* spp., e.g. *Acarus siro, Aceria kuko, Aceria sheldoni, Aculops* spp., *Aculus* spp., e.g. *Aculus fockeui, Aculus schlechtendali, Amblyomma* spp., *Amphitetranychus viennensis, Argas* spp., *Boophilus* spp., *Brevipalpus* spp., e.g. *Brevipalpus phoenicis, Bryobia graminum, Bryobia praetiosa, Centruroides* spp., *Chorioptes* spp., *Dermanyssus gallinae, Dermatophagoides pteronyssinus, Dermatophagoides farinae, Dermacentor* spp., *Eotetranychus* spp., e.g. *Eotetranychus hicoriae, Epitrimerus pyri, Eutetranychus* spp., e.g. *Eutetranychus banksi, Eriophyes* spp., e.g. *Eriophyes pyri, Glycyphagus domesticus, Halotydeus destructor, Hemitarsonemus* spp., e.g. *Hemitarsonemus latus* (=*Polyphagotarsonemus latus*), *Hyalomma* spp., *Ixodes* spp., *Latrodectus* spp., *Loxosceles* spp., *Neutrombicula autumnalis, Nuphersa* spp., *Oligonychus* spp., e.g. *Oligonychus coffeae, Oligonychus coniferarum, Oligonychus ilicis, Oligonychus indicus, Oligonychus mangiferus, Oligonychus pratensis, Oligonychus punicae, Oligonychus yothersi, Ornithodorus* spp., *Ornithonyssus* spp., *Panonychus* spp., e.g. *Panonychus citri* (=*Metatetranychus citri*), *Panonychus ulmi* (=*Metatetranychus ulmi*), *Phyllocoptruta oleivora, Platytetranychus multidigituli, Polyphagotarsonemus latus, Psoroptes* spp., *Rhipicephalus* spp., *Rhizoglyphus* spp., *Sarcoptes* spp., *Scorpio maurus, Steneotarsonemus* spp., *Steneotarsonemus spinki, Tarsonemus* spp., e.g. *Tarsonemus confusus, Tarsonemus pallidus, Tetranychus* spp., e.g. *Tetranychus canadensis, Tetranychus cinnabarinus, Tetranychus turkestani, Tetranychus urticae, Trombicula alfreddugesi, Vaejovis* spp., *Vasates lycopersici;* from the class of the Chilopoda, for example *Geophilus* spp., *Scutigera* spp.;

from the order or the class of the Collembola, for example *Onychiurus armatus; Sminthurus viridis;* from the class of the Diplopoda, for example *Blaniulus guttulatus;* from the class of the Insecta, for example from the order of the Blattodea, e.g. *Blatta orientalis, Blattella asahinai, Blattella germanica, Leucophaea maderae, Loboptera decipiens, Neostylopyga rhombifolia, Panchlora* spp., *Parcoblatta* spp., *Periplaneta* spp., e.g. *Periplaneta americana, Periplaneta australasiae, Pycnoscelus surinamensis, Supella longipalpa;* from the order of the Coleoptera, for example *Acalymma vittatum, Acanthoscelides obtectus, Adoretus* spp., *Aethina tumida, Agelastica alni, Agriotes* spp., for example *Agriotes linneatus, Agriotes mancus, Alphitobius diaperinus, Amphimallon solstitialis, Anobium punctatum, Anoplophora* spp., *Anthonomus* spp., for example *Anthonomus grundis, Anthrenus* spp., *Apion* spp., *Apogonia* spp., *Atomaria* spp., for example *Atomaria linearis, Attagenus* spp., *Baris caerulescens, Bruchidius obtectus, Bruchus* spp., for example *Bruchus pisorum, Bruchus rufimanus, Cassida* spp., *Cerotoma trifurcata, Ceutorrhynchus* spp., for example *Ceutorrhynchus assimilis, Ceutorrhynchus quadridens, Ceutorrhynchus rapae, Chaetocnema* spp., for example *Chaetocnema confinis, Chaetocnema denticulata, Chaetocnema ectypa, Cleonus mendicus, Conoderus* spp., *Cosmopolites* spp., for example *Cosmopolites sordidus, Costelytra zealundica, Ctenicera* spp., *Curculio* spp., for example *Curculio caryae, Curculio caryatrypes, Curculio obtusus, Curculio sayi, Cryptolestes ferrugineus, Cryptolestes pusillus, Cryptorhynchus lapathi, Cryptorhynchus mangiferae, Cylindrocopturus* spp., *Cylindrocopturus adspersus, Cylindrocopturus furnissi, Dermestes* spp., *Diabrotica* spp., for example *Diabrotica balteata, Diabrotica barberi, Diabrotica undecimpunctata, Diabrotica undecimpunctata howardi, Diabrotica undecimpunctata undecimpunctata, Diabrotica virgifera virgifera, Diabrotica virgifera zeae, Dichocrocis* spp., *Dicladispa armigera, Diloboderus* spp., *Epicaerus* spp., *Epilachna* spp., for example

*Epilachna borealis, Epilachna varivestis, Epitrix* spp., for example *Epitrix cucumeris, Epitrix fuscula, Epitrix hirtipennis, Epitrix subcrinita, Epitrix tuberis, Faustinus* spp., *Gibbium psylloides, Gnathocerus cornutus, Hellula undalis, Heteronychus arator, Heteronyx* spp., *Hylamorpha elegans, Hylotrupes bajulus, Hypera postica, Hypomeces squamosus, Hypothenemus* spp., for example *Hypothenemus hampei, Hypothenemus obscurus, Hypothenemus pubescens, Lachnosterna consanguinea, Lasioderma serricorne, Latheticus oryzae, Lathridius* spp., *Lema* spp., *Leptinotarsa decemlineata, Leucoptera* spp., for example *Leucoptera coffeella, Lissorhoptrus oryzophilus, Listronotus* (=*Hyperodes*) spp., *Lixus* spp., *Luperodes* spp., *Luperomorpha xanthodera, Lyctus* spp., *Megascelis* spp., *Melanotus* spp., for example *Melanotus longulus oregonensis, Meligethes aeneus, Melolontha* spp., for example *Melolontha melolontha, Migdolus* spp., *Monochamus* spp., *Naupactus xanthographus, Necrobia* spp., *Neogalerucella* spp., *Niptus hololeucus, Oryctes rhinoceros, Oryzaephilus surinamensis, Oryzaphagus oryzae, Otiorhynchus* spp., for example *Otiorhynchus cribricollis, Otiorhynchus ligustici, Otiorhynchus ovatus, Otiorhynchus rugosostriarus, Otiorhynchus sulcatus, Oulema* spp., for example *Oulema melanopus, Oulema oryzae, Oxycetonia jucunda, Phaedon cochleariae, Phyllophaga* spp., *Phyllophaga helleri, Phyllotreta* spp., for example *Phyllotreta armoraciae, Phyllotreta pusilla, Phyllotreta ramosa, Phyllotreta striolata, Popillia japonica, Premnotrypes* spp., *Prostephanus truncatus, Psylliodes* spp., for example *Psylliodes affinis, Psylliodes chrysocephala, Psylliodes punctulata, Ptinus* spp., *Rhizobius ventralis, Rhizopertha dominica, Rhynchophorus* spp., *Rhynchophorus ferrugineus, Rhynchophorus palmarum, Sinoxylon perforans, Sitophilus* spp., for example *Sitophilus granarius, Sitophilus linearis, Sitophilus oryzae, Sitophilus zeamais, Sphenophorus* spp., *Stegobium paniceum, Sternechus* spp., for example *Sternechus paludatus, Symphyletes* spp., *Tanymecus* spp., for example *Tanymecus dilaticollis, Tanymecus indicus, Tanymecus palliatus, Tenebrio molitor, Tenebrioides mauretanicus, Tribolium* spp., for example *Tribolium audax, Tribolium castaneum, Tribolium confusum, Trogoderma* spp., *Tychius* spp., *Xylotrechus* spp., *Zabrus* spp., for example *Zabrus tenebrioides;* from the order of the Dermaptera, for example *Anisolabis maritime, Forficula auricularia, Labidura riparia;* from the order of the Diptera, for example *Aedes* spp., for example *Aedes aegypti, Aedes albopictus, Aedes sticticus, Aedes vexans, Agromyza* spp., for example *Agromyza frontella, Agromyza parvicornis, Anastrepha* spp., *Anopheles* spp., for example *Anopheles quadrimaculatus, Anopheles gambiae, Asphondylia* spp., *Bactrocera* spp., for example *Bactrocera cucurbitae, Bactrocera dorsalis, Bactrocera oleae, Bibio hortulanus, Calliphora erythrocephala, Calliphora vicina, Ceratitis capitata, Chironomus* spp., *Chrysomya* spp., *Chrysops* spp., *Chrysozona pluvialis, Cochliomya* spp., *Contarinia* spp., for example *Contarinia johnsoni, Contarinia nasturtii, Contarinia pyrivora, Contarinia schulzi, Contarinia sorghicola, Contarinia tritici, Cordylobia anthropophaga, Cricotopus sylvestris, Culex* spp., for example *Culex pipiens, Culex quinquefasciatus, Culicoides* spp., *Culiseta* spp., *Cuterebra* spp., *Dacus oleae, Dasineura* spp., for example *Dasineura brassicae, Delia* spp., for example *Delia antiqua, Delia coarctata, Delia florilega, Delia platura, Delia radicum, Dermatobia hominis, Drosophila* spp., for example *Drosophila melanogaster, Drosophila suzukii, Echinocnemus* spp., *Euleia heraclei, Fannia* spp., *Gasterophilus* spp., *Glossina* spp., *Haematopota* spp., *Hydrellia* spp., *Hydrellia griseola, Hylemya* spp., *Hippobosca* spp., *Hypoderma* spp., *Liriomyza* spp., for example *Liriomyza brassicae, Liriomyza huidobrensis, Liriomyza sativae, Lucilia* spp., for example *Lucilia cuprina, Lutzomyia* spp., *Mansonia* spp., *Musca* spp., for example *Musca domestica, Musca domestica vicina, Oestrus* spp., *Oscinella frit, Paratanytarsus* spp., *Paralauterborniella subcincta, Pegomya* or *Pegomyia* spp., for example *Pegomya betae, Pegomya hyoscyami, Pegomya rubivora, Phlebotomus* spp., *Phorbia* spp., *Phormia* spp., *Piophila casei, Platyparea poeciloptera, Prodiplosis* spp., *Psila rosae, Rhagoletis* spp., for example *Rhagoletis cingulata, Rhagoletis completa, Rhagoletis fausta, Rhagoletis indifferens, Rhagoletis mendax, Rhagoletis pomonella, Sarcophaga* spp., *Simulium* spp., for example *Simulium meridionale, Stomoxys* spp., *Tabanus* spp., *Tetanops* spp., *Tipula* spp., for example *Tipula paludosa, Tipula simplex, Toxotrypana curvicauda;* from the order of the Hemiptera, for example *Acizzia acaciaebaileyanae, Acizzia dodonaeae, Acizzia uncatoides, Acrida turrita, Acyrthosipon* spp., e.g. *Acyrthosiphon pisum, Acrogonia* spp., *Aeneolamia* spp., *Agonoscena* spp., *Aleurocanthus* spp., *Aleyrodes proletella, Aleurolobus barodensis, Aleurothrixus floccosus, Allocaridara malayensis, Amrasca* spp., e.g. *Amrasca bigutulla, Amrasca devastans, Anuraphis cardui, Aonidiella* spp., e.g. *Aonidiella aurantii, Aonidiella citrina, Aonidiella inornata, Aphanostigma piri, Aphis* spp., e.g. *Aphis citricola, Aphis craccivora, Aphis fabae, Aphis forbesi, Aphis glycines, Aphis gossypii, Aphis hederae, Aphis illinoisensis, Aphis middletoni, Aphis nasturtii, Aphis nerii, Aphis pomi, Aphis spiraecola, Aphis vibumiphila, Arboridia apicalis, Arytainilla* spp., *Aspidiella* spp., *Aspidiotus* spp., e.g. *Aspidiotus nerii, Atanus* spp., *Aulacorthum solani, Bemisia tabaci, Blastopsylla occidentalis, Boreioglycaspis melaleucae, Brachycaudus helichrysi, Brachycolus* spp., *Brevicoryne brassicae, Cacopsylla* spp., e.g. *Cacopsylla pyricola, Calligypona marginata, Capulinia* spp., *Cameocephala fulgida, Ceratovacuna lanigera, Cercopidae, Ceroplastes* spp., *Chaetosiphon fragaefolii, Chionaspis tegalensis, Chlorita onukii, Chondracris rosea, Chromaphis juglandicola, Chrysomphalus aonidum, Chrysomphalus ficus, Cicadulina mbila, Coccomytilus halli, Coccus* spp., e.g. *Coccus hesperidum, Coccus longulus, Coccus pseudomagnoliarum, Coccus viridis, Cryptomyzus ribis, Cryptoneossa* spp., *Ctenarytaina* spp., *Dalbulus* spp., *Dialeurodes chittendeni, Dialeurodes citri, Diaphorina citri, Diaspis* spp., *Diuraphis* spp., *Doralis* spp., *Drosicha* spp., *Dysaphis* spp., e.g. *Dysaphis apiifolia, Dysaphis plantaginea, Dysaphis tulipae, Dysmicoccus* spp., *Empoasca* spp., e.g. *Empoasca abrupta, Empoasca fabae, Empoasca maligna, Empoasca solana, Empoasca stevensi, Eriosoma* spp., e.g. *Eriosoma americanum, Eriosoma lanigerum, Eriosoma pyricola, Erythroneura* spp., *Eucalyptolyma* spp., *Euphyllura* spp., *Euscelis bilobatus, Ferrisia* spp., *Fiorinia* spp., *Furcaspis oceanica, Geococcus coffeae, Glycaspis* spp., *Heteropsylla cubana, Heteropsylla spinulosa, Homalodisca coagulata, Hyalopterus arundinis, Hyalopterus pruni, Icerya* spp., e.g. *Icerya purchasi, Idiocerus* spp., *Idioscopus* spp., *Laodelphax striatellus, Lecanium* spp., e.g. *Lecanium corni* (=*Parthenolecanium corni*), *Lepidosaphes* spp., e.g. *Lepidosaphes ulmi, Lipaphis erysimi, Lopholeucaspis japonica, Lycorma delicatula, Macrosiphum* spp., e.g. *Macrosiphum euphorbiae, Macrosiphum lilii, Macrosiphum rosae, Macrosteles facifrons, Mahanarva* spp., *Melanaphis sacchari, Metcalfiella* spp., *Metcalfa pruinosa, Metopolophium dirhodum, Monellia costalis, Monelliopsis pecanis, Myzus* spp., e.g. *Myzus ascalonicus, Myzus cerasi, Myzus ligustri, Myzus omatus, Myzus persicae, Myzus nicotianae, Nasonovia ribisnigri, Neomaskellia* spp., *Nephotettix* spp., e.g. *Nephotettix cincticeps, Nephotettix nigropictus, Nettigoniclla spectra, Nilaparvata lugens, Oncometopia* spp., *Orthezia praelonga, Oxya chinensis, Pachypsylla* spp., *Parabemisia myricae, Paratrioza* spp., e.g. *Paratrioza cockerelli, Parlatoria* spp., *Pemphigus* spp., e.g. *Pemphigus bursarius, Pemphigus populivenae, Peregrinus maidis, Perkinsiella* spp. *Phenacoccus* spp., e.g. *Phenacoccus madeirensis, Phloeomyzus passerinii, Phorodon humuli, Phylloxera* spp., e.g. *Phylloxera devastatrix, Phylloxera notabilis, Pinnaspis aspidistrae, Planococcus* spp., e.g. *Planococcus citri, Prosopidopsylla flava, Protopulvinaria pyriformis, Pseudaulacaspis pentagona, Pseudococcus* spp., e.g. *Pseudococcus calceolariae, Pseudococcus comstocki, Pseudococcus longispinus, Pseudococcus maritimus, Pseudococcus vibumi, Psyllopsis* spp., *Psylla* spp., e.g. *Psylla buxi, Psylla mali, Psylla pyri, Pteromalus* spp., *Pulvinaria* spp., *Pyrilla* spp., *Quadraspidiotus* spp., e.g. *Quadraspidiotus juglansregiae, Quadraspidiotus ostreaeformis, Quadraspidiotus perniciosus, Quesada gigas, Rastrococcus* spp., *Rhopalosiphum* spp., e.g. *Rhopalosiphum maidis, Rhopalosiphum oxyacanthae, Rhopalosiphum padi, Rhopalosiphum rufiabdominale, Saissetia* spp., e.g. *Saissetia coffeae, Saissetia miranda, Saissetia neglecta, Saissetia oleae, Scaphoideus titanus, Schizaphis graminum, Selenaspidus articulatus, Sipha flava, Sitobion avenae, Sogata* spp., *Sogatella furcifera, Sogatodes* spp., *Stictocephala festina, Siphoninus phillyreae, Tenalaphara malayensis, Tetragonocephela* spp., *Tinocallis caryaefoliae, Tomaspis* spp., *Toxoptera* spp., e.g. *Toxoptera aurantii, Toxoptera citricidus, Trialeurodes vaporariorum, Trioza* spp., e.g. *Trioza diospyri, Typhlocyba* spp., *Unaspis* spp., *Viteus vitifolii, Zygina* spp.;

from the suborder of the Heteroptera, for example *Aelia* spp., *Anasa tristis, Antestiopsis* spp., *Boisea* spp., *Blissus* spp., *Calocoris* spp., *Campylomma livida, Cavelerius* spp., *Cimex* spp., e.g. *Cimex adjunctus, Cimex hemipterus, Cimex lectularius, Cimex pilosellus, Collaria* spp., *Creontiades dilutus, Dasynus piperis, Dichelops furcatus, Diconocoris hewetti, Dysdercus* spp., *Euschistus* spp., e.g. *Euschistus heros, Euschistus servus, Euschistus tristigmus, Euschistus variolarius, Eurydema* spp., *Eurygaster* spp., *Halyomorpha halys, Heliopeltis* spp., *Horcias nobilellus, Leptocorisa* spp., *Leptocorisa varicornis, Leptoglossus occidentalis, Leptoglossus phyllopus, Lygocoris* spp., e.g. *Lygocoris pabulinus, Lygus* spp., e.g. *Lygus elisus, Lygus hesperus, Lygus lineolaris, Macropes excavatus, Megacopta cribraria, Miridae, Monalonion atratum, Nezara* spp., e.g. *Nezara viridula, Nysius* spp., *Oebalus* spp., *Pentomidae, Piesma quadrata, Piezodorus* spp., e.g. *Piezodorus guildinii, Psallus* spp., *Pseudacysta persea, Rhodnius* spp., *Sahlbergella singularis, Scaptocoris castanea, Scotinophora* spp., *Stephanitis nashi, Tibraca* spp., *Triatoma* spp.;

from the order of the Hymenoptera, for example *Acromyrmex* spp., *Athalia* spp., e.g. *Athalia rosae, Atta* spp., *Camponotus* spp., *Dolichovespula* spp., *Diprion* spp., e.g. *Diprion similis, Hoplocampa* spp., e.g. *Hoplocampa cookei, Hoplocampa testudinea, Lasius* spp., *Linepithema* (*Iridiomyrmex*) *humile, Monomorium pharaonis, Paratrechina* spp., *Paravespula* spp., *Plagiolepis* spp., *Sirex* spp., *Solenopsis invicta, Tapinoma* spp., *Technomyrmex albipes, Urocerus* spp., *Vespa* spp., e.g. *Vespa crabro, Wasmannia auropunctata, Xeris* spp.;

from the order of the Isopoda, for example *Armadillidium vulgare, Oniscus asellus, Porcellio scaber*; from the order of the Isoptera, for example *Coptotermes* spp., e.g. *Coptotermes formosanus, Cornitermes cumulans, Cryptotermes* spp., *Incisitermes* spp., *Kalotermes* spp., *Microtermes obesi, Nasutitermes* spp., *Odontotermes* spp., *Porotermes* spp., *Reticulitermes* spp., e.g. *Reticulitermes flavipes, Reticulitermes hesperus*;

from the order of the Lepidoptera, for example *Achroia grisella, Acronicta major, Adoxophyes* spp., e.g. *Adoxophyes orana, Aedia leucomelas, Agrotis* spp., e.g. *Agrotis segetum, Agrotis ipsilon, Alabama* spp., e.g. *Alabama argillacea, Amyelois transitella, Anarsia* spp., *Anticarsia* spp., e.g. *Anticarsia gemmatalis, Argyroploce* spp., *Autographa* spp., *Barathra brassicae, Blastodacna atra, Borbo cinnara, Bucculatrix thurberiella, Bupalus piniarius, Busseola* spp., *Cacoecia* spp., *Caloptilia theivora, Capua reticulana, Carpocapsa pomonella, Carposina niponensis, Cheimatobia brumata, Chilo* spp., e.g. *Chilo plejadellus, Chilo suppressalis, Choreutis pariana, Choristoneura* spp., *Chrysodeixis chalcites, Clysia ambiguella, Cnaphalocerus* spp., *Cnaphalocrocis medinalis, Cnephasia* spp., *Conopomorpha* spp., *Conotrachelus* spp., *Copitarsia* spp., *Cydia* spp., e.g. *Cydia nigricana, Cydia pomonella, Dalaca noctuides, Diaphania* spp., *Diparopsis* spp., *Diatraea saccharalis, Earias* spp., *Ecdytolopha aurantium, Elasmopalpus lignosellus, Eldana saccharina, Ephestia* spp., e.g. *Ephestia elutella, Ephestia kuehniella, Epinotia* spp., *Epiphyas postvittana, Erannis* spp., *Erschoviella musculana, Etiella* spp., *Eudocima* spp., *Eulia* spp., *Eupoecilia ambiguella, Euproctis* spp., e.g. *Euproctis chrysorrhoea, Euxoa* spp., *Feltia* spp., *Galleria mellonella, Gracillaria* spp., *Grapholitha* spp., e.g. *Grapholita molesta, Grapholita prunivora, Hedylepta* spp., *Helicoverpa* spp., e.g. *Helicoverpa armigera, Helicoverpa zea, Heliothis* spp., e.g. *Heliothis virescens Hofmannophila pseudospretella, Homoeosoma* spp., *Homona* spp., *Hyponomeuta padella, Kakivoria flavofasciata, Lampides* spp., *Laphygma* spp., *Laspeyresia molesta, Leucinodes orbonalis, Leucoptera* spp., e.g. *Leucoptera coffeella, Lithocolletis* spp., e.g. *Lithocolletis blancardella, Lithophane antennata, Lobesia* spp., e.g. *Lobesia botrana, Loxagrotis albicosta, Lymantria* spp., e.g. *Lymantria dispar, Lyonetia* spp., e.g. *Lyonetia clerkella, Malacosoma neustria, Maruca testulalis, Mamestra brassicae, Melanitis leda, Mocis* spp., *Monopis obviella, Mythimna separata, Nemapogon cloacellus, Nymphula* spp., *Oiketicus* spp., *Omphisa* spp., *Operophtera* spp., *Oria* spp., *Orthaga* spp., *Ostrinia* spp., e.g. *Ostrinia nubilalis, Panolis flammea, Parnara* spp., *Pectinophora* spp., e.g. *Pectinophora gossypiella, Perileucoptera* spp., *Phthorimaea* spp., e.g. *Phthorimaea operculella, Phyllocnistis citrella, Phyllonorycter* spp., e.g. *Phyllonorycter blancardella, Phyllonorycter crataegella, Pieris* spp., e.g. *Pieris rapae, Platynota stultana, Plodia interpunctella, Plusia* spp., *Plutella xylostella* (=*Plutella maculipennis*), *Prays* spp., *Prodenia* spp., *Protoparce* spp., *Pseudaletia* spp., e.g. *Pseudaletia unipuncta, Pseudoplusia includens, Pyrausta nubilalis, Rachiplusia nu, Schoenobius* spp., e.g. *Schoenobius bipunctifer, Scirpophaga* spp., e.g. *Scirpophaga innotata, Scotia segetum, Sesamia* spp., e.g. *Sesamia inferens, Sparganothis* spp., *Spodoptera* spp., e.g. *Spodoptera eradiana, Spodoptera exigua, Spodoptera frugiperda, Spodoptera praefica, Stathmopoda* spp., *Stenoma* spp., *Stomopteryx subsecivella, Synanthedon* spp., *Tecia solanivora, Thaumetopoea* spp., *Thermesia gemmatalis, Tinea cloacella, Tinea pellionella, Tineola bisselliella, Tortrix* spp., *Trichophaga tapetzella, Trichoplusia* spp., for example *Trichoplusia ni, Tryporyza incertulas, Tuta absoluta, Virachola* spp.;

from the order of the Orthoptera or Saltatoria, for example *Acheta domesticus*, *Dichroplus* spp., *Gryllotalpa* spp., e.g. *Gryllotalpa gryllotalpa, Hieroglyphus* spp., *Locusta* spp., e.g. *Locusta migratoria, Melanoplus* spp., e.g. *Melanoplus* devastator, Paratlanticus *ussuriensis, Schistocerca gregaria*; from the order of the Phthiraptera, for example *Damalinia* spp., *Haematopinus* spp., *Linognathus* spp., *Pediculus* spp., *Phylloxera vastatrix, Phthirus pubis, Trichodectes* spp.;

from the order of the Psocoptera, for example *Lepinotus* spp., *Liposcelis* spp.;

from the order of the Siphonaptera, for example *Ceratophyllus* spp., *Ctenocephalides* spp., e.g. *Ctenocephalides canis, Ctenocephalides felis, Pulex irritans, Tunga penetrans, Xenopsylla cheopis*; from the order of the Thysanoptera, for example *Anaphothrips obscurus, Baliothrips biformis, Chaetanaphothrips leeuweni, Drepanothrips reuteri, Enneothrips flavens, Frankliniella* spp., e.g. *Frankliniella fusca, Frankliniella occidentalis, Frankliniella schultzei, Frankliniella tritici, Frankliniella vaccinii, Frankliniella williamsi, Haplothrips* spp., *Heliothrips* spp., *Hercinothrips femoralis, Kakothrips* spp., *Rhipiphorothrips cruentatus, Scirtothrips* spp., *Taeniothrips cardamomi, Thrips* spp., e.g. *Thrips palmi, Thrips tabaci;* from the order of the Zygentoma (=*Thysanura*), for example *Ctenolepisma* spp., *Lepisma saccharina, Lepismodes inquilinus, Thermobia domestica;* from the class of the Symphyla, for example *Scutigerella* spp., e.g. *Scutigerella immaculata*; pests from the phylum of the Mollusca, for example from the class of the Bivalvia, e.g. *Dreissena* spp.; and also from the class of the Gastropoda, for example *Arion* spp., e.g. *Arion ater rufus, Biomphalaria* spp., *Bulinus* spp., *Deroceras* spp., e.g. *Deroceras laeve, Galba* spp., *Lymnaea* spp., *Oncomelania* spp., *Pomacea* spp., *Succinea* spp.;

plant pests from the phylum of the Nematoda, i.e. plant-parasitic nematodes, in particular *Aglenchus* spp., for example *Aglenchus agricola, Anguina* spp., for example *Anguina tritici, Aphelenchoides* spp., for example *Aphelenchoides arachidis, Aphelenchoides fragariae, Belonolaimus* spp., for example *Belonolaimus gracilis, Belonolaimus longicaudatus, Belonolaimus nortoni, Bursaphelenchus* spp., for example *Bursaphelenchus cocophilus, Bursaphelenchus eremus, Bursaphelenchus xylophilus, Cacopaurus* spp., for example *Cacopaurus pestis, Criconemella* spp., for example *Criconemella curvata, Criconemella onoensis, Criconemella ornata, Criconemella rusium, Criconemella xenoplax* (=*Mesocriconema xenoplax*), *Criconemoides* spp., for example *Criconemoides ferniae, Criconemoides onoense, Criconemoides ornatum, Ditylenchus* spp., for example *Ditylenchus dipsaci, Dolichodorus* spp., *Globodera* spp., for example *Globodera pallida, Globodera rostochiensis, Helicotylenchus* spp., for example *Helicotylenchus dihystera, Hemicriconemoides* spp., *Hemicycliophora* spp., *Heterodera* spp., for example *Heterodera avenae, Heterodera glycines, Heterodera schachtii, Hirschmaniella* spp., *Hoplolaimus* spp., *Longidorus* spp., for example *Longidorus africanus, Meloidogyne* spp., for example *Meloidogyne chitwoodi, Meloidogyne fallax, Meloidogyne hapla, Meloidogyne incognita, Meloinema* spp., *Nacobbus* spp., *Neotylenchus* spp., *Paralongidorus* spp., *Paraphelenchus* spp., *Paratrichodorus* spp., for example *Paratrichodorus minor, Paratylenchus* spp., *Pratylenchus* spp., for example *Pratylenchus penetrans, Pseudohalenchus* spp., *Psilenchus* spp., *Punctodera* spp., *Quinisulcius* spp., *Radopholus* spp., for example *Radopholus citrophilus, Radopholus similis, Rotylenchulus* spp., *Rotylenchus* spp., *Scutellonema* spp., *Subanguina* spp., *Trichodorus* spp., for example *Trichodorus obtusus, Trichodorus primitivus, Tylenchorhynchus* spp., for example *Tylenchorhynchus annulatus, Tylenchulus* spp., for example *Tylenchulus semipenetrans, Xiphinema* spp., for example *Xiphinema index.*

The compounds of the formula (I) can, as the case may be, at certain concentrations or application rates, also be used as herbicides, safeners, growth regulators or agents to improve plant properties, as microbicides or gametocides, for example as fungicides, antimycotics, bactericides, virucides (including agents against viroids) or as agents against MLO (*mycoplasma*-like organisms) and RLO (*rickettsia*-like organisms). They can, as the case may be, also be used as intermediates or precursors for the synthesis of other active ingredients.

Formulations

The present invention further relates to formulations and use forms prepared therefrom as pesticides, for example drench, drip and spray liquors, comprising at least one compound of the formula (I). Optionally, the use forms comprise further pesticides and/or adjuvants which improve action, such as penetrants, e.g. vegetable oils, for example rapeseed oil, sunflower oil, mineral oils, for example paraffin oils, alkyl esters of vegetable fatty acids, for example rapeseed oil methyl ester or soya oil methyl ester, or alkanol alkoxylates and/or spreaders, for example alkylsiloxanes and/or salts, for example organic or inorganic ammonium or phosphonium salts, for example ammonium sulfate or diammonium hydrogenphosphate and/or retention promoters, for example dioctyl sulfosuccinate or hydroxypropylguar polymers and/or humectants, for example glycerol and/or fertilizers, for example ammonium-, potassium- or phosphorus-containing fertilizers.

Customary formulations are, for example, water-soluble liquids (SL), emulsion concentrates (EC), emulsions in water (EW), suspension concentrates (SC, SE, FS, OD), water-dispersible granules (WG), granules (GR) and capsule concentrates (CS); these and further possible formulation types are described, for example, by Crop Life International and in Pesticide Specifications, Manual on development and use of FAO and WHO specifications for pesticides, FAO Plant Production and Protection Papers—173, prepared by the FAO/WHO Joint Meeting on Pesticide Specifications, 2004, ISBN: 9251048576. The formulations, in addition to one or more compounds of the formula (I), optionally comprise further active agrochemical ingredients.

Preference is given to formulations or use forms comprising auxiliaries, for example extenders, solvents, spontaneity promoters, carriers, emulsifiers, dispersants, frost protection agents, biocides, thickeners and/or further auxiliaries, for example adjuvants. An adjuvant in this context is a component which enhances the biological effect of the formulation, without the component itself having any biological effect. Examples of adjuvants are agents which promote retention, spreading, attachment to the leaf surface or penetration.

These formulations are produced in a known manner, for example by mixing the compounds of the formula (I) with auxiliaries, for example extenders, solvents and/or solid carriers and/or other auxiliaries, for example surfactants. The formulations are produced either in suitable facilities or else before or during application.

The auxiliaries used may be substances suitable for imparting special properties, such as certain physical, technical and/or biological properties, to the formulation of the compounds of the formula (I), or to the use forms prepared from these formulations (for example ready-to-use pesticides such as spray liquors or seed-dressing products).

Suitable extenders are, for example, water, polar and nonpolar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the simple and substituted amines, amides, lactams (such as N-alkylpyrrolidones) and lactones, the sulfones and sulfoxides (such as dimethyl sulfoxide).

If the extender used is water, it is also possible to use, for example, organic solvents as auxiliary solvents. Useful liquid solvents are essentially: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulfoxide, and also water.

In principle, it is possible to use all suitable solvents. Examples of suitable solvents are aromatic hydrocarbons, for example xylene, toluene or alkylnaphthalenes, chlorinated aromatic or chlorinated aliphatic hydrocarbons, for example chlorobenzene, chloroethylene or methylene chloride, aliphatic hydrocarbons, for example cyclohexane, paraffins, petroleum fractions, mineral and vegetable oils, alcohols, for example methanol, ethanol, isopropanol, butanol or glycol and their ethers and esters, ketones, for example acetone, methyl ethyl ketone, methyl isobutyl ketone or cyclohexanone, strongly polar solvents, for example dimethyl sulfoxide, and water.

In principle, it is possible to use all suitable carriers. Suitable carriers include more particularly the following: e.g. ammonium salts and natural, finely ground rocks, such as kaolins, aluminas, talc, chalk, quartz, attapulgite, montmorillonite or diatomaceous earth, and synthetic, finely ground rocks, such as highly disperse silica, aluminium oxide and natural or synthetic silicates, resins, waxes and/or solid fertilizers. It is likewise possible to use mixtures of such carriers. Useful carriers for granules include: for example crushed and fractionated natural rocks such as calcite, marble, pumice, sepiolite, dolomite, and synthetic granules of inorganic and organic flours, and also granules of organic material such as sawdust, paper, coconut shells, maize cobs and tobacco stalks.

It is also possible to use liquefied gaseous extenders or solvents. Especially suitable extenders or carriers are those which are gaseous at standard temperature and under atmospheric pressure, for example aerosol propellants such as halogenated hydrocarbons, and also butane, propane, nitrogen and carbon dioxide.

Examples of emulsifiers and/or foam formers, dispersants or wetting agents having ionic or nonionic properties or mixtures of these surface-active substances are salts of polyacrylic acid, salts of lignosulfonic acid, salts of phenolsulfonic acid or naphthalenesulfonic acid, polycondensates of ethylene oxide with fatty alcohols or with fatty acids or with fatty amines, with substituted phenols (preferably alkylphenols or arylphenols), salts of sulfosuccinic esters, taurine derivatives (preferably alkyl taurates), phosphoric esters of polyethoxylated alcohols or phenols, fatty acid esters of polyols, and derivatives of the compounds containing sulfates, sulfonates and phosphates, for example alkylaryl polyglycol ethers, alkylsulfonates, alkyl sulfates, arylsulfonates, protein hydrolysates, lignosulfite waste liquors and methylcellulose. The presence of a surfactant is advantageous if one of the compounds of the formula (I) and/or one of the inert carriers is insoluble in water and if the application takes place in water.

Further auxiliaries which may be present in the formulations and the use forms derived therefrom include dyes such as inorganic pigments, for example iron oxide, titanium oxide and Prussian Blue, and organic dyes such as alizarin dyes, azo dyes and metal phthalocyanine dyes, and nutrients and trace nutrients such as salts of iron, manganese, boron, copper, cobalt, molybdenum and zinc.

Additional components which may be present are stabilizers, such as cold stabilizers, preservatives, antioxidants, light stabilizers, or other agents which improve chemical and/or physical stability. Foam generators or antifoams may also be present.

In addition, the formulations and the use forms derived therefrom may also comprise, as additional auxiliaries, stickers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids. Further auxiliaries may be mineral and vegetable oils.

It is possible if appropriate for still further auxiliaries to be present in the formulations and the use forms derived therefrom. Examples of such additives are fragrances, protective colloids, binders, adhesives, thickeners, thixotropic agents, penetrants, retention promoters, stabilizers, sequestrants, complexing agents, humectants, spreaders. In general, the compounds of the formula (I) can be combined with any solid or liquid additive commonly used for formulation purposes.

Useful retention promoters include all those substances which reduce dynamic surface tension, for example dioctyl sulfosuccinate, or increase viscoelasticity, for example hydroxypropylguar polymers.

Useful penetrants in the present context are all those substances which are typically used to improve the penetration of active agrochemical ingredients into plants. Penetrants are defined in this context by their ability to penetrate from the (generally aqueous) application liquor and/or from the spray coating into the cuticle of the plant and hence to increase the mobility of the active ingredients in the cuticle. The method described in the literature (Baur et al., 1997, Pesticide Science 51, 131-152) can be used for determining this property. Examples include alcohol alkoxylates such as coconut fatty ethoxylate (10) or isotridecyl ethoxylate (12), fatty acid esters, for example rapeseed oil methyl ester or soya oil methyl ester, fatty amine alkoxylates, for example tallowamine ethoxylate (15), or ammonium and/or phosphonium salts, for example ammonium sulfate or diammonium hydrogenphosphate.

The formulations preferably comprise between 0.00000001% and 98% by weight of the compound of the formula (I), more preferably between 0.01% and 95% by weight of the compound of the formula (I), most preferably between 0.5% and 90% by weight of the compound of the formula (I), based on the weight of the formulation.

The content of the compound of the formula (I) in the use forms prepared from the formulations (in particular pesticides) may vary within wide ranges. The concentration of the compound of the formula (I) in the use forms may typically be between 0.00000001% and 95% by weight of the compound of the formula (I), preferably between 0.00001% and 1% by weight, based on the weight of the use form. Application is accomplished in a customary manner appropriate for the use forms.

Mixtures

The compounds of the formula (I) can also be used in a mixture with one or more suitable fungicides, bactericides, acaricides, molluscicides, nematicides, insecticides, microbiological agents, beneficial organisms, herbicides, fertilizers, bird repellents, phytotonics, sterilants, safeners, semiochemicals and/or plant growth regulators, in order thus, for example, to broaden the spectrum of action, prolong the period of action, enhance the rate of action, prevent repellency or prevent evolution of resistance. In addition, active ingredient combinations of this kind can improve plant growth and/or tolerance to abiotic factors, for example high or low temperatures, to drought or to elevated water content or soil salinity. It is also possible to improve flowering and fruiting performance, optimize germination capacity and root development, facilitate harvesting and improve yields, influence maturation, improve the quality and/or the nutritional value of the harvested products, prolong storage life and/or improve the processibility of the harvested products.

In addition, the compounds of the formula (I) may be present in a mixture with other active ingredients or semiochemicals such as attractants and/or bird repellents and/or plant activators and/or growth regulators and/or fertilizers. Likewise, the compounds of the formula (I) can be used to improve plant properties, for example growth, yield and quality of the harvested material.

In a particular embodiment according to the invention, the compounds of the formula (I) are present in formulations or in the use forms prepared from these formulations in a mixture with further compounds, preferably those as described below.

If one of the compounds mentioned below can occur in different tautomeric forms, these forms are also included even if not explicitly mentioned in each case. All the mixing components mentioned, as the case may be, may also form salts with suitable bases or acids if they are capable of doing so on the basis of their functional groups.

Insecticides/Acaricides/Nematicides

The active ingredients specified here with their common names are known and are described for example in "The Pesticide Manual", 16th ed., British Crop Protection Council 2012, or can be searched for on the Internet (e.g. http://www.alanwood.net/pesticides). The classification is based on the IRAC Mode of Action Classification Scheme applicable at the time of filing of this patent application.

(1) Acetylcholinesterase (AChE) inhibitors, for example carbamates, e.g. alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC and xylylcarb; or organophosphates, e.g. acephate, azamethiphos, azinphos-ethyl, azinphos-methyl, cadusafos, chlorethoxyfos, chlorfenvinphos, chlormephos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothiophosphoryl) salicylate, isoxathion, malathion, mecarbam, methamidophos, methidathion, mevinphos, monocrotophos, naled, omethoate, oxydemeton-methyl, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, triclorfon and vamidothion.

(2) GABA-gated chloride channel blockers, for example cyclodiene-organochlorines, e.g. chlordane and endosulfan or phenylpyrazoles (fiproles), e.g. ethiprole and fipronil.

(3) Sodium channel modulators, for example pyrethroids, e.g. acrinathrin, allethrin, d-cis-trans allethrin, d-trans allethrin, bifenthrin, bioallethrin, bioallethrin S-cyclopentenyl isomer, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin [(1R)-trans isomer], deltamethrin, empenthrin [(EZ)-(1R) isomer], esfenvalerate, etofenprox, fenpropathrin, fenvalerate, flucythrinate, flumethrin, tau-fluvalinate, halfenprox, imiprothrin, kadethrin, momfluorothrin, permethrin, phenothrin [(1R)-trans isomer], prallethrin, pyrethrins (pyrethrum), resmethrin, silafluofen, tefluthrin, tetramethrin, tetramethrin [(1R) isomer], tralomethrin and transfluthrin or DDT or methoxychlor.

(4) Nicotinic acetylcholine receptor (nAChR) competitive modulators, for example neonicotinoids, e.g. acetamiprid, clothianidin, dinotefuran, imidacloprid, nitenpyram, thiacloprid and thiamethoxam or nicotine or sulfoxaflor or flupyradifurone.

(5) Nicotinic acetylcholine receptor (nAChR) allosteric modulators, for example spinosyns, e.g. spinetoram and spinosad.

(6) Glutamate-gated chloride channel (GluCl) allosteric modulators, for example avermectins/milbemycins, e.g. abamectin, emamectin benzoate, lepimectin and milbemectin.

(7) Juvenile hormone mimetics, for example juvenile hormone analogues, e.g. hydroprene, kinoprene and methoprene or fenoxycarb or pyriproxyfen.

(8) Miscellaneous non-specific (multisite) inhibitors, for example alkyl halides, e.g. methyl bromide and other alkyl halides; or chloropicrin or sulfuryl fluoride or borax or tartar emetic or methyl isocyanate generator, e.g. diazomet and metam.

(9) Chordotonal organ modulators, e.g. pymetrozine or flonicamide.

(10) Mite growth inhibitors, for example clofentezine, hexythiazox and diflovidazin or etoxazole.

(11) Microbial disruptors of the insect midgut membrane, for example *Bacillus thuringiensis* subspecies *israelensis, Bacillus sphaericus, Bacillus thuringiensis* subspecies *aizawai, Bacillus thuringiensis* subspecies *kurstaki, Bacillus thuringiensis* subspecies *tenebrionis* and B.t. plant proteins: Cry1Ab, Cry1Ac, Cry1Fa, Cry1A.105, Cry2Ab, Vip3A, mCry3A, Cry3Ab, Cry3Bb, Cry34 Ab1/35Ab1.

(12) Inhibitors of mitochondrial ATP synthase, such as ATP disruptors, for example diafenthiuron or organotin compounds, e.g. azocyclotin, cyhexatin and fenbutatin oxide or propargite or tetradifon.

(13) Uncouplers of oxidative phosphorylation via disruption of the proton gradient, for example chlorfenapyr, DNOC and sulfluramid.

(14) Nicotinic acetylcholine receptor channel blockers, for example bensultap, cartap hydrochloride, thiocyclam, and thiosultap-sodium.

(15) Inhibitors of chitin biosynthesis, type 0, for example bistrifluron, chlorfluazuron, diflubenzuron, flucycloxuron, flufenoxuron, hexaflumuron, lufenuron, novaluron, novifluron, teflubenzuron and triflumuron.

(16) Inhibitors of chitin biosynthesis, type 1, for example buprofezin.

(17) Moulting disruptors (especially in the case of Diptera), for example cyromazine.

(18) Ecdysone receptor agonists, for example chromafenozide, halofenozide, methoxyfenozide and tebufenozide.

(19) Octopamine receptor agonists, for example amitraz.

(20) Mitochondrial complex III electron transport inhibitors, for example hydramethylnon or acequinocyl or fluacrypyrim.

(21) Mitochondrial complex I electron transport inhibitors, for example METI acaricides, e.g. fenazaquin, fenpyroximate, pyrimidifen, pyridaben, tebufenpyrad and tolfenpyrad or rotenone (Derris).

(22) Voltage-dependent sodium channel blockers, for example indoxacarb or metaflumizone.

(23) Inhibitors of acetyl CoA carboxylase, for example tetronic and tetramic acid derivatives, e.g. spirodiclofen, spiromesifen and spirotetramat.

(24) Mitochondrial complex IV electron transport inhibitors, for example phosphines, e.g. aluminium phosphide, calcium phosphide, phosphine and zinc phosphide, or cyanides, calcium cyanide, potassium cyanide and sodium cyanide.

(25) Mitochondrial complex II electron transport inhibitors, for example beta-keto nitrile derivatives, e.g. cyenopyrafen and cyflumetofen and carboxanilides, for example pyflubumide.

(28) Ryanodine receptor modulators, for example diamides, e.g. chlorantraniliprole, cyantraniliprole and flubendiamide, further active ingredients, for example afidopyropen, afoxolaner, azadirachtin, benclothiaz, benzoximate, bifenazate, broflanilide, bromopropylate, chinomethionat, chloroprallethrin, cryolite, cyclaniliprole, cycloxaprid, cyhalodiamide, dicloromezotiaz, dicofol, epsilon metofluthrin, epsilon momfluthrin, flometoquin, fluazaindolizine, fluensulfone, flufenerim, flufenoxystrobin, flufiprole, fluhexafon, fluopyram, fluralaner, fluxametamide, fufenozide, guadipyr, heptafluthrin, imidaclothiz, iprodione, kappa bifenthrin, kappa tefluthrin, lotilaner, meperfluthrin, paichongding, pyridalyl, pyrifluquinazon, pyriminostrobin, spirobudiclofen, tetramethylfluthrin, tetraniliprole, tetrachlorantraniliprole, tioxazafen, thiofluoximate, triflumezopyrim and iodomethane; additionally preparations based on *Bacillus firmus* (1-1582, BioNeem, Votivo), and the following compounds: 1-{2-fluoro-4-methyl-5-[(2,2,2-trifluoroethyl)sulfinyl]phenyl}-3-(trifluoromethyl)-1H-1,2,4-triazole-5-amine (known from WO2006/043635) (CAS 885026-50-6), {1'-[(2E)-3-(4-chlorophenyl)prop-2-en-1-yl]-5-fluorospiro[indole-3,4'-piperidine]-1(2H)-yl}(2-chloropyridin-4-yl) methanone (known from WO2003/106457) (CAS 637360-23-7), 2-chloro-N-[2-{1-[(2E)-3-(4-chlorophenyl)prop-2-en-1-yl]piperidin-4-yl}-4-(trifluoromethyl)phenyl] isonicotinamide (known from WO2006/003494) (CAS 872999-66-1), 3-(4-chloro-2,6-dimethylphenyl)-4-hydroxy-8-methoxy-1,8-diazaspiro[4.5]dec-3-en-2-one (known from WO 2010052161) (CAS 1225292-17-0), 3-(4-chloro-2,6-dimethylphenyl)-8-methoxy-2-oxo-1,8-diazaspiro[4.5]dec-3-en-4-yl ethylcarbonate (known from EP 2647626) (CAS-1440516-42-6), 4-(but-2-yn-1-yloxy)-6-(3,5-dimethylpiperidin-1-yl)-5-fluoropyrimidine (known from WO2004/099160) (CAS 792914-58-0), PF1364 (known from JP2010/018586) (CAS Reg. No. 1204776-60-2), N-[(2E)-1-[(6-chloropyridin-3-yl)methyl]pyridin-2(1H)-ylidene]-2,2,2-trifluoroacetamide (known from WO2012/029672) (CAS 1363400-41-2), (3E)-3-[1-[(6-chloro-3-pyridyl)methyl]-2-pyridylidene]-1,1,1-trifluoropropan-2-one (known from WO2013/144213) (CAS 1461743-15-6), N-[3-(benzylcarbamoyl)-4-chlorophenyl]-1-methyl-3-(pentafluoroethyl)-4-(trifluoromethyl)-1H-pyrazole-5-carboxamide (known from WO2010/051926) (CAS 1226889-14-0), 5-bromo-4-chloro-N-[4-chloro-2-methyl-6-(methylcarbamoyl)phenyl]-2-(3-chloro-2-pyridyl)pyrazole-3-carboxamide (known from CN103232431) (CAS 1449220-44-3), 4-[5-(3,5-dichlorophenyl)-4,5-dihydro-5-(trifluoromethyl)-3-isoxazolyl]-2-methyl-N-(cis-1-oxido-3-thietanyl)benzamide, 4-[5-(3,5-dichlorophenyl)-4,5-dihydro-5-(trifluoromethyl)-3-isoxazolyl]-2-methyl-N-(trans-1-oxido-3-thietanyl)benzamide and 4-[(5S)-5-(3,5-dichlorophenyl)-4,5-dihydro-5-(trifluoromethyl)-3-isoxazolyl]-2-methyl-N-(cis-1-oxido-3-thietanyl)benzamide (known from WO 2013/050317 A1) (CAS 1332628-83-7), N-[3-chloro-1-(3-pyridinyl)-1H-pyrazol-4-yl]-N-ethyl-3-[(3,3,3-trifluoropropyl)sulfinyl]propanamide, (+)-N-[3-chloro-1-(3-pyridinyl)-1H-pyrazol-4-yl]-N-ethyl-3-[(3,3,3-trifluoropropyl)sulfinyl]propanamide and (−)-N-[3-chloro-1-(3-pyridinyl)-1H-pyrazol-4-yl]-N-ethyl-3-[(3,3,3-trifluoropropyl)sulfinyl]propanamide (known from WO 2013/162715 A2, WO 2013/162716 A2, US 2014/0213448 A1) (CAS 1477923-37-7), 5-[[(2E)-3-chloro-2-propen-1-yl]amino]-1-[2,6-dichloro-4-(trifluoromethyl)phenyl]-4-[(trifluoromethyl)sulfinyl]-1H-pyrazole-3-carbonitrile (known from CN 101337937 A) (CAS 1105672-77-2), 3-bromo-N-[4-chloro-2-methyl-6-[(methylamino)thioxomethyl]phenyl]-1-(3-chloro-2-pyridinyl)-1H-pyrazole-5-carboxamide, (Liudaibenjiaxuanan, known from CN 103109816 A) (CAS 1232543-85-9); N-[4-chloro-2-[[(1,1-dimethylethyl)amino]carbonyl]-6-methylphenyl]-1-(3-chloro-2-pyridinyl)-3-(fluoromethoxy)-1H-pyrazole-5-carboxamide (known from WO 2012/034403 A1) (CAS 1268277-22-0), N-[2-(5-amino-1,3,4-thiadiazol-2-yl)-4-chloro-6-methylphenyl]-3-bromo-1-(3-chloro-2-pyridinyl)-1H-pyrazole-5-carboxamide (known from WO 2011/085575 A1) (CAS 1233882-22-8), 4-[3-[2,6-dichloro-4-[(3,3-dichloro-2-propen-1-yl)oxy]phenoxy]propoxy]-2-methoxy-6-(trifluoromethyl) pyrimidine (known from CN 101337940 A) (CAS 1108184-52-6); (2E)- and 2(Z)-2-[2-(4-cyanophenyl)-1-[3-(trifluoromethyl)phenyl]ethylidene]-N-[4-(difluoromethoxy)phenyl]hydrazinecarboxamide (known from CN 101715774 A) (CAS 1232543-85-9); cyclopropanecarboxylic acid 3-(2,2-dichloroethenyl)-2,2-dimethyl-4-(1H-benzimidazol-2-yl)phenyl ester (known from CN 103524422 A) (CAS 1542271-46-4); (4aS)-7-chloro-2,5-dihydro-2-[[(methoxy carbonyl) [4-[(trifluoromethyl)thio] phenyl]amino]carbonyl]indeno[1,2-e][1,3,4]oxadiazine-4a (3H)-carboxylic acid methyl ester (known from CN 102391261 A) (CAS 1370358-69-2); 6-deoxy-3-O-ethyl-2,4-di-O-methyl-1-[N-[4-[1-[4-(1,1,2,2,2-pentafluoroethoxy) phenyl]-1H-1,2,4-triazole-3-yl]phenyl]carbamate]-α-L-mannopyranose (known from US 2014/0275503 A1) (CAS 1181213-14-8); 8-(2-cyclopropylmethoxy-4-trifluoromethylphenoxy)-3-(6-trifluoromethylpyridazin-3-yl)-3-azabicyclo[3.2.1]octane (CAS 1253850-56-4), (8-anti)-8-(2-cyclopropylmethoxy-4-trifluoromethylphenoxy)-3-(6-trifluoromethylpyridazin-3-yl)-3-azabicyclo[3.2.1]octane (CAS 933798-27-7), (8-syn)-8-(2-cyclopropylmethoxy-4-trifluoromethylphenoxy)-3-(6-trifluoromethylpyridazin-3-yl)-3-azabicyclo[3.2.1]octane (known from WO 2007040280 A1, WO 2007040282 A1) (CAS 934001-66-8) and N-[3-chloro-1-(3-pyridinyl)-1H-pyrazol-4-yl]-N-ethyl-3-[(3,3,3-trifluoropropyl)thio]propanamide (known from WO 2015/058021 A1, WO 2015/058028 A1) (CAS 1477919-27-9).

Fungicides

The active ingredients specified herein by their common name are known and described, for example, in "Pesticide Manual" (16th Ed. British Crop Protection Council) or searchable on the internet (for example: http://www.alanwood.net/pesticides).

All the mixing components mentioned in classes (1) to (15), as the case may be, may form salts with suitable bases or acids if they are capable of doing so on the basis of their functional groups. All the fungicidal mixing components mentioned in classes (1) to (15), as the case may be, may include tautomeric forms.

1) Ergosterol biosynthesis inhibitors, for example (1.001) cyproconazole, (1.002) difenoconazole, (1.003) epoxiconazole, (1.004) fenhexamid, (1.005) fenpropidin, (1.006) fenpropimorph, (1.007) fenpyrazamine, (1.008) fluquinconazole, (1.009) flutriafol, (1.010) imazalil, (1.011) imazalil sulfate, (1.012) ipconazole, (1.013) metconazole, (1.014) myclobutanil, (1.015) paclobutrazol, (1.016) prochloraz, (1.017) propiconazole, (1.018) prothioconazole, (1.019) pyrisoxazole, (1.020) spiroxamine, (1.021) tebuconazole, (1.022) tetraconazole, (1.023) triadimenol, (1.024) tridemorph, (1.025) triticonazole, (1.026) (1R,2S,5S)-5-(4-chlorobenzyl)-2-(chloromethyl)-2-methyl-1-(1H-1,2,4-triazol-1-ylmethyl)cyclopentanol, (1.027) (1S,2R,5R)-5-(4-chlorobenzyl)-2-(chloromethyl)-2-methyl-1-(1H-1,2,4-triazol-1-ylmethyl)cyclopentanol, (1.028) (2R)-2-(1-chlorocyclopropyl)-4-[(1R)-2,2-dichlorocyclopropyl]-1-(1H-1,2,4-triazol-1-yl)butan-2-ol (1.029) (2R)-2-(1-chlorocyclopropyl)-4-[(1S)-2,2-dichlorocyclopropyl]-1-(1H-1,2,4-triazol-1-yl)butan-2-ol, (1.030) (2R)-2-[4-(4-chlorophenoxy)-2-(trifluoromethyl)phenyl]-1-(1H-1,2,4-triazol-1-yl)propan-2-ol, (1.031) (2S)-2-(1-chlorocyclopropyl)-4-[(1R)-2,2-dichlorocyclopropyl]-1-(1H-1,2,4-triazol-1-yl)butan-2-ol, (1.032) (2S)-2-(1-chlorocyclopropyl)-4-[(1S)-2,2-dichlorocyclopropyl]-1-(1H-1,2,4-triazol-1-yl)butan-2-ol, (1.033) (2S)-2-[4-(4-chlorophenoxy)-2-(trifluoromethyl)phenyl]-1-(1H-1,2,4-triazol-1-yl)propan-2-ol, (1.034) (R)-[3-(4-chloro-2-fluorophenyl)-5-(2,4-difluorophenyl)-1,2-oxazol-4-yl](pyridin-3-yl)methanol, (1.035) (S)-[3-(4-chloro-2-fluorophenyl)-5-(2,4-difluorophenyl)-1,2-oxazol-4-yl](pyridin-3-yl)methanol, (1.036) [3-(4-chloro-2-fluorophenyl)-5-(2,4-difluorophenyl)-1,2-oxazol-4-yl](pyridin-3-yl)methanol, (1.037) 1-({(2R,4S)-2-[2-chloro-4-(4-chlorophenoxy)phenyl]-4-methyl-1,3-dioxolan-2-yl}methyl)-1H-1,2,4-triazole, (1.038) 1-({(2S,4S)-2-[2-chloro-4-(4-chlorophenoxy)phenyl]-4-methyl-1,3-dioxolan-2-yl}methyl)-1H-1,2,4-triazole, (1.039) 1-{[3-(2-chlorophenyl)-2-(2,4-difluorophenyl)oxiran-2-yl]methyl}-1H-1,2,4-triazol-5-yl thiocyanate, (1.040) 1-{[rel(2R,3R)-3-(2-chlorophenyl)-2-(2,4-difluorophenyl)oxiran-2-yl]methyl}-1H-1,2,4-triazol-5-yl thiocyanate, (1.041) 1-{[rel(2R,3S)-3-(2-chlorophenyl)-2-(2,4-difluorophenyl)oxiran-2-yl]methyl}-1H-1,2,4-triazol-5-yl thiocyanate, (1.042) 2-[(2R,4R,5R)-1-(2,4-dichlorophenyl)-5-hydroxy-2,6,6-trimethylheptan-4-yl]-2,4-dihydro-3H-1,2,4-triazole-3-thione, (1.043) 2-[(2R,4R,5S)-1-(2,4-dichlorophenyl)-5-hydroxy-2,6,6-trimethylheptan-4-yl]-2,4-dihydro-3H-1,2,4-triazole-3-thione, (1.044) 2-[(2R,4S,5R)-1-(2,4-dichlorophenyl)-5-hydroxy-2,6,6-trimethylheptan-4-yl]-2,4-dihydro-3H-1,2,4-triazole-3-thione, (1.045) 2-[(2R,4S,5S)-1-(2,4-dichlorophenyl)-5-hydroxy-2,6,6-trimethylheptan-4-yl]-2,4-dihydro-3H-1,2,4-triazole-3-thione, (1.046) 2-[(2S,4R,5R)-1-(2,4-dichlorophenyl)-5-hydroxy-2,6,6-trimethylheptan-4-yl]-2,4-dihydro-3H-1,2,4-triazole-3-thione, (1.047) 2-[(2S,4R,5S)-1-(2,4-dichlorophenyl)-5-hydroxy-2,6,6-trimethylheptan-4-yl]-2,4-dihydro-3H-1,2,4-triazole-3-thione, (1.048) 2-[(2S,4S,5R)-1-(2,4-dichlorophenyl)-5-hydroxy-2,6,6-trimethylheptan-4-yl]-2,4-dihydro-3H-1,2,4-triazole-3-thione, (1.049) 2-[(2S,4S,5S)-1-(2,4-dichlorophenyl)-5-hydroxy-2,6,6-trimethylheptan-4-yl]-2,4-dihydro-3H-1,2,4-triazole-3-thione, (1.050) 2-[1-(2,4-dichlorophenyl)-5-hydroxy-2,6,6-trimethylheptan-4-yl]-2,4-dihydro-3H-1,2,4-triazole-3-thione, (1.051) 2-[2-chloro-4-(2,4-dichlorophenoxy)phenyl]-1-(1H-1,2,4-triazol-1-yl)propan-2-ol, (1.052) 2-[2-chloro-4-(4-chlorophenoxy)phenyl]-1-(1H-1,2,4-triazol-1-yl)butan-2-ol, (1.053) 2-[4-(4-chlorophenoxy)-2-(trifluoromethyl)phenyl]-1-(1H-1,2,4-triazol-1-yl)butan-2-ol, (1.054) 2-[4-(4-chlorophenoxy)-2-(trifluoromethyl)phenyl]-1-(1H-1,2,4-triazol-1-yl)pentan-2-ol, (1.055) 2-[4-(4-chlorophenoxy)-2-(trifluoromethyl)phenyl]-1-(1H-1,2,4-triazol-1-yl)propan-2-ol, (1.056) 2-{[3-(2-chlorophenyl)-2-(2,4-difluorophenyl)oxiran-2-yl]methyl}-2,4-dihydro-3H-1,2,4-triazole-3-thione, (1.057) 2-{[rel(2R,3R)-3-(2-chlorophenyl)-2-(2,4-difluorophenyl)oxiran-2-yl]methyl}-2,4-dihydro-3H-1,2,4-triazole-3-thione, (1.058) 2-{[rel(2R,3S)-3-(2-chlorophenyl)-2-(2,4-difluorophenyl)oxiran-2-yl]methyl}-2,4-dihydro-3H-1,2,4-triazole-3-thione, (1.059) 5-(4-chlorobenzyl)-2-(chloromethyl)-2-methyl-1-(1H-1,2,4-triazol-1-ylmethyl)cyclopentanol, (1.060) 5-(allylsulfanyl)-1-{[3-(2-chlorophenyl)-2-(2,4-difluorophenyl)oxiran-2-yl]methyl}-1H-1,2,4-triazole, (1.061) 5-(allylsulfanyl)-1-{[rel(2R,3R)-3-(2-chlorophenyl)-2-(2,4-difluorophenyl)oxiran-2-yl]methyl}-1H-1,2,4-triazole, (1.062) 5-(allylsulfanyl)-1-{[rel(2R,3S)-3-(2-chlorophenyl)-2-(2,4-difluorophenyl)oxiran-2-yl]methyl}-1H-1,2,4-triazole, (1.063) N'-(2,5-dimethyl-4-{[3-(1,1,2,2-tetrafluoroethoxy)phenyl]sulfanyl}phenyl)-N-ethyl-N-methylimidoformamide, (1.064) N'-(2,5-dimethyl-4-{[3-(2,2,2-trifluoroethoxy)phenyl]sulfanyl}phenyl)-N-ethyl-N-methylimidoformamide, (1.065) N'-(2,5-dimethyl-4-{[3-(2,2,3,3-tetrafluoropropoxy)phenyl]sulfanyl}phenyl)-N-ethyl-N-methylimidoformamide, (1.066) N'-(2,5-dimethyl-4-{[3-(pentafluoroethoxy)phenyl]sulfanyl}phenyl)-N-ethyl-N-methylimidoformamide, (1.067) N'-(2,5-dimethyl-4-{3-[(1,1,2,2-tetrafluoroethyl)sulfanyl]phenoxy}phenyl)-N-ethyl-N-methylimidoformamide, (1.068) N'-(2,5-dimethyl-4-{3-[(2,2,2-trifluoroethyl)sulfanyl]phenoxy}phenyl)-N-ethyl-N-methylimidoformamide, (1.069) N'-(2,5-dimethyl-4-{3-[(2,2,3,3-tetrafluoropropyl)sulfanyl]phenoxy}phenyl)-N-ethyl-N-methylimidoformamide, (1.070) N'-(2,5-dimethyl-4-{3-[(pentafluoroethyl)sulfanyl]phenoxy}phenyl)-N-ethyl-N-methylimidoformamide, (1.071) N'-(2,5-dimethyl-4-phenoxyphenyl)-N-ethyl-N-methylimidoformamide, (1.072) N'-(4-{[3-(difluoromethoxy)phenyl]sulfanyl}-2,5-dimethylphenyl)-N-ethyl-N-methylimidoformamide, (1.073) N'-(4-{3-[(difluoromethyl)sulfanyl]phenoxy}-2,5-dimethylphenyl)-N-ethyl-N-methylimidoformamide, (1.074) N'-[5-bromo-6-(2,3-dihydro-1H-inden-2-yloxy)-2-methylpyridin-3-yl]-N-ethyl-N-methylimidoformamide, (1.075) N'-{4-[(4,5-dichloro-1,3-thiazol-2-yl)oxy]-2,5-dimethylphenyl}-N-ethyl-N-methylimidoformamide, (1.076) N'-{5-bromo-6-[(1R)-1-(3,5-difluorophenyl)ethoxy]-2-methylpyridin-3-yl}-N-ethyl-N-methylimidoformamide, (1.077) N'-{5-bromo-6-[(1S)-1-(3,5-difluorophenyl)ethoxy]-2-methylpyridin-3-yl}-N-ethyl-N-methylimidoformamide, (1.078) N'-{5-bromo-6-[(cis-4-isopropy lcyclohexyl)oxy]-2-methylpyridin-3-yl}-N-ethyl-N-methylimidoformamide, (1.079) N'-{5-bromo-6-[(trans-4-isopropylcyclohexyl)oxy]-2-methylpyridin-3-yl}-N-ethyl- N-methylimidoformamide, (1.080) N'-{5-bromo-6-[1-(3,5-difluorophenyl)ethoxy]-2-methylpyridin-3-yl}-N-ethyl-N-methylimidoformamide.

2) Inhibitors of the respiratory chain in complex I or II, for example (2.001) benzovindiflupyr, (2.002) bixafen, (2.003) boscalid, (2.004) carboxin, (2.005) fluopyram, (2.006) flutolanil, (2.007) fluxapyroxad, (2.008) furametpyr, (2.009) isofetamid, (2.010) isopyrazam (anti-epimeric enantiomer 1R,4S,9S), (2.011) isopyrazam (anti-epimeric enantiomer 1S,4R,9R), (2.012) isopyrazam (anti-epimeric racemate 1RS,4SR,9SR), (2.013) isopyrazam (mixture of the syn-epimeric racemate 1RS,4SR,9RS and the anti-epimeric racemate 1RS,4SR,9SR), (2.014) isopyrazam (syn-epimeric enantiomer 1R,4S,9R), (2.015) isopyrazam (syn-epimeric enantiomer 1S,4R,9S), (2.016) isopyrazam (syn-epimeric racemate 1RS,4SR,9RS), (2.017) penflufen, (2.018) penthiopyrad, (2.019) pydiflumetofen, (2.020) pyraziflumid, (2.021) sedaxane, (2.022) 1,3-dimethyl-N-(1,1,3-trimethyl-2,3-dihydro-1H-inden-4-yl)-1H-pyrazole-4-carboxamide, (2.023) 1,3-dimethyl-N-[(3R)-1,1,3-trimethyl-2,3-dihydro-1H-inden-4-yl]-1H-pyrazole-4-carboxamide, (2.024) 1,3-dimethyl-N-[(3S)-1,1,3-trimethyl-2,3-dihydro-1H-inden-4-yl]-1H-pyrazole-4-carboxamide, (2.025) 1-methyl-3-(trifluoromethyl)-N-[2'-(trifluoromethyl)biphenyl-2-yl]-1H-pyrazole-4-carboxamide, (2.026) 2-fluoro-6-(trifluoromethyl)-N-(1,1,3-trimethyl-2,3-dihydro-1H-inden-4-yl)benzamide, (2.027) 3-(difluoromethyl)-1-methyl-N-(1,1,3-trimethyl-2,3-dihydro-1H-inden-4-yl)-1H-pyrazole-4-carboxamide, (2.028) 3-(difluoromethyl)-1-methyl-N-[(3R)-1,1,3-trimethyl-2,3-dihydro-1H-inden-4-yl]-1H-pyrazole-4-carboxamide, (2.029) 3-(difluoromethyl)-1-methyl-N-[(3S)-1,1,3-trimethyl-2,3-dihydro-1H-inden-4-yl]-1H-pyrazole-4-carboxamide, (2.030) 3-(difluoromethyl)-N-(7-fluoro-1,1,3-trimethyl-2,3-dihydro-1H-inden-4-yl)-1-methyl-1H-pyrazole-4-carboxamide, (2.031) 3-(difluoromethyl)-N-[(3R)-7-fluoro-1,1,3-trimethyl-2,3-dihydro-1H-inden-4-yl]-1-methyl-1H-pyrazole-4-carboxamide, (2.032) 3-(difluoromethyl)-N-[(3S)-7-fluoro-1,1,3-trimethyl-2,3-dihydro-1H-inden-4-yl]-1-methyl-1H-pyrazole-4-carboxamide, (2.033) 5,8-difluoro-N-[2-(2-fluoro-4-{[4-(trifluoromethyl)pyridin-2-yl]oxy}phenyl)ethyl]quinazolin-4-amine, (2.034) N-(2-cyclopentyl-5-fluorobenzyl)-N-cyclopropyl-3-(difluoromethyl)-5-fluoro-1-methyl-1H-pyrazole-4-carboxamide, (2.035) N-(2-tert-butyl-5-methylbenzyl)-N-cyclopropyl-3-(difluoromethyl)-5-fluoro-1-methyl-1H-pyrazole-4-carboxamide, (2.036) N-(2-tert-butylbenzyl)-N-cyclopropyl-3-(difluoromethyl)-5-fluoro-1-methyl-1H-pyrazole-4-carboxamide, (2.037) N-(5-chloro-2-ethylbenzyl)-N-cyclopropyl-3-(difluoromethyl)-5-fluoro-1-methyl-1H-pyrazole-4-carboxamide, (2.038) N-(5-chloro-2-isopropylbenzyl)-N-cyclopropyl-3-(difluoromethyl)-5-fluoro-1-methyl-1H-pyrazole-4-carboxamide, (2.039) N-[(1R,4S)-9-(dichloromethylene)-1,2,3,4-tetrahydro-1,4-methanonaphthalen-5-yl]-3-(difluoromethyl)-1-methyl-1H-pyrazole-4-carboxamide, (2.040) N-[(1S,4R)-9-(dichloromethylene)-1,2,3,4-tetrahydro-1,4-methanonaphthalen-5-yl]-3-(difluoromethyl)-1-methyl-1H-pyrazole-4-carboxamide, (2.041) N-[1-(2,4-dichlorophenyl)-1-methoxypropan-2-yl]-3-(difluoromethyl)-1-methyl-1H-pyrazole-4-carboxamide, (2.042) N-[2-chloro-6-(trifluoromethyl)benzyl]-N-cyclopropyl-3-(difluoromethyl)-5-fluoro-1-methyl-1H-pyrazole-4-carboxamide, (2.043) N-[3-chloro-2-fluoro-6-(trifluoromethyl)benzyl]-N-cyclopropyl-3-(difluoromethyl)-5-fluoro-1-methyl-1H-pyrazole-4-carboxamide, (2.044) N-[5-chloro-2-(trifluoromethyl)benzyl]-N-cyclopropyl-3-(difluoromethyl)-5-fluoro-1-methyl-1H-pyrazole-4-carboxamide, (2.045) N-cyclopropyl-3-(difluoromethyl)-5-fluoro-1-methyl-N-[5-methyl-2-(trifluoromethyl)benzyl]-1H-pyrazole-4-carboxamide, (2.046) N-cyclopropyl-3-(difluoromethyl)-5-fluoro-N-(2-fluoro-6-isopropylbenzyl)-1-methyl-1H-pyrazole-4-carboxamide, (2.047) N-cyclopropyl-3-(difluoromethyl)-5-fluoro-N-(2-isopropyl-5-methylbenzyl)-1-methyl-1H-pyrazole-4-carboxamide, (2.048) N-cyclopropyl-3-(difluoromethyl)-5-fluoro-N-(2-isopropylbenzyl)-1-methyl-1H-pyrazole-4-carbothioamide, (2.049) N-cyclopropyl-3-(difluoromethyl)-5-fluoro-N-(2-isopropylbenzyl)-1-methyl-1H-pyrazole-4-carboxamide, (2.050) N-cyclopropyl-3-(difluoromethyl)-5-fluoro-N-(5-fluoro-2-isopropylbenzyl)-1-methyl-1H-pyrazole-4-carboxamide, (2.051) N-cyclopropyl-3-(difluoromethyl)-N-(2-ethyl-4,5-dimethylbenzyl)-5-fluoro-1-methyl-1H-pyrazole-4-carboxamide, (2.052) N-cyclopropyl-3-(difluoromethyl)-N-(2-ethyl-5-fluorobenzyl)-5-fluoro-1-methyl-1H-pyrazole-4-carboxamide, (2.053) N-cyclopropyl-3-(difluoromethyl)-N-(2-ethyl-5-methylbenzyl)-5-fluoro-1-methyl-1H-pyrazole-4-carboxamide, (2.054) N-cyclopropyl-N-(2-cyclopropyl-5-fluorobenzyl)-3-(difluoromethyl)-5-fluoro-1-methyl-1H-pyrazole-4-carboxamide, (2.055) N-cyclopropyl-N-(2-cyclopropyl-5-methylbenzyl)-3-(difluoromethyl)-5-fluoro-1-methyl-1H-pyrazole-4-carboxamide, (2.056) N-cyclopropyl-N-(2-cyclopropylbenzyl)-3-(difluoromethyl)-5-fluoro-1-methyl-1H-pyrazole-4-carboxamide.

3) Inhibitors of the respiratory chain in complex III, for example (3.001) ametoctradin, (3.002) amisulbrom, (3.003) azoxystrobin, (3.004) coumethoxystrobin, (3.005) coumoxystrobin, (3.006) cyazofamid, (3.007) dimoxystrobin, (3.008) enoxastrobin, (3.009) famoxadon, (3.010) fenamidon, (3.011) flufenoxystrobin, (3.012) fluoxastrobin, (3.013) kresoxim-methyl, (3.014) metominostrobin, (3.015) orysastrobin, (3.016) picoxystrobin, (3.017) pyraclostrobin, (3.018) pyrametostrobin, (3.019) pyraoxystrobin, (3.020) trifloxystrobin (3.021) (2E)-2-{2-[({[(1E)-1-(3-{[(E)-1-fluoro-2-phenylvinyl]oxy}phenyl)ethylidene]amino}oxy)methyl]phenyl}-2-(methoxyimino)-N-methylacetamide, (3.022) (2E,3Z)-5-{[1-(4-chlorophenyl)-1H-pyrazol-3-yl]oxy}-2-(methoxyimino)-N,3-dimethylpent-3-enamide, (3.023) (2R)-2-{2-[(2,5-dimethylphenoxy)methyl]phenyl}-2-methoxy-N-methylacetamide, (3.024) (2S)-2-{2-[(2,5-dimethylphenoxy)methyl]phenyl}-2-methoxy-N-methylacetamide, (3.025) (3 S,6S,7R,8R)-8-benzyl-3-[({3-[(isobutyryloxy)methoxy]-4-methoxypyridin-2-yl}carbonyl)amino]-6-methyl-4,9-dioxo-1,5-dioxonan-7-yl 2-methylpropanoate, (3.026) 2-{2-[(2,5-dimethylphenoxy)methyl]phenyl}-2-methoxy-N-methylacetamide, (3.027) N-(3-ethyl-3,5,5-trimethylcyclohexyl)-3-formamido-2-hydroxybenzamide, (3.028) (2E,3Z)-5-{[1-(4-chloro-2-fluorophenyl)-1H-pyrazol-3-yl]oxy}-2-(methoxyimino)-N,3-dimethylpent-3-enamide.

4) Mitosis and cell division inhibitors, for example (4.001) carbendazim, (4.002) diethofencarb, (4.003) ethaboxam, (4.004) fluopicolid, (4.005) pencycuron, (4.006) thiabendazole, (4.007) thiophanate-methyl, (4.008) zoxamide, (4.009) 3-chloro-4-(2,6-difluorophenyl)-6-methyl-5-phenylpyridazine, (4.010) 3-chloro-5-(4-chlorophenyl)-4-(2,6-difluorophenyl)-6-methylpyridazine, (4.011) 3-chloro-5-(6-chloropyridin-3-yl)-6-methyl-4-(2,4,6-trifluorophenyl)pyridazine, (4.012) 4-(2-bromo-4-fluorophenyl)-N-(2,6-difluorophenyl)-1,3-dimethyl-1H-pyrazol-5-amine, (4.013) 4-(2-bromo-4-fluorophenyl)-N-(2-bromo-6-fluorophenyl)-1,3-dimethyl-1H-pyrazol-5-amine, (4.014) 4-(2-bromo-4-fluorophenyl)-N-(2-bromophenyl)-1,3-dimethyl-1H-pyrazol-5-amine, (4.015) 4-(2-bromo-4-fluorophenyl)-N-(2- chloro-6-fluorophenyl)-1,3-dimethyl-1H-pyrazol-5-amine, (4.016) 4-(2-bromo-4-fluorophenyl)-N-(2-chlorophenyl)-1,3-dimethyl-1H-pyrazol-5-amine, (4.017) 4-(2-bromo-4-fluorophenyl)-N-(2-fluorophenyl)-1,3-dimethyl-1H-pyrazol-5-amine, (4.018) 4-(2-chloro-4-fluorophenyl)-N-(2,6-difluorophenyl)-1,3-dimethyl-1H-pyrazol-5-amine, (4.019) 4-(2-chloro-4-fluorophenyl)-N-(2-chloro-6-fluorophenyl)-1,3-dimethyl-1H-pyrazol-5-amine, (4.020) 4-(2-chloro-4-fluorophenyl)-N-(2-chlorophenyl)-1,3-dimethyl-1H-pyrazol-5-amine, (4.021) 4-(2-chloro-4-fluorophenyl)-N-(2-fluorophenyl)-1,3-dimethyl-1H-pyrazol-5-amine, (4.022) 4-(4-chlorophenyl)-5-(2,6-difluorophenyl)-3,6-dimethyl-pyridazine, (4.023) N-(2-bromo-6-fluorophenyl)-4-(2-chloro-4-fluorophenyl)-1,3-dimethyl-1H-pyrazol-5-amine, (4.024) N-(2-bromophenyl)-4-(2-chloro-4-fluorophenyl)-1,3-dimethyl-1H-pyrazol-5-amine, (4.025) N-(4-chloro-2,6-difluorophenyl)-4-(2-chloro-4-fluorophenyl)-1,3-dimethyl-1H-pyrazol-5-amine.

5) Compounds having capacity for multisite activity, for example (5.001) Bordeaux mixture, (5.002) captafol, (5.003) captan, (5.004) chlorthalonil, (5.005) copper hydroxide, (5.006) copper naphthenate, (5.007) copper oxide, (5.008) copper oxychloride, (5.009) copper(2+) sulfate, (5.010) dithianon, (5.011) dodin, (5.012) folpet, (5.013) mancozeb, (5.014) maneb, (5.015) metiram, (5.016) zinc metiram, (5.017) copper oxine, (5.018) propineb, (5.019) sulfur and sulfur preparations including calcium polysulfide, (5.020) thiram, (5.021) zineb, (5.022) ziram.

6) Compounds capable of triggering host defence, for example (6.001) acibenzolar-S-methyl, (6.002) isotianil, (6.003) probenazole, (6.004) tiadinil.

7) Amino acid and/or protein biosynthesis inhibitors, for example (7.001) cyprodinil, (7.002) kasugamycin, (7.003) kasugamycin hydrochloride hydrate, (7.004) oxytetracycline, (7.005) pyrimethanil, (7.006) 3-(5-fluoro-3,3,4,4-tetramethyl-3,4-dihydroisoquinolin-1-yl)quinoline.

(8) ATP production inhibitors, for example (8.001) silthiofam.

9) Cell wall synthesis inhibitors, for example (9.001) benthiavalicarb, (9.002) dimethomorph, (9.003) flumorph, (9.004) iprovalicarb, (9.005) mandipropamid, (9.006) pyrimorph, (9.007) valifenalate, (9.008) (2E)-3-(4-tert-butylphenyl)-3-(2-chloropyridin-4-yl)-1-(morpholin-4-yl)prop-2-en-1-one, (9.009) (2Z)-3-(4-tert-butylphenyl)-3-(2-chloropyridin-4-yl)-1-(morpholin-4-yl)prop-2-en-1-one.

10) Lipid and membrane synthesis inhibitors, for example (10.001) propamocarb, (10.002) propamocarb hydrochloride, (10.003) tolclofos-methyl.

11) Melanin biosynthesis inhibitors, for example (11.001) tricyclazole, (11.002) 2,2,2-trifluoroethyl {3-methyl-1-[(4-methylbenzoyl)amino]butan-2-yl}carbamate.

12) Nucleic acid synthesis inhibitors, for example (12.001) benalaxyl, (12.002) benalaxyl-M (kiralaxyl), (12.003) metalaxyl, (12.004) metalaxyl-M (mefenoxam).

13) Signal transduction inhibitors, for example (13.001) fludioxonil, (13.002) iprodione, (13.003) procymidone, (13.004) proquinazid, (13.005) quinoxyfen, (13.006) vinclozolin.

14) Compounds that can act as uncouplers, for example (14.001) fluazinam, (14.002) meptyldinocap.

15) Further compounds, for example (15.001) abscisic acid, (15.002) benthiazole, (15.003) bethoxazin, (15.004) capsimycin, (15.005) carvone, (15.006) chinomethionat, (15.007) cufraneb, (15.008) cyflufenamid, (15.009) cymoxanil, (15.010) cyprosulfamide, (15.011) flutianil, (15.012) fosetyl-aluminium, (15.013) fosetyl-calcium, (15.014) fosetyl-sodium, (15.015) methyl isothiocyanate, (15.016) metrafenon, (15.017) mildiomycin, (15.018) natamycin, (15.019) nickel dimethyldithiocarbamate, (15.020) nitrothal-isopropyl, (15.021) oxamocarb, (15.022) oxathiapiprolin, (15.023) oxyfenthiin, (15.024) pentachlorophenol and salts, (15.025) phosphonic acid and salts thereof, (15.026) propamocarb-fosetylate, (15.027) pyriofenone (chlazafenone) (15.028) tebufloquin, (15.029) tecloftalam, (15.030) tolnifanide, (15.031) 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.032) 1-(4-{4-[(5S)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.033) 2-(6-benzylpyridin-2-yl)quinazoline, (15.034) 2,6-dimethyl-1H,5H-[1,4]dithiino[2,3-c:5,6-c']dipyrrole-1,3,5,7(2H,6H)-tetrone, (15.035) 2-[3,5-bis(difluoromethyl)-1H-pyrazol-1-yl]-1-[4-(4-{5-[2-(prop-2-yn-1-yloxy)phenyl]-4,5-dihydro-1,2-oxazol-3-yl}-1,3-thiazol-2-yl)piperidin-1-yl]ethanone, (15.036) 2-[3,5-bis(difluoromethyl)-1H-pyrazol-1-yl]-1-[4-(4-{5-[2-chloro-6-(prop-2-yn-1-yloxy)phenyl]-4,5-dihydro-1,2-oxazol-3-yl}-1,3-thiazol-2-yl)piperidin-1-yl]ethanone, (15.037) 2-[3,5-bis(difluoromethyl)-1H-pyrazol-1-yl]-1-[4-(4-{5-[2-fluoro-6-(prop-2-yn-1-yloxy)phenyl]-4,5-dihydro-1,2-oxazol-3-yl}-1,3-thiazol-2-yl)piperidin-1-yl]ethanone, (15.038) 2-[6-(3-fluoro-4-methoxyphenyl)-5-methylpyridin-2-yl]quinazoline, (15.039) 2-{(5R)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate, (15.040) 2-{(5S)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate, (15.041) 2-{2-[(7,8-difluoro-2-methylquinolin-3-yl)oxy]-6-fluorophenyl}propan-2-ol, (15.042) 2-{2-fluoro-6-[(8-fluoro-2-methylquinolin-3-yl)oxy]phenyl}propan-2-ol, (15.043) 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate, (15.044) 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}phenyl methanesulfonate, (15.045) 2-phenylphenol and salts thereof, (15.046) 3-(4,4,5-trifluoro-3,3-dimethyl-3,4-dihydroisoquinolin-1-yl)quinoline, (15.047) 3-(4,4-difluoro-3,3-dimethyl-3,4-dihydroisoquinolin-1-yl)quinoline, (15.048) 4-amino-5-fluoropyrimidin-2-ol (tautomeric form: 4-amino-5-fluoropyrimidin-2(1H)-one), (15.049) 4-oxo-4-[(2-phenylethyl)amino]butyric acid, (15.050) 5-amino-1,3,4-thiadiazole-2-thiol, (15.051) 5-chloro-N'-phenyl-N'-(prop-2-yn-1-yl)thiophene 2-sulfonohydrazide, (15.052) 5-fluoro-2-[(4-fluorobenzyl)oxy]pyrimidin-4-amine, (15.053) 5-fluoro-2-[(4-methylbenzyl)oxy]pyrimidin-4-amine, (15.054) 9-fluoro-2,2-dimethyl-5-(quinolin-3-yl)-2,3-dihydro-1,4-benzoxazepine, (15.055) but-3-yn-1-yl {6-[({[(Z)-(1-methyl-1H-tetrazol-5-yl)(phenyl)methylene]amino}oxy)methyl]pyridin-2-yl}carbamate, (15.056) ethyl (2Z)-3-amino-2-cyano-3-phenylacrylate, (15.057) phenazine-1-carboxylic acid, (15.058) propyl 3,4,5-trihydroxybenzoate, (15.059) quinolin-8-ol, (15.060) quinolin-8-ol sulfate (2:1), (15.061) tert-butyl {6-[({[(1-methyl-1H-tetrazol-5-yl)(phenyl)methylene]amino}oxy)methyl]pyridin-2-yl}carbamate.

Biological Pesticides as Mixing Components

The compounds of the formula (I) can be combined with biological pesticides.

Biological pesticides especially include bacteria, fungi, yeasts, plant extracts and products formed by microorganisms, including proteins and secondary metabolites.

Biological pesticides include bacteria such as spore-forming bacteria, root-colonizing bacteria and bacteria which act as biological insecticides, fungicides or nematicides.

Examples of such bacteria which are used or can be used as biological pesticides are:

*Bacillus amyloliquefaciens*, strain FZB42 (DSM 231179), or *Bacillus cereus*, especially *B. cereus* strain CNCM I-1562 or *Bacillus firmus*, strain I-1582 (Accession number CNCM I-1582) or *Bacillus pumilus*, especially strain GB34 (Accession No. ATCC 700814) and strain QST2808 (Accession No. NRRL B-30087), or *Bacillus subtilis*, especially strain GBO03 (Accession No. ATCC SD-1397), or *Bacillus subtilis* strain QST713 (Accession No. NRRL B-21661) or *Bacillus subtilis* strain OST 30002 (Accession No. NRRL B-50421), *Bacillus thuringiensis*, especially *B. thuringiensis* subspecies *israelensis* (serotype H-14), strain AM65-52 (Accession No. ATCC 1276), or *B. thuringiensis* subsp. *aizawai*, especially strain ABTS-1857 (SD-1372), or *B. thuringiensis* subsp. *kurstaki* strain HD-1, or *B. thuringiensis* subsp. *tenebrionis* strain NB 176 (SD-5428), *Pasteuria penetrans*, *Pasteuria* spp. (*Rotylenchulus reniformis* nematode)-PR3 (Accession Number ATCC SD-5834), *Streptomyces microflavus* strain AQ6121 (=QRD 31.013, NRRL B-50550), *Streptomyces galbus* strain AQ 6047 (Accession Number NRRL 30232).

Examples of fungi and yeasts which are used or can be used as biological pesticides are:

*Beauveria bassiana*, in particular strain ATCC 74040, *Coniothyrium minitans*, in particular strain CON/M/91-8 (Accession No. DSM-9660), *Lecanicillium* spp., in particular strain HRO LEC 12, *Lecanicillium lecanii* (formerly known as *Verticillium lecanii*), in particular strain KV01, *Metarhizium anisopliae*, in particular strain F52 (DSM3884/ATCC 90448), *Metschnikowia fructicola*, in particular strain NRRL Y-30752, *Paecilomyces fumosoroseus* (new: *Isaria fumosorosea*), in particular strain IFPC 200613, or strain Apopka 97 (Accession No. ATCC 20874), *Paecilomyces lilacinus*, in particular *P. lilacinus* strain 251 (AGAL 89/030550), *Talaromyces flavus*, in particular strain V117b, *Trichoderma atroviride*, in particular strain SC1 (Accession Number CBS 122089), *Trichoderma harzianum*, in particular *T. harzianum rifai* T39 (Accession Number CNCM 1-952).

Examples of viruses which are used or can be used as biological pesticides are:

*Adoxophyes orana* (summer fruit *tortrix*) granulosis virus (GV), *Cydia pomonella* (codling moth) granulosis virus (GV), *Helicoverpa armigera* (cotton bollworm) nuclear polyhedrosis virus (NPV), *Spodoptera exigua* (beet armyworm) mNPV, *Spodoptera frugiperda* (fall armyworm) mNPV, *Spodoptera littoralis* (African cotton leafworm) NPV.

Also included are bacteria and fungi which are added as 'inoculant' to plants or plant parts or plant organs and which, by virtue of their particular properties, promote plant growth and plant health. Examples include:

*Agrobacterium* spp., *Azorhizobium caulinodans*, *Azospirillum* spp., *Azotobacter* spp., *Bradyrhizobium* spp., *Burkholderia* spp., insbesondere *Burkholderia cepacia* (ehemals bekannt als *Pseudomonas cepacia*), *Gigaspora* spp., oder *Gigaspora monosporum*, *Glomus* spp., *Laccaria* spp., *Lactobacillus buchneri*, *Paraglomus* spp., *Pisolithus tinctorus*, *Pseudomonas* spp., *Rhizobium* spp., insbesondere *Rhizobium trifolii*, *Rhizopogon* spp., *Scleroderma* spp., *Suillus* spp., *Streptomyces* spp.

Examples of plant extracts and products formed by microorganisms, including proteins and secondary metabolites, which are used or can be used as biological pesticides are:

*Allium sativum*, *Artemisia absinthium*, azadirachtin, Biokeeper WP, *Cassia nigricans*, *Celastrus angulatus*, *Chenopodium anthelminticum*, chitin, Armour-Zen, *Dryopteris filix-mas*, *Equisetum arvense*, Fortune Aza, Fungastop, Heads Up (*Chenopodium quinoa* saponin extract), pyrethrum/pyrethrins, *Quassia amara*, *Quercus*, Quillaja, Regalia, "Requiem™ Insecticide", rotenone, ryania/ryanodine, *Symphytum officinale*, *Tanacetum vulgare*, thymol, Triact 70, TriCon, *Tropaeulum majus*, *Urtica dioica*, Veratrin, *Viscum album*, Brassicaceae extract, especially oilseed rape powder or mustard powder.

Safener as Mixing Components

The compounds of the formula (I) can be combined with safeners, for example benoxacor, cloquintocet (-mexyl), cyometrinil, cyprosulfamide, dichlormid, fenchlorazole (-ethyl), fenclorim, flurazole, fluxofenim, furilazole, isoxadifen (-ethyl), mefenpyr (-diethyl), naphthalic anhydride, oxabetrinil, 2-methoxy-N-({4-[(methylcarbamoyl)amino]phenyl}sulfonyl)benzamide (CAS 129531-12-0), 4-(dichloroacetyl)-1-oxa-4-azaspiro[4.5]decane (CAS 71526-07-3), 2,2,5-trimethyl-3-(dichloroacetyl)-1,3-oxazolidine (CAS 52836-31-4).

Plants and Plant Parts

All plants and plant parts can be treated in accordance with the invention. Plants are understood here to mean all plants and populations of plants, such as desirable and undesirable wild plants or crop plants (including naturally occurring crop plants), for example cereals (wheat, rice, triticale, barley, rye, oats), maize, soya beans, potatoes, sugar beet, sugar cane, tomatoes, bell peppers, cucumbers, melons, carrots, water melons, onions, lettuce, spinach, leeks, beans, *Brassica oleracea* (e.g. cabbage) and other vegetable species, cotton, tobacco, oilseed rape, and also fruit plants (the fruits being apples, pears, citrus fruits and grapes). Crop plants may be plants which can be obtained by conventional breeding and optimization methods or by biotechnological and genetic engineering methods or combinations of these methods, including the transgenic plants and including the plant cultivars which are protectable or non-protectable by plant breeders' rights. Plants shall be understood to mean all development stages such as seed, seedlings, young (immature) plants, up to and including mature plants. Plant parts shall be understood to mean all parts and organs of the plants above and below ground, such as shoot, leaf, flower and root, examples given being leaves, needles, stalks, stems, flowers, fruit bodies, fruits and seeds, and also roots, tubers and rhizomes. Plant parts also include harvested plants or harvested plant parts and vegetative and generative propagation material, for example cuttings, tubers, rhizomes, slips and seeds.

The inventive treatment of the plants and parts of plants with the compounds of the formula (I) is effected directly or by allowing the compounds to act on the surroundings, the habitat or the storage space thereof by the customary treatment methods, for example by dipping, spraying, evaporating, fogging, scattering, painting on, injecting, and, in the case of propagation material, especially in the case of seeds, also by applying one or more coats.

As already mentioned above, it is possible to treat all plants and their parts in accordance with the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering methods, if appropriate in combination with conventional methods (genetically modified organisms), and parts thereof are treated. The term "parts" or "parts of plants" or "plant parts" has been explained above. Particular preference is given in accordance with the invention to treating plants of the respective commercially customary plant cultivars or those that are in use. Plant cultivars are understood to mean plants having new properties ("traits") and which have been obtained by conventional breeding, by mutagenesis or by recombinant DNA techniques. They may be cultivars, varieties, biotypes or genotypes.

Transgenic Plants, Seed Treatment and Integration Events

The preferred transgenic plants or plant cultivars (those obtained by genetic engineering) which are to be treated in accordance with the invention include all plants which, through the genetic modification, received genetic material which imparts particular advantageous useful properties ("traits") to these plants. Examples of such properties are better plant growth, increased tolerance to high or low temperatures, increased tolerance to drought or to levels of water or soil salinity, enhanced flowering performance, easier harvesting, accelerated ripening, higher harvest yields, higher quality and/or higher nutritional value of the harvested products, better capability for storage and/or processability of the harvested products. Further and particularly emphasized examples of such properties are increased resistance of the plants to animal and microbial pests, such as insects, arachnids, nematodes, mites, slugs and snails, owing, for example, to toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof), and also increased resistance of the plants to phytopathogenic fungi, bacteria and/or viruses caused, for example, by systemic acquired resistance (SAR), systemin, phytoalexins, elicitors and resistance genes and correspondingly expressed proteins and toxins, and also increased tolerance of the plants to certain active herbicidal compounds, for example imidazolinones, sulfonylureas, glyphosate or phosphinothricin (for example the "PAT" gene). The genes which impart the desired properties ("traits") in question may also be present in combinations with one another in the transgenic plants. Examples of transgenic plants mentioned include the important crop plants, such as cereals (wheat, rice, triticale, barley, rye, oats), maize, soya beans, potatoes, sugar beet, sugar cane, tomatoes, peas and other types of vegetable, cotton, tobacco, oilseed rape and also fruit plants (the fruits being apples, pears, citrus fruits and grapevines), particular emphasis being given to maize, soya beans, wheat, rice, potatoes, cotton, sugar cane, tobacco and oilseed rape. Properties ("traits") which are particularly emphasized are the increased resistance of the plants to insects, arachnids, nematodes and slugs and snails.

Crop Protection—Types of Treatment

The plants and plant parts are treated with the compounds of the formula (I) directly or by action on their surroundings, habitat or storage space using customary treatment methods, for example by dipping, spraying, atomizing, irrigating, evaporating, dusting, fogging, broadcasting, foaming, painting, spreading-on, injecting, watering (drenching), drip irrigating and, in the case of propagation material, in particular in the case of seed, additionally by dry seed treatment, liquid seed treatment, slurry treatment, by incrusting, by coating with one or more coats, etc. It is furthermore possible to apply the compounds of the formula (I) by the ultra-low volume method or to inject the application form or the compound of the formula (I) itself into the soil.

A preferred direct treatment of the plants is foliar application, meaning that the compounds of the formula (I) are applied to the foliage, in which case the treatment frequency and the application rate should be adjusted according to the level of infestation with the pest in question.

In the case of systemically active ingredients, the compounds of the formula (I) also access the plants via the root system. The plants are then treated by the action of the compounds of the formula (I) on the habitat of the plant. This can be accomplished, for example, by drenching, or by mixing into the soil or the nutrient solution, meaning that the locus of the plant (e.g. soil or hydroponic systems) is impregnated with a liquid form of the compounds of the formula (I), or by soil application, meaning that the compounds of the formula (I) according to the invention are introduced in solid form (e.g. in the form of granules) into the locus of the plants. In the case of paddy rice crops, this can also be accomplished by metering the compound of the formula (I) in a solid application form (for example as granules) into a flooded paddy field.

Seed Treatment

The control of animal pests by the treatment of the seed of plants has long been known and is the subject of constant improvements. Nevertheless, the treatment of seed entails a series of problems which cannot always be solved in a satisfactory manner. Thus, it is desirable to develop methods for protecting the seed and the germinating plant which dispense with, or at least reduce considerably, the additional application of pesticides during storage, after sowing or after emergence of the plants. It is additionally desirable to optimize the amount of active ingredient used so as to provide optimum protection for the seed and the germinating plant from attack by animal pests, but without damage to the plant itself by the active ingredient used. In particular, methods for the treatment of seed should also take account of the intrinsic insecticidal or nematicidal properties of pest-resistant or -tolerant transgenic plants in order to achieve optimal protection of the seed and also the germinating plant with a minimum expenditure on pesticides.

The present invention therefore in particular also relates to a method for the protection of seed and germinating plants from attack by pests, by treating the seed with one of the compounds of the formula (I). The method according to the invention for protecting seed and germinating plants against attack by pests further comprises a method in which the seed is treated simultaneously in one operation or sequentially with a compound of the formula (I) and a mixing component. It further also comprises a method where the seed is treated at different times with a compound of the formula (I) and a mixing component.

The invention also relates to the use of the compounds of the formula (I) for the treatment of seed for protecting the seed and the resulting plant from animal pests.

The invention further relates to seed which has been treated with a compound of the formula (I) according to the invention for protection from animal pests. The invention also relates to seed which has been treated simultaneously with a compound of the formula (I) and a mixing component. The invention further relates to seed which has been treated at different times with a compound of the formula (I) and a mixing component. In the case of seed which has been treated at different times with a compound of the formula (I)

and a mixing component, the individual substances may be present on the seed in different layers. In this case, the layers comprising a compound of the formula (I) and mixing components may optionally be separated by an intermediate layer. The invention also relates to seed in which a compound of the formula (I) and a mixing component have been applied as part of a coating or as a further layer or further layers in addition to a coating.

The invention further relates to seed which, after the treatment with a compound of the formula (I), is subjected to a film-coating process to prevent dust abrasion on the seed.

One of the advantages that occur when a compound of the formula (I) acts systemically is that the treatment of the seed protects not only the seed itself but also the plants resulting therefrom, after emergence, from animal pests. In this way, the immediate treatment of the crop at the time of sowing or shortly thereafter can be dispensed with.

A further advantage is that the treatment of the seed with a compound of the formula (I) can enhance germination and emergence of the treated seed.

It is likewise considered to be advantageous that compounds of the formula (I) can especially also be used for transgenic seed.

Furthermore, compounds of the formula (I) can be employed in combination with compositions of signalling technology, leading to better colonization by symbionts such as, for example, *rhizobia*, mycorrhizae and/or endophytic bacteria or fungi, and/or to optimized nitrogen fixation.

The compounds of the formula (I) are suitable for protection of seed of any plant variety which is used in agriculture, in the greenhouse, in forests or in horticulture. More particularly, this is the seed of cereals (for example wheat, barley, rye, millet and oats), maize, cotton, soya beans, rice, potatoes, sunflowers, coffee, tobacco, canola, oilseed rape, beets (for example sugar beets and fodder beets), peanuts, vegetables (for example tomatoes, cucumbers, beans, cruciferous vegetables, onions and lettuce), fruit plants, lawns and ornamental plants. Of particular significance is the treatment of the seed of cereals (such as wheat, barley, rye and oats), maize, soya beans, cotton, canola, oilseed rape, vegetables and rice.

As already mentioned above, the treatment of transgenic seed with a compound of the formula (I) is also of particular importance. This involves the seed of plants which generally contain at least one heterologous gene which controls the expression of a polypeptide having insecticidal and/or nematicidal properties in particular. The heterologous genes in transgenic seed may originate from microorganisms such as *Bacillus, Rhizobium, Pseudomonas, Serratia, Trichoderma, Clavibacter, Glomus* or *Gliocladium*. The present invention is particularly suitable for treatment of transgenic seed which comprises at least one heterologous gene originating from *Bacillus* sp. The heterologous gene is more preferably derived from *Bacillus thuringiensis*.

In the context of the present invention, the compound of the formula (I) is applied to the seed. The seed is preferably treated in a state in which it is sufficiently stable for no damage to occur in the course of treatment. In general, the seed can be treated at any time between harvest and sowing. It is customary to use seed which has been separated from the plant and freed from cobs, shells, stalks, coats, hairs or the flesh of the fruits. For example, it is possible to use seed which has been harvested, cleaned and dried down to a moisture content which allows storage. Alternatively, it is also possible to use seed which, after drying, has been treated with, for example, water and then dried again, for example priming. In the case of rice seed, it is also possible to use seed which has been soaked, for example in water, until it reaches a certain stage of the rice embryo ("pigeon breast stage") which results in stimulation of germination and more uniform emergence.

When treating the seed, care must generally be taken that the amount of the compound of the formula (I) applied to the seed and/or the amount of further additives is chosen in such a way that the germination of the seed is not adversely affected, or that the resulting plant is not damaged. This has to be ensured particularly in the case of active ingredients which can exhibit phytotoxic effects at certain application rates.

In general, the compounds of the formula (I) are applied to the seed in the form of a suitable formulation. Suitable formulations and processes for seed treatment are known to the person skilled in the art.

The compounds of the formula (I) can be converted to the customary seed-dressing formulations, such as solutions, emulsions, suspensions, powders, foams, slurries or other coating compositions for seed, and also ULV formulations.

These formulations are prepared in a known manner, by mixing the compounds of the formula (I) with customary additives, for example customary extenders and solvents or diluents, dyes, wetting agents, dispersants, emulsifiers, antifoams, preservatives, secondary thickeners, adhesives, gibberellins, and also water.

Dyes which may be present in the seed-dressing formulations usable in accordance with the invention are all dyes which are customary for such purposes. It is possible to use either pigments, which are sparingly soluble in water, or dyes, which are soluble in water. Examples include the dyes known by the names Rhodamine B, C.I. Pigment Red 112 and C.I. Solvent Red 1.

Useful wetting agents which may be present in the seed-dressing formulations usable in accordance with the invention are all substances which promote wetting and which are customary for the formulation of active agrochemical ingredients. Usable with preference are alkyl naphthalenesulfonates, such as diisopropyl or diisobutyl naphthalenesulfonates.

Suitable dispersants and/or emulsifiers which may be present in the seed-dressing formulations usable in accordance with the invention are all nonionic, anionic and cationic dispersants customary for the formulation of active agrochemical ingredients. Nonionic or anionic dispersants or mixtures of nonionic or anionic dispersants can be used with preference. Suitable nonionic dispersants especially include ethylene oxide/propylene oxide block polymers, alkylphenol polyglycol ethers and tristyrylphenol polyglycol ethers, and the phosphated or sulfated derivatives thereof. Suitable anionic dispersants are especially lignosulfonates, polyacrylic acid salts and arylsulfonate-formaldehyde condensates.

Antifoams which may be present in the seed-dressing formulations usable in accordance with the invention are all foam-inhibiting substances customary for the formulation of active agrochemical ingredients. Silicone antifoams and magnesium stearate can be used with preference.

Preservatives which may be present in the seed-dressing formulations usable in accordance with the invention are all substances usable for such purposes in agrochemical compositions. Examples include dichlorophene and benzyl alcohol hemiformal.

Secondary thickeners which may be present in the seed-dressing formulations usable in accordance with the invention are all substances which can be used for such purposes in agrochemical compositions. Preferred examples include cellulose derivatives, acrylic acid derivatives, xanthan, modified clays and finely divided silica.

Useful stickers which may be present in the seed-dressing formulations usable in accordance with the invention are all customary binders usable in seed-dressing products. Preferred examples include polyvinylpyrrolidone, polyvinyl acetate, polyvinyl alcohol and tylose.

Gibberellins which may be present in the seed-dressing formulations usable in accordance with the invention are preferably the gibberellins A1, A3 (=gibberellic acid), A4 and A7; particular preference is given to using gibberellic acid. The gibberellins are known (cf. R. Wegler "Chemie der Pflanzenschutz-und Schädlingsbekämpfungsmittel", vol. 2, Springer Verlag, 1970, pp. 401-412).

The seed-dressing formulations usable in accordance with the invention can be used to treat a wide variety of different kinds of seed, either directly or after prior dilution with water. For instance, the concentrates or the preparations obtainable therefrom by dilution with water can be used to dress the seed of cereals, such as wheat, barley, rye, oats and triticale, and also the seed of maize, rice, oilseed rape, peas, beans, cotton, sunflowers, soya beans and beets, or else a wide variety of different vegetable seed. The seed-dressing formulations usable in accordance with the invention, or the dilute use forms thereof, can also be used to dress seed of transgenic plants.

For the treatment of seed with the seed-dressing formulations usable in accordance with the invention, or the use forms prepared therefrom through the addition of water, all mixing units usable customarily for the seed dressing are useful. Specifically, the procedure in seed dressing is to place the seed into a mixer in batchwise or continuous operation, to add the particular desired amount of seed-dressing formulations, either as such or after prior dilution with water, and to mix until the formulation is distributed homogeneously on the seed. If appropriate, this is followed by a drying operation.

The application rate of the seed dressing formulations usable in accordance with the invention can be varied within a relatively wide range. It is guided by the particular content of the compounds of the formula (I) in the formulations and by the seed. The application rates of the compound of the formula (I) are generally between 0.001 and 50 g per kilogram of seed, preferably between 0.01 and 15 g per kilogram of seed.

Animal Health

In the animal health field, i.e. the field of veterinary medicine, the compounds of the formula (I) are active against animal parasites, in particular ectoparasites or endoparasites. The term "endoparasite" includes especially helminths and protozoa, such as coccidia. Ectoparasites are typically and preferably arthropods, especially insects or acarids.

In the field of veterinary medicine, the compounds of the formula (I) having favourable endotherm toxicity are suitable for controlling parasites which occur in animal breeding and animal husbandry in livestock, breeding animals, zoo animals, laboratory animals, experimental animals and domestic animals. They are active against all or specific stages of development of the parasites.

Agricultural livestock include, for example, mammals, such as sheep, goats, horses, donkeys, camels, buffalo, rabbits, reindeer, fallow deer and especially cattle and pigs; or poultry such as turkeys, ducks, geese and especially chickens; or fish or crustaceans, for example in aquaculture; or, as the case may be, insects such as bees.

Domestic animals include, for example, mammals, such as hamsters, guinea pigs, rats, mice, chinchillas, ferrets, and particularly dogs, cats, caged birds; reptiles, amphibians or aquarium fish.

In a specific embodiment, the compounds of the formula (I) are administered to mammals.

In another specific embodiment, the compounds of the formula (I) are administered to birds, namely caged birds or particularly poultry.

Use of the compounds of the formula (I) for the control of animal parasites is intended to reduce or prevent illness, cases of death and reductions in performance (in the case of meat, milk, wool, hides, eggs, honey and the like), such that more economical and simpler animal husbandry is enabled and better animal well-being is achievable.

In relation to the field of animal health, the term "control" or "controlling" in the present context means that the compounds of the formula (I) are effective in reducing the incidence of the particular parasite in an animal infected with such parasites to an innocuous degree. More specifically, "controlling" in the present context means that the compounds of the formula (I) kill the respective parasite, inhibit its growth, or inhibit its proliferation.

The arthropods include, for example, but are not limited to, from the order of Anoplurida, for example, *Haematopinus* spp., *Linognathus* spp., *Pediculus* spp., Phtirus spp. and *Solenopotes* spp.;

from the order of Mallophagida and the suborders Amblycerina and Ischnocerina, for example, *Bovicola* spp., *Damalina* spp., *Felicola* spp.; *Lepikentron* spp., *Menopon* spp., *Trichodectes* spp., *Trimenopon* spp., *Trinoton* spp., *Werneckiella* spp;

from the order of Diptera and the suborders Nematocerina and Brachycerina, for example, *Aedes* spp., *Anopheles* spp., *Atylotus* spp., *Braula* spp., *Calliphora* spp., *Chrysomyia* spp., *Chrysops* spp., *Culex* spp., *Culicoides* spp., *Eusimulium* spp., *Fannia* spp., *Gasterophilus* spp., *Glossina* spp., *Haematobia* spp., *Haematopota* spp., *Hippobosca* spp., *Hybomitra* spp., *Hydrotaea* spp., *Hypoderma* spp., *Lipoptena* spp., *Lucilia* spp., *Lutzomyia* spp., *Melophagus* spp., *Morellia* spp., *Musca* spp., *Odagmia* spp., *Oestrus* spp., *Philipomyia* spp., *Phlebotomus* spp., *Rhinoestrus* spp., *Sarcophaga* spp., *Simulium* spp., *Stomoxys* spp., *Tabanus* spp., *Tipula* spp., *Wilhelmia* spp., *Wohlfahrtia* spp.;

from the order of Siphonapterida, for example, *Ceratophyllus* spp., *Ctenocephalides* spp., *Pulex* spp., *Tunga* spp., *Xenopsylla* spp.;

from the order of heteropterida, for example, *Cimex* spp., *Panstrongylus* spp., *Rhodnius* spp., *Triatoma* spp.; and also nuisance and hygiene pests from the order Blattarida.

In addition, in the case of the arthropods, mention should be made by way of example, without limitation, of the following Acari:

from the subclass of Acari (Acarina) and the order of Metastigmata, for example from the family of Argasidae such as *Argas* spp., *Ornithodorus* spp., *Otobius* spp., from the family of Ixodidae such as *Amblyomma* spp., *Dermacentor* spp., *Haemaphysalis* spp., *Hyalomma* spp., *Ixodes* spp., *Rhipicephalus* (*Boophilus*) spp., *Rhipicephalus* spp. (the original genus of multi-host ticks); from the order of Mesostigmata such as *Dermanyssus* spp., *Ornithonyssus* spp., *Pneumonyssus* spp., *Raillietia* spp., *Sternostoma* spp., *Tropilaelaps* spp., *Varroa* spp.; from the order of the Actinedida (Prostigmata), for example, *Acarapis* spp., *Cheyletiella* spp., *Demodex* spp., *Listrophorus* spp., *Myobia* spp., *Neotrombicula* spp., *Ornithocheyletia* spp., *Psorergates* spp., *Trombicula* spp.; and from the order of the Acaridida (Astigmata), for example, *Acarus* spp., *Caloglyphus* spp., *Chorioptes* spp., *Cytodites* spp., *Hypodectes* spp., *Knemidocoptes* spp., *Laminosioptes* spp., *Notoedres* spp., *Otodectes* spp., *Psoroptes* spp., *Pterolichus* spp., *Sarcoptes* spp., *Trixacarus* spp., *Tyrophagus* spp.

Examples of parasitic protozoa include, but are not limited to:

Mastigophora (*Flagellata*), such as:

Metamonada: from the order of Diplomonadida, for example, *Giardia* spp., *Spironucleus* spp.

Parabasala: from the order of Trichomonadida, for example, *Histomonas* spp., *Pentatrichomonas* spp., *Tetratrichomonas* spp., *Trichomonas* spp., *Tritrichomonas* spp.

Euglenozoa: from the order of Trypanosomatida, for example, *Leishmania* spp., *Trypanosoma* spp.

Sarcomastigophora (Rhizopoda) such as Entamoebidae, for example, *Entamoeba* spp., Centramoebidae, for example *Acanthamoeba* sp., Euamoebidae, e.g. *Hartmanella* sp.

Alveolata such as Apicomplexa (Sporozoa): e.g. *Cryptosporidium* spp.; from the order of Eimeriida, for example, *Besnoitia* spp., *Cystoisospora* spp., *Eimeria* spp., *Hammondia* spp., *Isospora* spp., *Neospora* spp., *Sarcocystis* spp., *Toxoplasma* spp.; from the order of Adeleida, for example, *Hepatozoon* spp., *Klossiella* spp.; from the order of Haemosporida, for example, *Leucocytozoon* spp., *Plasmodium* spp.; from the order of Piroplasmida, for example, *Babesia* spp., *Ciliophora* spp., *Echinozoon* spp., *Theileria* spp.; from the order of Vesibuliferida, for example, *Balantidium* spp., *Buxtonella* spp.

*Microspora* such as *Encephalitozoon* spp., *Enterocytozoon* spp., *Globidium* spp., *Nosema* spp., and also, for example, *Myxozoa* spp.

The helminths that are pathogenic to humans or animals include, for example, Acanthocephala, nematodes, Pentastoma and Platyhelminthes (e.g. Monogenea, cestodes and trematodes).

Illustrative helminths include, but are not limited to:

Monogenea: e.g. *Dactylogyrus* spp., *Gyrodactylus* spp., *Microbothrium* spp., *Polystoma* spp., *Troglecephalus* spp.;

Cestodes: from the order of Pseudophyllidea, for example: *Bothridium* spp., *Diphyllobothrium* spp., *Diplogonoporus* spp., *Ichthyobothrium* spp., *Ligula* spp., *Schistocephalus* spp., *Spirometra* spp.

From the order of cyclophyllida, for example: *Andyra* spp., *Anoplocephala* spp., *Avitellina* spp., *Bertiella* spp., *Cittotaenia* spp., *Davainea* spp., *Diorchis* spp., *Diplopylidium* spp., *Dipylidium* spp., *Echinococcus* spp., *Echinocotyle* spp., *Echinolepis* spp., *Hydatigera* spp., *Hymenolepis* spp., *Joyeuxiella* spp., *Mesocestoides* spp., *Moniezia* spp., *Paranoplocephala* spp., *Raillietina* spp., *Stilesia* spp., *Taenia* spp., *Thysaniezia* spp., *Thysanosoma* spp.

Trematodes: from the class of Digenea, for example: *Austrobilharzia* spp., *Brachylaima* spp., *Calicophoron* spp., *Catatropis* spp., *Clonorchis* spp. *Collyriclum* spp., *Cotylophoron* spp., *Cyclocoelum* spp., *Dicrocoelium* spp., *Diplostomum* spp., *Echinochasmus* spp., *Echinoparyphium* spp., *Echinostoma* spp., *Eurytrema* spp., *Fasciola* spp., *Fasciolides* spp., *Fasciolopsis* spp., *Fischoederius* spp., *Gastrothylacus* spp., *Gigantobilharzia* spp., *Gigantocotyle* spp., *Heterophyes* spp., *Hypoderaeum* spp., *Leucochloridium* spp., *Metagonimus* spp., *Metorchis* spp., *Nanophyetus* spp., *Notocotylus* spp., *Opisthorchis* spp., *Ornithobilharzia* spp., *Paragonimus* spp., *Paramphistomum* spp., *Plagiorchis* spp., *Posthodiplostomum* spp., *Prosthogonimus* spp., *Schistosoma* spp., *Trichobilharzia* spp., *Troglotrema* spp., *Typhlocoelum* spp.

Nematodes: from the order of Trichinellida, for example: *Capillaria* spp., *Trichinella* spp., *Trichomosoides* spp., *Trichuris* spp.

From the order of Tylenchida, for example: *Micronema* spp., *Parastrangyloides* spp., *Strongyloides* spp.

From the order of Rhabditina, for example: *Aelurostrongylus* spp., *Amidostomum* spp., *Ancylostoma* spp., *Angiostrongylus* spp., *Bronchonema* spp., *Bunostomum* spp., *Chabertia* spp., *Cooperia* spp., *Cooperioides* spp., *Crenosoma* spp., *Cyathostomum* spp., *Cyclococercus* spp., *Cyclodontostomum* spp., *Cylicocyclus* spp., *Cylicostephanus* spp., *Cylindropharynx* spp., *Cystocaulus* spp., *Dictyocaulus* spp., *Elaphostrongylus* spp., *Filaroides* spp., *Globocephalus* spp., *Graphidium* spp., *Gyalocephalus* spp., *Haemonchus* spp., *Heligmosomoides* spp., *Hyostrongylus* spp., *Marshallagia* spp., *Metastrongylus* spp., *Muellerius* spp., *Necator* spp., *Nematodirus* spp., *Neostrongylus* spp., *Nippostrongylus* spp., *Obeliscoides* spp., *Oesophagodontus* spp., *Oesophagostomum* spp., *Ollulanus* spp.; *Ornithostrongylus* spp., *Oslerus* spp., *Ostertagia* spp., *Paracooperia* spp., *Paracrenosoma* spp., *Parafilaroides* spp., *Parelaphostrongylus* spp., *Pneumocaulus* spp., *Pneumostrongylus* spp., *Poteriostomum* spp., *Protostrongylus* spp., *Spicocaulus* spp., *Stephanurus* spp., *Strongylus* spp., *Syngamus* spp., *Teladorsagia* spp., *Trichonema* spp., *Trichostrongylus* spp., *Triodontophorus* spp., *Troglostrongylus* spp., *Uncinaria* spp.

From the order of Spirurida, for example: *Acanthocheilonema* spp., *Anisakis* spp., *Ascaridia* spp.; *Ascaris* spp., *Ascarops* spp., *Aspiculuris* spp., *Baylisascaris* spp., *Brugia* spp., *Cercopithifilaria* spp., *Crassicauda* spp., *Dipetalonema* spp., *Dirofilaria* spp., *Dracunculus* spp.; *Draschia* spp., *Enterobius* spp., *Filaria* spp., *Gnathostoma* spp., *Gongylonema* spp., *Habronema* spp., *Heterakis* spp.; *Litomosoides* spp., *Loa* spp., *Onchocerca* spp., *Oxyuris* spp., *Parabronema* spp., *Parafilaria* spp., *Parascaris* spp., *Passalurus* spp., *Physaloptera* spp., *Probstmayria* spp., *Pseudofilaria* spp., *Setaria* spp., *Skjrabinema* spp., *Spirocerca* spp., *Stephanofilaria* spp., *Strongyluris* spp., *Syphacia* spp., *Thelazia* spp., *Toxascaris* spp., *Toxocara* spp., *Wuchereria* spp.

Acanthocephala: from the order of Oligacanthorhynchida, for example: *Macracanthorhynchus* spp., *Prosthenorchis* spp.; from the order of Moniliformida, for example: *Moniliformis* spp.

From the order of Polymorphida, for example: *Filicollis* spp.; from the order of Echinorhynchida, for example *Acanthocephalus* spp., *Echinorhynchus* spp., *Leptorhynchoides* spp.

Pentastoma: from the order of Porocephalida, for example, *Linguatula* spp.

In the veterinary field and in animal husbandry, the compounds of the formula (I) are administered by methods generally known in the art, such as via the enteral, parenteral, dermal or nasal route in the form of suitable preparations. Administration may be prophylactic, metaphylactic or therapeutic.

Thus, one embodiment of the present invention relates to the compounds of the formula (I) for use as a medicament.

A further aspect relates to the compounds of the formula (I) for use as an antiendoparasitic agent.

A further specific aspect of the invention relates to the compounds of the formula (I) for use as an antihelminthic agent, especially for use as a nematicide, platyhelminthicide, acanthocephalicide or pentastomicide.

A further specific aspect of the invention relates to the compounds of the formula (I) for use as an antiprotozoic agent.

A further aspect relates to the compounds of the formula (I) for use as an antiectoparasitic agent, especially an arthropodicide, very particularly an insecticide or an acaricide.

Further aspects of the invention are veterinary medicine formulations comprising an effective amount of at least one compound of the formula (I) and at least one of the following: a pharmaceutically acceptable excipient (e.g. solid or liquid diluents), a pharmaceutically acceptable auxiliary (e.g. surfactants), especially a pharmaceutically acceptable excipient used conventionally in veterinary medicine formulations and/or a pharmaceutically acceptable auxiliary conventionally used in veterinary medicine formulations.

A related aspect of the invention is a method for production of a veterinary medicine formulation as described here, which comprises the step of mixing at least one compound of the formula (I) with pharmaceutically acceptable excipients and/or auxiliaries, especially with pharmaceutically acceptable excipients used conventionally in veterinary medicine formulations and/or auxiliaries used conventionally in veterinary medicine formulations.

Another specific aspect of the invention is veterinary medicine formulations selected from the group of ectoparasiticidal and endoparasiticidal formulations, especially selected from the group of anthelmintic, antiprotozoic and arthropodicidal formulations, very particularly selected from the group of nematicidal, platyhelminthicidal, acanthocephalicidal, pentastomicidal, insecticidal and acaricidal formulations, according to the aspects mentioned, and methods for production thereof.

Another aspect relates to a method for treatment of a parasitic infection, especially an infection caused by a parasite selected from the group of the ectoparasites and endoparasites mentioned here, by use of an effective amount of a compound of the formula (I) in an animal, especially a nonhuman animal, having a need therefor.

Another aspect relates to a method for treatment of a parasitic infection, especially an infection caused by a parasite selected from the group of the ectoparasites and endoparasites mentioned here, by use of a veterinary medicine formulation as defined here in an animal, especially a nonhuman animal, having a need therefor.

Another aspect relates to the use of the compounds of the formula (I) in the treatment of a parasite infection, especially an infection caused by a parasite selected from the group of the ectoparasites and endoparasites mentioned here, in an animal, especially a nonhuman animal.

In the present context of animal health or veterinary medicine, the term "treatment" includes prophylactic, metaphylactic and therapeutic treatment.

In a particular embodiment, in this way, mixtures of at least one compound of the formula (I) with other active ingredients, especially with endo- and ectoparasiticides, are provided for the field of veterinary medicine.

In the field of animal health, "mixture" means not just that two (or more) different active ingredients are formulated in a common formulation and are correspondingly employed together, but also relates to products comprising formulations separated for each active ingredient. Accordingly, when more than two active ingredients are to be employed, all active ingredients can be formulated in a common formulation or all active ingredients can be formulated in separate formulations; likewise conceivable are mixed forms in which some of the active ingredients are formulated together and some of the active ingredients are formulated separately. Separate formulations allow the separate or successive application of the active ingredients in question.

The active ingredients specified here by their "common names" are known and are described, for example, in the "Pesticide Manual" (see above) or can be searched for on the Internet (e.g.: http:/www.alanwood.net/pesticides).

Illustrative active ingredients from the group of the ectoparasiticides as mixing components include, without any intention that this should constitute a restriction, the insecticides and acaricides listed in detail above. Further usable active ingredients are listed below in accordance with the abovementioned classification based on the current IRAC Mode of Action Classification Scheme: (1) acetylcholinesterase (AChE) inhibitors; (2) GABA-gated chloride channel blockers; (3) sodium channel modulators; (4) nicotinic acetylcholine receptor (nAChR) competitive modulators; (5) nicotinic acetylcholine receptor (nAChR) allosteric modulators; (6) glutamate-gated chloride channel (GluC1) allosteric modulators; (7) juvenile hormone mimetics; (8) miscellaneous non-specific (multi-site) inhibitors; (9) chordotonal organ modulators; (10) mite growth inhibitors; (12) inhibitors of mitochondrial ATP synthase, such as ATP disruptors; (13) uncouplers of oxidative phosphorylation via disruption of the proton gradient; (14) nicotinic acetylcholine receptor channel blockers; (15) inhibitors of chitin biosynthesis, type 0; (16) inhibitors of chitin biosynthesis, type 1; (17) moulting disruptors (especially in Diptera); (18) ecdysone receptor agonists; (19) octopamine receptor agonists; (21) mitochondrial complex I electron transport inhibitors; (25) mitochondrial complex II electron transport inhibitors; (20) mitochondrial complex III electron transport inhibitors; (22) voltage-dependent sodium channel blockers; (23) inhibitors of acetyl CoA carboxylase; (28) ryanodine receptor modulators;

active ingredients having unknown or non-specific mechanisms of action, e.g. fentrifanil, fenoxacrim, cycloprene, chlorobenzilate, chlordimeform, flubenzimin, dicyclanil, amidoflumet, quinomethionat, triarathene, clothiazoben, tetrasul, potassium oleate, petroleum, metoxadiazone, gossyplur, flutenzine, brompropylate, cryolite;

compounds from other classes, for example butacarb, dimetilan, cloethocarb, phosphocarb, pirimiphos(-ethyl), parathion(-ethyl), methacrifos, isopropyl o-salicylate, trichlorfon, sulprofos, propaphos, sebufos, pyridathion, prothoate, dichlofenthion, demeton-S-methyl sulfone, isazofos, cyanofenphos, dialifos, carbophenothion, autathiofos, aromfenvinfos(-methyl), azinphos(-ethyl), chlorpyrifos(-ethyl), fosmethilan, iodofenphos, dioxabenzofos, formothion, fonofos, flupyrazofos, fensulfothion, etrimfos;

organochlorine compounds, for example camphechlor, lindane, heptachlor; or phenylpyrazoles, e.g. acetoprole, pyrafluprole, pyriprole, vaniliprole, sisapronil; or isoxazolines, e.g. sarolaner, afoxolaner, lotilaner, fluralaner;

pyrethroids, e.g. (cis-, trans-)metofluthrin, profluthrin, flufenprox, flubrocythrinate, fubfenprox, fenfluthrin, protrifenbut, pyresmethrin, RU15525, terallethrin, cis-resmethrin, heptafluthrin, bioethanomethrin, biopermethrin, fenpyrithrin, cis-cypermethrin, cis-permethrin, clocythrin, cyhalothrin (lambda-), chlovaporthrin, or halogenated hydrocarbon compounds (HCHs), neonicotinoids, e.g. nithiazine dicloromezotiaz, triflumezopyrim macrocyclic lactones, e.g. nemadectin, ivermectin, latidectin, moxidectin, selamectin, eprinomectin, doramectin, emamectin benzoate; milbemycin oxime triprene, epofenonane, diofenolan;

biologicals, hormones or pheromones, for example natural products, e.g. thuringiensin, codlemone or neem components dinitrophenols, e.g. dinocap, dinobuton, binapacryl;
benzoylureas, e.g. fluazuron, penfluron,
amidine derivatives, e.g. chlormebuform, cymiazole, demiditraz
beehive varroa acaricides, for example organic acids, e.g. formic acid, oxalic acid.

Illustrative active ingredients from the group of the endoparasiticides, as mixing components, include, but are not limited to, active anthelmintic ingredients and active antiprotozoic ingredients.

The active anthelmintic ingredients include but are not limited to the following active nematicidal, trematicidal and/or cestocidal compounds:

from the class of the macrocyclic lactones, for example: eprinomectin, abamectin, nemadectin, moxidectin, doramectin, selamectin, lepimectin, latidectin, milbemectin, ivermectin, emamectin, milbemycin;

from the class of the benzimidazoles and probenzimidazoles, for example: oxibendazole, mebendazole, triclabendazole, thiophanate, parbendazole, oxfendazole, netobimin, fenbendazole, febantel, thiabendazole, cyclobendazole, cambendazole, albendazole sulfoxide, albendazole, flubendazole;

from the class of the depsipeptides, preferably cyclic depsipeptides, especially 24-membered cyclic depsipeptides, for example: emodepside, PF1022A;

from the class of the tetrahydropyrimidines, for example: morantel, pyrantel, oxantel;

from the class of the imidazothiazoles, for example: butamisole, levamisole, tetramisole;

from the class of the aminophenylamidines, for example: amidantel, deacylated amidantel (dAMD), tribendimidine;

from the class of the aminoacetonitriles, for example: monepantel;

from the class of the paraherquamides, for example: paraherquamide, derquantel;

from the class of the salicylanilides, for example: tribromsalan, bromoxanide, brotianide, clioxanide, closantel, niclosamide, oxyclozanide, rafoxanide;

from the class of the substituted phenols, for example: nitroxynil, bithionol, disophenol, hexachlorophene, niclofolan, meniclopholan;

from the class of the organophosphates, for example: trichlorfon, naphthalofos, dichlorvos/DDVP, crufomate, coumaphos, haloxon;

from the class of the piperazinones/quinolines, for example: praziquantel, epsiprantel;

from the class of the piperazines, for example: piperazine, hydroxyzine;

from the class of the tetracyclines, for example: tetracycline, chlortetracycline, doxycycline, oxytetracycline, rolitetracycline;

from various other classes, for example: bunamidine, niridazole, resorantel, omphalotin, oltipraz, nitroscanate, nitroxynil, oxamniquin, mirasan, miracil, lucanthon, hycanthon, hetolin, emetin, diethylcarbamazine, dichlorophen, diamfenetide, clonazepam, bephenium, amoscanate, clorsulon.

Active antiprotozoic ingredients include, but are not limited to, the following active ingredients:

from the class of the triazines, for example: diclazuril, ponazuril, letrazuril, toltrazuril;

from the class of polyether ionophores, for example: monensin, salinomycin, maduramicin, narasin;

from the class of the macrocyclic lactones, for example: milbemycin, erythromycin;

from the class of the quinolones, for example: enrofloxacin, pradofloxacin;

from the class of the quinines, for example: chloroquine;
from the class of the pyrimidines, for example: pyrimethamine;

from the class of the sulfonamides, for example: sulfaquinoxaline, trimethoprim, sulfaclozin;

from the class of the thiamines, for example: amprolium;
from the class of the lincosamides, for example: clindamycin;

from the class of the carbanilides, for example: imidocarb;
from the class of the nitrofurans, for example: nifurtimox;
from the class of the quinazolinone alkaloids, for example: halofuginone;

from various other classes, for example: oxamniquin, paromomycin;

from the class of the vaccines or antigens from microorganisms, for example: *Babesia canis rossi, Eimeria tenella, Eimeria praecox, Eimeria necatrix, Eimeria mitis, Eimeria maxima, Eimeria brunetti, Eimeria acervulina, Babesia canis vogeli, Leishmania infantum, Babesia canis canis, Dictyocaulus viviparus.*

All the mixing components mentioned, as the case may be, may also form salts with suitable bases or acids if they are capable of doing so on the basis of their functional groups.

Vector Control

The compounds of the formula (I) can also be used in vector control. In the context of the present invention, a vector is an arthropod, especially an insect or arachnid, capable of transmitting pathogens, for example viruses, worms, single-cell organisms and bacteria, from a reservoir (plant, animal, human, etc.) to a host. The pathogens can be transmitted either mechanically (for example trachoma by non-stinging flies) onto a host or after injection into a host (for example malaria parasites by mosquitoes).

Examples of vectors and the diseases or pathogens they transmit are:

1) Mosquitoes
   *Anopheles*: malaria, filariasis;
   *Culex*: Japanese encephalitis, filariasis, other viral diseases, transmission of other worms;
   *Aedes*: yellow fever, dengue fever, further viral disorders, filariasis;
   Simuliidae: transmission of worms, especially *Onchocerca volvulus;*
   Psychodidae: transmission of leishmaniasis
2) Lice: skin infections, epidemic typhus;
3) Fleas: plague, endemic typhus, tapeworms;
4) Flies: sleeping sickness (trypanosomiasis); cholera, other bacterial diseases;
5) Mites: acariosis, epidemic typhus, rickettsialpox, tularaemia, Saint Louis encephalitis, tick-borne encephalitis (TBE), Crimean-Congo haemorrhagic fever, borreliosis;
6) Ticks: borellioses such as *Borrelia bungdorferi* sensu lato., *Borrelia duttoni*, tick-borne encephalitis, Q fever (*Coxiella burnetii*), babesioses (*Babesia canis canis*), ehrlichiosis.

Examples of vectors in the context of the present invention are insects, for example aphids, flies, leafhoppers or *thrips*, which can transmit plant viruses to plants. Other vectors capable of transmitting plant viruses are spider mites, lice, beetles and nematodes.

Further examples of vectors in the context of the present invention are insects and arachnids such as mosquitoes, especially of the genera *Aedes, Anopheles*, for example *A.* gambiae, A. arabiensis, A. funestus, A. dirus (malaria) and Culex, Psychodidae such as Phlebotomus, Lutzomyia, lice, fleas, flies, mites and ticks, which can transmit pathogens to animals and/or humans.

Vector control is also possible if the compounds of the formula (I) are resistance-breaking.

Compounds of the formula (I) are suitable for use in the prevention of diseases and/or pathogens transmitted by vectors. Thus, a further aspect of the present invention is the use of compounds of the formula (I) for vector control, for example in agriculture, in horticulture, in forests, in gardens and in leisure facilities, and also in the protection of materials and stored products.

Protection of Industrial Materials

The compounds of the formula (I) are suitable for protecting industrial materials against attack or destruction by insects, for example from the orders of Coleoptera, Hymenoptera, Isoptera, Lepidoptera, Psocoptera and Zygentoma.

Industrial materials in the present context are understood to mean inanimate materials, such as preferably plastics, adhesives, sizes, papers and cards, leather, wood, processed wood products and coating compositions. The use of the invention for protection of wood is particularly preferred.

In a further embodiment, the compounds of the formula (I) are used together with at least one further insecticide and/or at least one fungicide.

In a further embodiment, the compounds of the formula (I) take the form of a ready-to-use pesticide, meaning that they can be applied to the material in question without further modifications. Useful further insecticides or fungicides especially include those mentioned above.

Surprisingly, it has also been found that the compounds of the formula (I) can be employed for protecting objects which come into contact with saltwater or brackish water, in particular hulls, screens, nets, buildings, moorings and signalling systems, against fouling. It is equally possible to use the compounds of the formula (I), alone or in combinations with other active ingredients, as antifouling agents.

Control of Animal Pests in the Hygiene Sector

The compounds of the formula (I) are suitable for controlling animal pests in the hygiene sector. More particularly, the invention can be used in the domestic protection sector, in the hygiene protection sector and in the protection of stored products, particularly for control of insects, arachnids, ticks and mites encountered in enclosed spaces, for example dwellings, factory halls, offices, vehicle cabins, animal breeding facilities. For controlling animal pests, the compounds of the formula (I) are used alone or in combination with other active ingredients and/or auxiliaries. They are preferably used in domestic insecticide products. The compounds of the formula (I) are effective against sensitive and resistant species, and against all developmental stages.

These pests include, for example, pests from the class Arachnida, from the orders Scorpiones, Araneae and Opiliones, from the classes Chilopoda and Diplopoda, from the class Insecta the order Blattodea, from the orders Coleoptera, Dermaptera, Diptera, Heteroptera, Hymenoptera, Isoptera, Lepidoptera, Phthiraptera, Psocoptera, Saltatoria or Orthoptera, Siphonaptera and Zygentoma and from the class Malacostraca the order Isopoda.

Application is effected, for example, in aerosols, unpressurized spray products, for example pump and atomizer sprays, automatic fogging systems, foggers, foams, gels, evaporator products with evaporator tablets made of cellulose or plastic, liquid evaporators, gel and membrane evaporators, propeller-driven evaporators, energy-free, or passive, evaporation systems, moth papers, moth bags and moth gels, as granules or dusts, in baits for spreading or bait stations.

PREPARATION EXAMPLES 2-(3-Ethylsulfonylpyrazolo[1,5-a]pyridin-2-yl)-3-methyl-6-(trifluoromethyl)imidazo[4,5-c]pyridine
(Ex. 1-1)

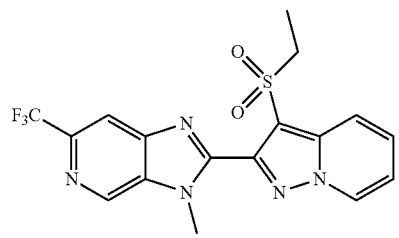 [SMILES: CCS(=O)(=O)c1c(-c2nc3cc(C(F)(F)F)ncc3n2C)nn2ccccc12]

100 mg (0.25 mmol) of 2-(3-bromopyrazolo[1,5-a]pyridin-2-yl)-3-methyl-6-(trifluoromethyl)-imidazo[4,5-c]pyridine, 146.6 mg (1.26 mmol) of sodium ethanesulfinate and 7.2 mg (0.03 mmol) of copper(I) iodide were stirred in 10 ml of N,N-dimethylformamide in a microwave synthesis unit (Anton Paar, Monowave 400) at 120° C. for four hours. Subsequently, a sodium chloride solution was added to the reaction mixture, which was extracted with ethyl acetate. The organic phase was dried over sodium sulfate and then the solvent was distilled off under reduced pressure. The residue was purified by column chromatography purification via preparative HPLC with a water/acetonitrile gradient as eluent.

(log P (neutral): 2.26; MH$^+$: 410; $^1$H NMR (600 MHz, D$_6$-DMSO) δ ppm: 1.23 (t, 3H), 3.74 (q, 2H), 4.10 (s, 3H), 7.39-7.41 (m, 1H), 7.77-7.80 (m, 1H), 8.17 (d, 1H), 8.32 (s, 1H), 9.07 (d, 1H), 9.30 (s, 1H).

2-(3-Bromopyrazolo[1,5-a]pyridin-2-yl)-3-methyl-6-(trifluoromethyl)imidazo[4,5-c]pyridine

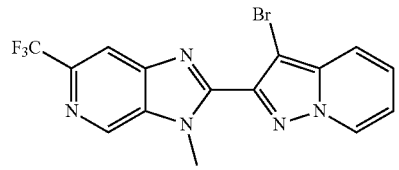 [SMILES: Cn1c(-c2nn3ccccc3c2Br)nc2cc(C(F)(F)F)ncc21]

320 mg (1.67 mmol) of N3-methyl-6-(trifluoromethyl)pyridine-3,4-diamine, 504 mg (2.09 mmol) of 3-bromopyrazolo[1,5-a]pyridine-2-carboxylic acid and 321 mg (1.67 mmol) of 1-(3-dimethylamino-propyl)-3-ethylcarbodiimide hydrochloride (EDCI) were stirred in 10 ml of pyridine under argon at room temperature for 16 h. The reaction mixture was freed of the solvent under reduced pressure, water was added to the residue and extraction was effected with ethyl acetate. The organic phase was dried over sodium sulfate and then the solvent was distilled off under reduced pressure. The residue was then stirred in 10 ml of toluene in the presence of 159 mg (83 mmol) of para-toluenesulfonic acid under reflux for 6 h. The mixture was admixed with sodium hydrogencarbonate solution and extracted three times with ethyl acetate. The combined organic phases were dried over sodium sulfate and then the solvent was distilled off under reduced pressure.

(log P (neutral): 2.86; MH⁺: 396; $^1$H NMR (400 MHz, D$_6$-DMSO) δ ppm: 4.29 (s, 3H), 7.21 (t, 1H), 7.53 (t, 1H), 7.78 (d, 1H), 8.32 (s, 1H), 8.92 (d, 1H), 9.27 (s, 1H).

In analogy to the examples and in accordance with the preparation processes described above, it is possible to prepare the following compounds of the formula (I):

2-(3-Ethylsulfonylpyrazolo[1,5-a]pyrimidin-2-yl)-3-methyl-6-(trifluoromethyl)imidazo[4,5-c]-pyridine (Ex. I-2)

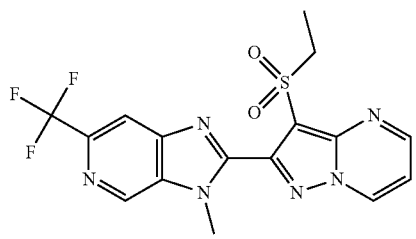 [SMILES: CCS(=O)(=O)c1c(-c2nc3cc(C(F)(F)F)ncc3n2C)nn2cccnc12]

(log P (neutral): 1.58; MH⁺: 411; $^1$H NMR (400 MHz, D$_6$-DMSO) δ ppm: 1.20 (t, 3H), 3.55 (q, 2H), 3.97 (s, 3H), 7.56-7.59 (m, 1H), 8.32 (s, 1H), 9.03-9.06 (m, 1H), 9.29 (s, 1H), 9.51 (d, 1H).

3-Ethylsulfonyl-5,7-dimethyl-2-[3-methyl-6-(trifluoromethyl)imidazo[4,5-c]pyridin-2-yl]-pyrazolo[1,5-a]pyrimidine (Ex. I-3)

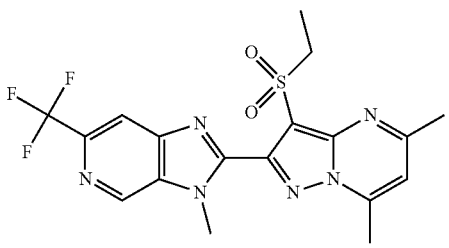 [SMILES: CCS(=O)(=O)c1c(-c2nc3cc(C(F)(F)F)ncc3n2C)nn2c(C)cc(C)nc12]

(log P (neutral): 2.00; MH⁺: 439; $^1$H NMR (400 MHz, D$_6$-DMSO) δ ppm: 1.17 (t, 3H), 2.69 (s, 3H), 2.80 (s, 3H), 3.53 (q, 2H), 3.95 (s, 3H), 7.42 (s, 1H), 8.30 (s, 1H), 9.27 (s, 1H).

In analogy to the examples and according to the above-described preparation processes, the following compounds of the formula (I) can be obtained:

| Example | Structure |
|---------|-----------|
| I-1 | 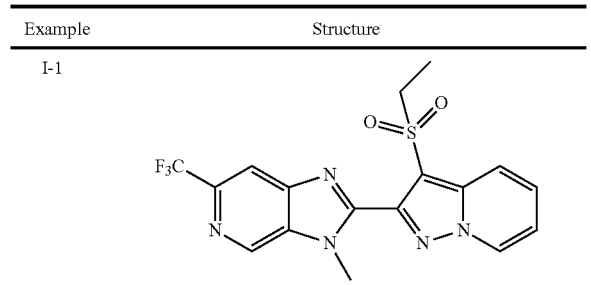 |
| I-2 | 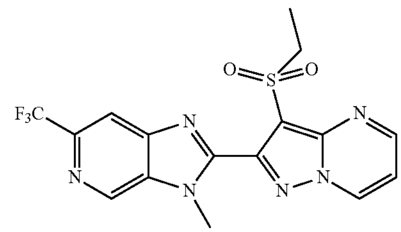 [SMILES: CCS(=O)(=O)c1c(-c2nc3cc(C(F)(F)F)ncc3n2C)nn2cccnc12] |
| I-3 | 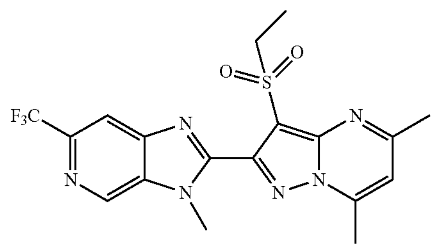 [SMILES: CCS(=O)(=O)c1c(-c2nc3cc(C(F)(F)F)ncc3n2C)nn2c(C)cc(C)nc12] |
| I-4 | 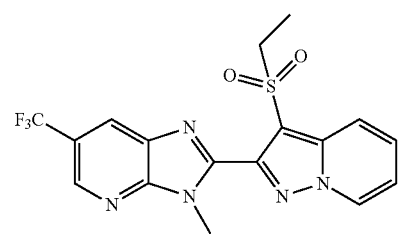 [SMILES: CCS(=O)(=O)c1c(-c2nc3cc(C(F)(F)F)cnc3n2C)nn2ccccc12] |
| I-5 | 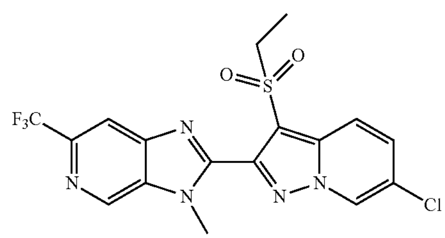 [SMILES: CCS(=O)(=O)c1c(-c2nc3cc(C(F)(F)F)ncc3n2C)nn2cc(Cl)ccc12] |
| I-6 | 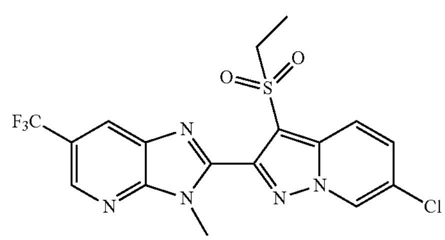 [SMILES: CCS(=O)(=O)c1c(-c2nc3cc(C(F)(F)F)cnc3n2C)nn2cc(Cl)ccc12] |
| I-7 | 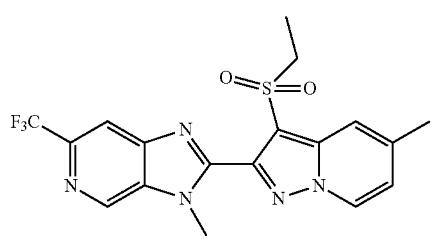 [SMILES: CCS(=O)(=O)c1c(-c2nc3cc(C(F)(F)F)ncc3n2C)nn2ccc(C)cc12] |

-continued

| Example | Structure |
|---|---|
| I-8 | 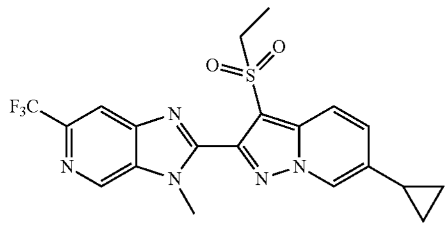 [SMILES: CCS(=O)(=O)c1c(-c2nc3cc(C(F)(F)F)ncc3n2C)nn2cc(C3CC3)ccc12] |
| I-9 | 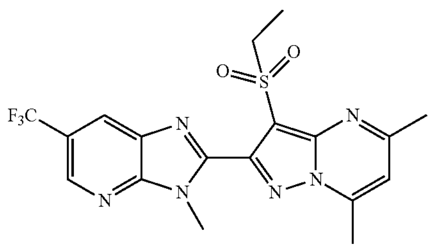 [SMILES: CCS(=O)(=O)c1c(-c2nc3cc(C(F)(F)F)cnc3n2C)nn2c(C)cc(C)nc12] |
| I-10 | 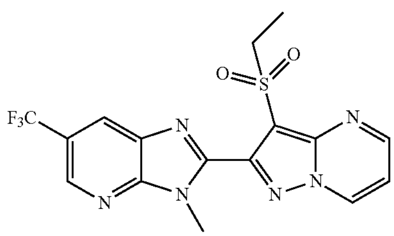 [SMILES: CCS(=O)(=O)c1c(-c2nc3cc(C(F)(F)F)cnc3n2C)nn2cccnc12] |
| I-11 | 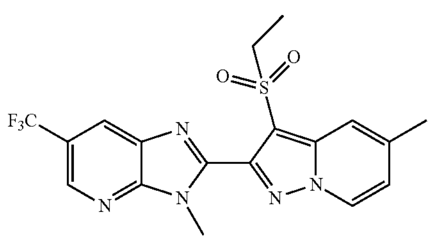 [SMILES: CCS(=O)(=O)c1c(-c2nc3cc(C(F)(F)F)cnc3n2C)nn2ccc(C)cc12] |
| I-12 | 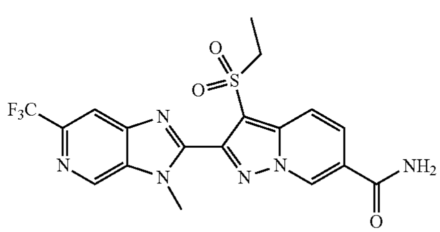 [SMILES: CCS(=O)(=O)c1c(-c2nc3cc(C(F)(F)F)ncc3n2C)nn2cc(C(N)=O)ccc12] |
| I-13 | 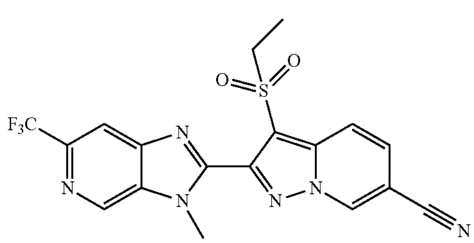 [SMILES: CCS(=O)(=O)c1c(-c2nc3cc(C(F)(F)F)ncc3n2C)nn2cc(C#N)ccc12] |

The log P values are measured according to EEC Directive 79/831 Annex V.A8 by HPLC (high-performance liquid chromatography) on a reversed-phase column (C 18). Temperature: 55° C.

The LC-MS determination in the acidic range is effected at pH 2.7 with 0.1% aqueous formic acid and acetonitrile (containing 0.1% formic acid) as eluents; linear gradient from 10% acetonitrile to 95% acetonitrile. Called log P (HCOOH) in the table.

The LC-MS determination in the neutral range is effected at pH 7.8 with 0.001 molar aqueous ammonium hydrogencarbonate solution and acetonitrile as eluents; linear gradient from 10% acetonitrile to 95% acetonitrile. Called log P (neutral) in the table.

Calibration is effected using unbranched alkan-2-ones (having 3 to 16 carbon atoms) with known log P values (log P values determined on the basis of the retention times by linear interpolation between two successive alkanones).

The NMR data of selected examples are listed either in conventional form (δ values, multiplet splitting, number of hydrogen atoms) or as NMR peak lists.

In each case, the solvent in which the NMR spectrum was recorded is stated.

NMR Peak List Method

The 1H-NMR data of selected examples are noted in the form of 1H-NMR peak lists. For each signal peak, first the δ value in ppm and then the signal intensity in round brackets are listed. The pairs of δ value-signal intensity numbers for different signal peaks are listed with separation from one another by semicolons.

The peak list for one example therefore takes the form of:
$\delta_1$ (intensity$_1$); $\delta_2$ (intensity$_2$); ... ; $\delta_i$ (intensity$_i$); ... ; $\delta_n$ (intensity$_n$)

The intensity of sharp signals correlates with the height of the signals in a printed example of an NMR spectrum in cm and shows the true ratios of the signal intensities. In the case of broad signals, several peaks or the middle of the signal and the relative intensity thereof may be shown in comparison to the most intense signal in the spectrum.

For calibration of the chemical shift of 1H NMR spectra we use tetramethylsilane and/or the chemical shift of the solvent, particularly in the case of spectra measured in DMSO. Therefore, the tetramethylsilane peak may but need not occur in NMR peak lists.

The lists of the 1H NMR peaks are similar to the conventional 1H NMR printouts and thus usually contain all peaks listed in a conventional NMR interpretation.

In addition, like conventional 1H NMR printouts, they may show solvent signals, signals of stereoisomers of the target compounds, which likewise form part of the subject-matter of the invention, and/or peaks of impurities.

In the reporting of compound signals in the delta range of solvents and/or water, our lists of 1H NMR peaks show the usual solvent peaks, for example peaks of DMSO in DMSO-$D_6$ and the peak of water, which usually have a high intensity on average.

The peaks of stereoisomers of the target compounds and/or peaks of impurities usually have a lower intensity on average than the peaks of the target compounds (for example with a purity of >90%).

Such stereoisomers and/or impurities may be typical of the particular preparation process. Their peaks can thus help in identifying reproduction of our preparation process with reference to "by-product fingerprints".

An expert calculating the peaks of the target compounds by known methods (MestreC, ACD simulation, but also with empirically evaluated expected values) can, if required, isolate the peaks of the target compounds, optionally using additional intensity filters. This isolation would be similar to the relevant peak picking in conventional 1H NMR interpretation.

Further details of 1H NMR peak lists can be found in the Research Disclosure Database Number 564025.

| Example | |
|---|---|
| I-10 | ¹H-NMR(400.0 MHz, d₆-DMSO):<br>δ = 9.5148(1.6); 9.5107(1.7); 9.4973(1.7); 9.4931(1.7); 9.0413(1.6); 9.0372(1.7); 9.0307(1.8); 9.0265(1.7); 8.9076(2.2); 8.9039(2.3); 8.7048(2.3); 8.7005(2.3); 7.5845(1.6); 7.5739(1.6); 7.5669(1.6); 7.5563(1.6); 3.9786(0.5); 3.8718(16.0); 3.6013(1.0); 3.5828(3.4); 3.5643(3.4); 3.5456(1.0); 3.3227 (307.2); 2.6751(1.0); 2.6707(1.4); 2.6663(1.1); 2.5240(3.4); 2.5103(90.7); 2.5061(187.1); 2.5017 (247.9); 2.4972(178.7); 2.4930(87.3); 2.3329(1.1); 2.3285(1.5); 2.3240(1.1); 1.2288(0.5); 1.2189 (3.6); 1.2005(7.9); 1.1820(3.5); 0.1461(0.3); 0.0079(2.3); −0.0002(74.7); −0.0084(2.9) |
| I-9 | ¹H-NMR(400.0 MHz, d₆-DMSO):<br>δ = 8.8949(2.7); 8.8919(2.7); 6.6783(2.7); 8.6739(2.7); 7.4133(3.9); 3.8477(16.0); 3.5764(1.1); 3.5579 (3.5); 3.5394(3.5); 3.5212(1.1); 3.3206(77.1); 2.7990(12.6); 2.6861(14.4); 2.6712(1.0); 2.6663 (0.7); 2.5905(0.4); 2.5058(85.3); 2.5017(109.1); 2.4974(82.2); 2.3283(0.6); 2.3240(0.5); 2.0743 (2.9); 2.0738(2.9); 1.2354(0.6); 1.1952(3.9); 1.1768(8.1); 1.1584(3.6); 0.1458(0.5); 0.0070(5.1); −0.0001(102.5); −0.0007(101.1); −0.1498(0.5) |
| I-8 | ¹H-NMR(400.0 MHz, d₆-DMSO):<br>δ = 9.2894(3.9); 8.9254(3.1); 8.3199(4.3); 8.0597(2.1); 8.0365(2.3); 7.5414(1.7); 7.5378(1.6); 7.5179 (1.5); 7.5144(1.5); 4.0978(16.0); 3.7623(1.0); 3.7439(3.2); 7.7254(3.2); 3.7072(1.0); 3.3199(45.7); 2.6753(0.4); 2.6712(0.6); 2.6668(0.4); 2.5244(1.5); 2.5108(39.2); 2.5066(78.0); 2.5021(100.6); 2.4977(71.6); 2.3333(0.4); 2.3289(0.6); 2.3242(0.4); 2.1623(0.6); 2.1537(0.6); 2.1414(1.1); 2.1289 (0.7); 2.1205(0.6); 1.2296(3.5); 1.2112(7.7); 1.1928(3.3); 1.0803(0.6); 1.0687(1.9); 1.0635(2.2); 1.0526(1.1); 1.0477(2.0); 1.0425(2.0); 1.0320(0.8); 0.9016(0.8); 0.8904(2.4); 0.8863(2.3); 0.8784 (2.1); 0.8737(2.5); 0.8616(0.6); 0.1462(0.5); 0.0079(3.7); −0.0002(107.2); −0.0085(4.2); −0.1494(0.5) |
| I-7 | ¹H-NMR(400.0 MHz, d₆-DMSO):<br>δ = 9.2907(3.7); 8.9634(2.0); 8.9458(2.0); 8.3193(3.9); 7.9394(2.3); 7.2625(1.4); 7.2580(1.5); 7.2448 (1.4); 7.2402(1.4); 4.0817(16.0); 3.7375(0.9); 3.7191(3.2); 3.7006(3.2); 3.6822(1.0); 3.3196(49.1); 2.6753(0.4); 2.6707(0.6); 2.6662(0.4); 2.5242(11.4); 2.5104(36.3); 2.5062(74.4); 2.5017(99.7); 2.4972(73.6); 2.4929(37.0); 2.3330(0.4); 2.3285(0.6); 2.3239(0.5); 1.2416(3.4); 1.2233(7.6); 1.2048 (3.3); 0.1459(0.5); 0.0079(3.9); −0.0001(105.3); −0.0084(4.8); −0.1498(0.5) |
| I-6 | ¹H-NMR(400.0 MHz, d₆-DMSO):<br>δ = 9.4988(2.6); 9.4963(2.6); 9.4944(2.3); 8.9197(2.1); 8.9154(2.2); 8.7265(2.3); 8.7227(2.2); 8.1873 (2.0); 8.1633(2.4); 7.8754(1.8); 7.8709(1.8); 7.8514(1.6); 7.8469(1.7); 4.0180(16.0); 3.8426(0.9); 3.8245(3.0); 3.8060(3.0); 3.7876(0.9); 3.3575(18.0); 2.6750(0.7); 2.6706(0.9); 2.6662(0.7); 2.5240 (2.1); 2.5104(56.6); 2.5061(120.2); 2.5016(162.5); 2.4971(117.2); 2.4927(56.3); 2.3325(0.6); 2.3284(0.9); 2.3240(0.7); 1.2550(3.1); 1.2367(7.3); 1.2182(3.2); 0.0079(0.5); −0.0002(19.0); −0.0085(0.7) |
| I-5 | ¹H-NMR(400.0 MHz, d₆-DMSO):<br>δ = 9.4985(2.7); 9.4960(2.7); 9.2988(3.9); 8.3368(4.1); 8.1763(2.1); 8.1522(2.5); 7.8804(2.0); 7.8759 (2.0); 7.8564(1.7); 7.8519(1.8); 4.1066(16.0); 3.8036(0.9); 3.7853(3.2); 3.7668(3.2); 3.7485(0.9); 3.3211(31.6); 2.6754(0.4); 2.6708(0.6); 2.6664(0.4); 2.5241(1.3); 2.5104(35.2); 2.5063(72.1); 2.5018(95.5); 2.4974(68.9); 2.4931(33.4); 2.3328(0.4); 2.3284(0.6); 2.3241(0.4); 1.2479(3.4); 1.2296 (7.6); 1.2111(3.3); 0.1459(0.5); 0.0078(3.7); −0.0002(107.1); −0.0085(4.2); −0.1498(0.5) |
| I-4 | ¹H-NMR(400.0 MHz, d₆-DMSO):<br>δ = 9.0862(2.1); 9.0688(2.1); 8.9096(2.8); 8.7163(2.9); 8.1984(1.8); 8.1761(2.0); 7.8051(1.2); 7.7859 (1.4); 7.7649(1.1); 7.4206(1.1); 7.4031(2.0); 7.3858(1.0); 4.0173(16.0); 3.8176(1.0); 3.7992(3.4); 3.7807(3.4); 3.7623(1.1); 3.3225(20.0); 2.6725(0.3); 2.5070(49.2); 2.5032(60.6); 2.3299(0.4); 2.0757(0.7); 1.2552(3.6); 1.2368(7.8); 1.2184(3.5); −0.0002(11.1) |
| I-3 | ¹H-NMR(400.0 MHz, d₆-DMSO):<br>δ = 9.2740(4.4); 8.3147(1.1); 8.2989(4.6); 7.4156(4.0); 3.9479(16.0); 3.5601(1.2); 3.5418(3.5); 3.5234 (3.6); 3.5052(1.1); 3.3904(0.4); 3.3798(0.4); 3.3185(513.6); 3.2795(0.5); 2.8921(0.4); 2.7949 (12.6); 2.7312(0.6); 2.6868(14.8); 2.6747(4.5); 2.6706(5.5); 2.6185(0.5); 2.5884(0.7); 2.5057(661.2); 2.5014(891.6); 2.4972(678.3); 2.3327(3.9); 2.3282(5.2); 1.1920(3.7); 1.1738(8.1); 1.1553(3.6); 0.1464(3.7); 0.0080(34.3); 0.0000(771.2); −0.1491(3.6) |
| I-2 | ¹H-NMR(400.0 MHz, d₆-DMSO):<br>δ = 9.5112(2.3); 9.5082(2.3); 9.4947(2.2); 9.2867(4.7); 9.0394(2.7); 9.0324(2.4); 8.3211(5.2); 8.2531 (0.7); 7.5866(1.9); 7.5763(2.2); 7.5687(1.8); 7.5585(1.7); 7.0853(0.6); 6.6784(0.5); 4.0249(0.5); 3.9737(16.0); 3.5823(1.6); 3.5643(4.0); 3.5460(3.9); 3.5271(1.5); 3.3213(556.3); 3.1258(2.0); 2.6708(6.3); 2.5049(951.8); 2.5015(1007.1); 2.3934(0.5); 2.3282(5.7); 1.2747(0.7); 1.2565(1.3); 1.2380(1.6); 1.2149(4.5); 1.1962(8.5); 1.1773(3.9); 1.1475(0.4); 1.1075(0.4); 0.1459(2.5); −0.0001(490.0); −0.0704(0.5); −0.0854(0.4); −0.1503(2.4) |
| I-1 | ¹H-NMR(601.6 MHz, d₆-DMSO):<br>δ = 19.9774(0.9); 9.2980(3.3); 9.0762(1.8); 9.0647(1.8); 8.3235(3.5); 8.1818(1.6); 8.1669(1.8); 7.8018 (1.0); 7.7886(1.2); 7.7739(1.0); 7.4144(0.9); 7.4049(1.7); 7.4027(1.7); 7.3933(0.9); 4.1021(16.0); 3.7611(0.9); 3.7490(3.1); 3.7368(3.1); 3.7246(1.0); 3.3031(85.0); 2.6120(1.2); 2.5213(2.1); 2.5182 (2.6); 2.5152(2.5); 2.5063(72.5); 2.5033(157.6); 2.5003(220.8); 2.4973(157.9); 2.4943(72.6); 2.3846(1.3); 1.2398(3.2); 1.2275(7.5); 1.2152(3.4); 0.0964(1.0); 0.0052(6.8); −0.0002(239.8); −0.0057(8.0); −0.1000(1.0) |
| I-11 | ¹H-NMR(400.0 MHz, d₆-DMSO):<br>δ = 8.9647(2.1); 8.9471(2.1); 8.9039(2.4); 8.9008(2.5); 8.7035(2.5); 8.6999(2.5); 7.9510(2.5); 7.2583 (1.5); 7.2538(1.5); 7.2404(1.5); 7.2361(1.5); 3.9929(16.0); 3.7771(0.9); 3.7587(3.2); 3.7403(3.2); 3.7221(1.0); 3.3214(27.5); 2.6718(0.4); 2.5235(11.1); 2.5071(50.0); 2.5028(65.1); 2.4984(48.2); 2.3296(0.4); 2.0754(2.0); 1.2505(3.4); 1.2321(7.8); 1.2137(3.3); 0.0077(0.4); −0.0002(8.4) |
| I-12 | ¹H-NMR(400.0 MHz, d₆-DMSO):<br>δ = 9.5596(3.6); 9.3093(4.4); 8.3448(4.9); 8.3286(1.5); 8.2191(1.1); 8.1956(3.8); 8.1801(2.8); 8.1776 (2.9); 8.1567(0.8); 8.1540(0.9); 7.8180(1.4); 4.4510(0.9); 4.1280(16.0); 3.8146(1.0); 3.7961(3.3); 3.7777(3.4); 3.7594(1.1); 3.3211(38.1); 2.6713(0.5); 2.6672(0.4); 2.5065(68.7); 2.5024(90.9); 2.4981(69.0); 2.3332(0.4); 2.3290(0.5); 2.0749(0.8); 1.2582(3.5); 1.2399(7.9); 1.2215(3.6); 0.0000 (64.4) |

| Example | |
|---|---|
| I-13 | $^1$H-NMR(400 MHz, D$_6$-DMSO) δ 6 ppm: 1.24 (t, 3H), 3.80 (q, 2H), 4.12 (s, 3H), 8.02 (d, 1H), 8.25 (d, 1H), 8.35 (s, 1H), 9.31 (s, 1H), 10.00 (s, 1H). |

USE EXAMPLES

*Tetranychus urticae*—Spray Test, OP-Resistant

| Solvent: | 78.0 parts by weight of acetone |
|---|---|
| | 1.5 parts by weight of dimethylformamide |
| Emulsifier: | alkylaryl polyglycol ether |

To produce a suitable active ingredient formulation, 1 part by weight of active ingredient is dissolved with the specified parts by weight of solvent and made up to the desired concentration with water containing an emulsifier concentration of 1000 ppm. To produce further test concentrations, the formulation is diluted with emulsifier-containing water.

Discs of bean leaves (*Phaseolus vulgaris*) infested with all stages of the greenhouse red spider mite (*Tetranychus urticae*) are sprayed with an active ingredient formulation of the desired concentration.

After 6 days, the efficacy in % is determined. 100% means that all the spider mites have been killed; 0% means that no spider mites have been killed.

In this test, for example, the following compounds from the preparation examples shows an efficacy of 90% at an application rate of 20 g/ha: 1-2.

*Myzus persicae*—Spray Test

| Solvent: | 78 parts by weight of acetone |
|---|---|
| | 1.5 parts by weight of dimethylformamide |
| Emulsifier: | alkylaryl polyglycol ether |

To produce a suitable active ingredient formulation, 1 part by weight of active ingredient is dissolved with the specified parts by weight of solvent and made up to the desired concentration with water containing an emulsifier concentration of 1000 ppm. To produce further test concentrations, the formulation is diluted with emulsifier-containing water.

Discs of Chinese cabbage leaves (*Brassica pekinensis*) infested by all stages of the green peach aphid (*Myzus persicae*) are sprayed with an active ingredient formulation of the desired concentration.

After 5 days, the efficacy in % is determined. 100% means that all the aphids have been killed; 0% means that no aphids have been killed.

In this test, for example, the following compounds from the preparation examples show an efficacy of 100% at an application rate of 100 g/ha: I-1, I-3

In this test, for example, the following compounds from the preparation examples show an efficacy of 90% at an application rate of 100 g/ha: I-2, I-4, I-6

*Myzus persicae*—Oral Test

| Solvent: | 100 parts by weight of acetone |
|---|---|

To produce a suitable active ingredient formulation, 1 part by weight of active ingredient is dissolved with the stated parts by weight of solvent and made up to the desired concentration with water.

50 µl of the active ingredient preparation are transferred into microtitre plates and made up to a final volume of 200 µl with 150 µl of IPL41 insect medium (33%+15% sugar). Subsequently, the plates are sealed with parafilm, which a mixed population of green peach aphids (*Myzus persicae*) within a second microtitre plate is able to puncture and imbibe the solution.

After 5 days, the efficacy in % is determined. 100% means that all the aphids have been killed; 0% means that no aphids have been killed.

In this test, for example, the following compounds from the preparation examples show an efficacy of 100% at an application rate of 20 ppm: I-1, I-2, I-3

In this test, for example, the following compounds from the preparation examples show an efficacy of 100% at an application rate of 4 ppm: I-1, I-2, I-3, I-4, I-5, I-6

*Phaedon cochleariae*—Spray Test

| Solvent: | 78.0 parts by weight of acetone |
|---|---|
| | 1.5 parts by weight of dimethylformamide |
| Emulsifier: | alkylaryl polyglycol ether |

To produce a suitable active ingredient formulation, 1 part by weight of active ingredient is dissolved with the specified parts by weight of solvent and made up to the desired concentration with water containing an emulsifier concentration of 1000 ppm. To produce further test concentrations, the formulation is diluted with emulsifier-containing water.

Discs of Chinese cabbage leaves (*Brassica pekinensis*) are sprayed with an active ingredient formulation of the desired concentration and, after drying, populated with larvae of the mustard beetle (*Phaedon cochleariae*).

After 7 days, the efficacy in % is determined. 100% means that all the beetle larvae have been killed; 0% means that no beetle larvae have been killed.

In this test, for example, the following compounds from the preparation examples show an efficacy of 100% at an application rate of 100 g/ha: I-4, I-5, I-6

*Spodoptera frugiperda*—Spray Test

| Solvent: | 78.0 parts by weight of acetone |
|---|---|
| | 1.5 parts by weight of dimethylformamide |
| Emulsifier: | alkylaryl polyglycol ether |

To produce a suitable active ingredient formulation, 1 part by weight of active ingredient is dissolved with the specified parts by weight of solvent and made up to the desired concentration with water containing an emulsifier concentration of 1000 ppm. To produce further test concentrations, the formulation is diluted with emulsifier-containing water.

Leaf discs of maize (*Zea mays*) are sprayed with an active ingredient formulation of the desired concentration and, after drying, populated with caterpillars of the armyworm (*Spodoptera frugiperda*).

After 7 days, the efficacy in % is determined. 100% means that all the caterpillars have been killed; 0% means that no caterpillar has been killed.

In this test, for example, the following compounds from the preparation examples show an efficacy of 100% at an application rate of 100 g/ha: I-4, I-5, I-6

*Ctenocephalides felis*—In Vitro Contact Tests with Adult Cat Fleas

For the coating of the test tubes, 9 mg of active ingredient are first dissolved in 1 ml of acetone p.a. and then diluted to the desired concentration with acetone p.a. 250 µl of the solution are distributed homogeneously on the inner walls and the base of a 25 ml glass tube by turning and rocking on an orbital shaker (rocking rotation at 30 rpm for 2 h). With 900 ppm of active ingredient solution and internal surface area 44.7 cm², given homogeneous distribution, an area-based dose of 5 µg/cm² is achieved.

After the solvent has evaporated off, the tubes are populated with 5-10 adult cat fleas (*Ctenocephalides felis*), sealed with a perforated plastic lid and incubated in a horizontal position at room temperature and ambient humidity. After 48 h, efficacy is determined. To this end, the tubes are stood upright and the fleas are knocked to the base of the tube. Fleas which remain motionless at the base or move in an uncoordinated manner are considered to be dead or moribund.

A substance shows good efficacy against *Ctenocephalides felis* if at least 80% efficacy was achieved in this test at an application rate of 5 µg/cm². 100% efficacy means that all the fleas were dead or moribund. 0% efficacy means that no fleas were harmed.

In this test, for example, the following compounds from the preparation examples show an efficacy of 100% at an application rate of 5 µg/cm² (=500 g/ha): I-1, I-4

*Boophilus microplus*—Injection Test

Solvent: dimethyl sulfoxide

To produce a suitable active ingredient formulation, 10 mg of active ingredient are mixed with 0.5 ml of solvent and the concentrate is diluted to the desired concentration with solvent.

1 µl of the active ingredient solution is injected into the abdomen of 5 engorged adult female cattle ticks (*Boophilus microplus*). The animals are transferred into dishes and kept in a climate-controlled room.

Efficacy is assessed after 7 days by laying of fertile eggs. Eggs which are not visibly fertile are stored in a climate-controlled cabinet until the larvae hatch after about 42 days. An efficacy of 100% means that none of the ticks has laid any fertile eggs; 0% means that all the eggs are fertile.

In this test, for example, the following compounds from the preparation examples show an efficacy of 100% at an application rate of 20 µg/animal: I-3

*Ctenocephalides felis*—Oral Test

Solvent: dimethyl sulfoxide

To produce a suitable active ingredient formulation, 10 mg of active ingredient are mixed with 0.5 ml of dimethyl sulfoxide. Dilution with citrated cattle blood gives the desired concentration.

About 20 unfed adult cat fleas (*Ctenocephalides felis*) are placed into a chamber which is closed at the top and bottom with gauze. A metal cylinder whose bottom end is closed with parafilm is placed onto the chamber. The cylinder contains the blood/active ingredient formulation, which can be imbibed by the fleas through the parafilm membrane.

After 2 days, the kill in % is determined. 100% means that all of the fleas have been killed; 0% means that none of the fleas have been killed.

In this test, for example, the following compounds from the preparation examples show an efficacy of 100% at an application rate of 100 ppm: I-1, I-3

*Lucilia cuprina* Test

Solvent: dimethyl sulfoxide

To produce a suitable active ingredient formulation, 10 mg of active ingredient are mixed with 0.5 ml of dimethyl sulfoxide, and the concentrate is diluted with water to the desired concentration.

About 20 L1 larvae of the Australian sheep blowfly (*Lucilia cuprina*) are transferred into a test vessel containing minced horsemeat and the active ingredient formulation of the desired concentration.

After 2 days, the kill in % is determined. 100% means that all the larvae have been killed; 0% means that no larvae have been killed.

In this test, for example, the following compounds from the preparation examples show an efficacy of 100% at an application rate of 100 ppm: I-1, I-4

In this test, for example, the following compounds from the preparation examples show an efficacy of 97% at an application rate of 100 ppm: I-3

*Musca domestica* Test

Solvent: dimethyl sulfoxide

To produce a suitable active ingredient formulation, 10 mg of active ingredient are mixed with 0.5 ml of dimethyl sulfoxide, and the concentrate is diluted with water to the desired concentration.

Vessels containing a sponge treated with sugar solution and the active ingredient formulation of the desired concentration are populated with 10 adult houseflies (*Musca domestica*).

After 2 days, the kill in % is determined. 100% means that all of the flies have been killed; 0% means that none of the flies have been killed.

In this test, for example, the following compounds from the preparation examples show an efficacy of 90% at an application rate of 100 ppm: I-4

The invention claimed is:

1. Compound of formula (I)

in which

Aa is nitrogen or $=C(R^{10})-$,
Ab is nitrogen or $=C(R^{11})-$,
Ac is nitrogen or $=C(R^{12})-$,
Ad is nitrogen,
where not more than two of Aa, Ab, Ac and Ad can be nitrogens,
$R^1$ is $(C_1-C_6)$-alkyl, $(C_1-C_6)$-haloalkyl, $(C_1-C_6)$-cyanoalkyl, $(C_1-C_6)$-hydroxyalkyl, $(C_1-C_6)$-alkoxy-$(C_1-C_6)$-alkyl, $(C_1-C_6)$-haloalkoxy-$(C_1-C_6)$-alkyl, $(C_2-C_6)$-alkenyl, $(C_2-C_6)$-alkenyloxy-$(C_1-C_6)$-alkyl, $(C_2-C_6)$-haloalkenyloxy-$(C_1-C_6)$-alkyl, $(C_2-C_6)$-haloalkenyl, $(C_2-C_6)$-cyanoalkenyl, $(C_2-C_6)$-alkynyl, $(C_2-C_6)$-alkynyloxy-$(C_1-C_6)$-alkyl, $(C_2-C_6)$-haloalkynyloxy-$(C_1-C_6)$-alkyl, $(C_2-C_6)$-haloalkynyl, $(C_2-C_6)$-cyanoalkynyl, $(C_3-C_8)$-cycloalkyl, $(C_3-C_8)$-cycloalkyl-$(C_3-C_8)$-cycloalkyl, $(C_1-C_6)$-alkyl-$(C_3-C_8)$-cycloalkyl, halo-$(C_3-C_8)$-cycloalkyl, amino, $(C_1-C_6)$-alkylamino, di-$(C_1-C_6)$-alkyl-amino, $(C_3-C_8)$-cycloalkylamino, $(C_1-C_6)$- alkylcarbonylamino, ($C_1$-$C_6$)-alkylthio-($C_1$-$C_6$)-alkyl, ($C_1$-$C_6$)-haloalkylthio-($C_1$-$C_6$)-alkyl, ($C_1$-$C_6$)-alkylsulfinyl-($C_1$-$C_6$)-alkyl, ($C_1$-$C_6$)-haloalkylsulfinyl-($C_1$-$C_6$)-alkyl, ($C_1$-$C_6$)-alkylsulfonyl-($C_1$-$C_6$)-alkyl, ($C_1$-$C_6$)-haloalkylsulfonyl-($C_1$-$C_6$)alkyl, ($C_1$-$C_6$)-alkoxy-($C_1$-$C_6$)-alkylthio-($C_1$-$C_6$)-alkyl, ($C_1$-$C_6$)-alkoxy-($C_1$-$C_6$)-alkylsulfinyl-($C_1$-$C_6$)-alkyl, ($C_1$-$C_6$)-alkoxy-($C_1$-$C_6$)-alkylsulfonyl-($C_1$-$C_6$)-alkyl, ($C_1$-$C_6$)-alkylcarbonyl-($C_1$-$C_6$)-alkyl, ($C_1$-$C_6$)-haloalkylcarbonyl-($C_1$-$C_6$)-alkyl, ($C_1$-$C_6$)-alkoxycarbonyl-($C_1$-$C_6$)-alkyl, ($C_1$-$C_6$)-haloalkoxycarbonyl-($C_1$-$C_6$)-alkyl, ($C_1$-$C_6$)-alkylsulfonylamino, aminosulfonyl-($C_1$-$C_6$)-alkyl, ($C_1$-$C_6$)-alkylaminosulfonyl-($C_1$-$C_6$)-alkyl, di-($C_1$-$C_6$)-alkylaminosulfonyl-($C_1$-$C_6$)-alkyl, or is in each case optionally identically or differently mono- or poly-aryl-, -hetaryl- or -heterocyclyl-substituted ($C_1$-$C_6$)-alkyl, ($C_1$-$C_6$)-alkoxy, ($C_2$-$C_6$)-alkenyl, ($C_2$-$C_6$)-alkynyl, ($C_3$-$C_8$)-cycloalkyl, where aryl, hetaryl or heterocyclyl may each optionally be mono- or polysubstituted identically or differently by halogen, cyano, nitro, hydroxyl, amino, carboxyl, carbamoyl, aminosulfonyl, ($C_1$-$C_6$)-alkyl, ($C_3$-$C_6$)-cycloalkyl, ($C_1$-$C_6$)-alkoxy, ($C_1$-$C_6$)-haloalkyl, ($C_1$-$C_6$)-haloalkoxy, ($C_1$-$C_6$)-alkylthio, ($C_1$-$C_6$)-alkylsulfinyl, ($C_1$-$C_6$)-alkylsulfonyl, ($C_1$-$C_6$)-alkylsulfimino, ($C_1$-$C_6$)-alkylsulfimino-($C_1$-$C_6$)-alkyl, ($C_1$-$C_6$)-alkylsulfimino-($C_2$-$C_6$)-alkylcarbonyl, ($C_1$-$C_6$)-alkylsulfoximino, ($C_1$-$C_6$)-alkylsulfoximino-($C_1$-$C_6$)-alkyl, ($C_1$-$C_6$)-alkylsulfoximino-($C_2$-$C_6$)-alkylcarbonyl, ($C_1$-$C_6$)-alkoxycarbonyl, ($C_1$-$C_6$)-alkylcarbonyl, ($C_3$-$C_6$)-trialkylsilyl or benzyl, or $R^1$ is aryl, hetaryl or heterocyclyl, each of which is optionally mono- or polysubstituted identically or differently by halogen, cyano, nitro, hydroxyl, amino, carboxyl, carbamoyl, ($C_1$-$C_6$)-alkyl, ($C_3$-$C_8$)-cycloalkyl, ($C_1$-$C_6$)-alkoxy, ($C_1$-$C_6$)-haloalkyl, ($C_1$-$C_6$)-haloalkoxy, ($C_1$-$C_6$)-alkylthio, ($C_1$-$C_6$)-alkylsulfinyl, ($C_1$-$C_6$)-alkylsulfonyl, ($C_1$-$C_6$)-alkylsulfimino, ($C_1$-$C_6$)-alkylsulfimino-($C_1$-$C_6$)-alkyl, ($C_1$-$C_6$)-alkylsulfimino-($C_2$-$C_6$)-alkylcarbonyl, ($C_1$-$C_6$)-alkylsulfoximino, ($C_1$-$C_6$)-alkylsulfoximino-($C_1$-$C_6$)-alkyl, ($C_1$-$C_6$)-alkylsulfoximino-($C_2$-$C_6$)-alkylcarbonyl, ($C_1$-$C_6$)-alkoxycarbonyl, ($C_1$-$C_6$)-alkylcarbonyl, ($C_3$-$C_6$)-trialkylsilyl, (=O) (in the case of heterocyclyl only) and (=O)$_2$ (in the case of heterocyclyl only), $R^{10}$, $R^{11}$, $R^{12}$ are independently hydrogen, cyano, halogen, nitro, acetyl, hydroxyl, amino, SCN, ($C_3$-$C_8$)-cycloalkyl, ($C_3$-$C_8$)-cycloalkyl-($C_3$-$C_8$)-cycloalkyl, ($C_1$-$C_6$)-alkyl-($C_3$-$C_8$)-cycloalkyl, halo-($C_3$-$C_8$)-cycloalkyl, ($C_1$-$C_6$)-alkyl, ($C_1$-$C_6$)-haloalkyl, ($C_1$-$C_6$)-cyanoalkyl, ($C_1$-$C_6$)-hydroxyalkyl, hydroxycarbonyl-($C_1$-$C_6$)-alkoxy, ($C_1$-$C_6$)-alkoxycarbonyl-($C_1$-$C_6$)-alkyl, ($C_1$-$C_6$)-alkoxy-($C_1$-$C_6$)-alkyl, ($C_2$-$C_6$)-alkenyl, ($C_2$-$C_6$)-haloalkenyl, ($C_2$-$C_6$)-cyanoalkenyl, ($C_2$-$C_6$)-alkynyl, ($C_2$-$C_6$)-haloalkynyl, ($C_2$-$C_6$)-cyanoalkynyl, ($C_1$-$C_6$)-alkoxy, ($C_1$-$C_6$)-haloalkoxy, ($C_1$-$C_6$)-cyanoalkoxy, ($C_1$-$C_6$)-alkoxycarbonyl-($C_1$-$C_6$)-alkoxy, ($C_1$-$C_6$)-alkoxy-($C_1$-$C_6$)-alkoxy, ($C_1$-$C_6$)-alkylhydroxyimino, ($C_1$-$C_6$)-alkoxyimino, ($C_1$-$C_6$)-alkyl-($C_1$-$C_6$)-alkoxyimino, ($C_1$-$C_6$)-haloalkyl-($C_1$-$C_6$)-alkoxyimino, ($C_1$-$C_6$)-alkylthio, ($C_1$-$C_6$)-haloalkylthio, ($C_1$-$C_6$)-alkoxy-($C_1$-$C_6$)-alkylthio, ($C_1$-$C_6$)-alkylthio-($C_1$-$C_6$)-alkyl, ($C_1$-$C_6$)-alkylsulfinyl, ($C_1$-$C_6$)-haloalkylsulfinyl, ($C_1$-$C_6$)-alkoxy-($C_1$-$C_6$)-alkylsulfinyl, ($C_1$-$C_6$)-alkylsulfinyl-($C_1$-$C_6$)-alkyl, ($C_1$-$C_6$)-alkylsulfonyl, ($C_1$-$C_6$)-haloalkylsulfonyl, ($C_1$-$C_6$)-alkoxy-($C_1$-$C_6$)-alkylsulfonyl, ($C_1$-$C_6$)-alkylsulfonyl-($C_1$-$C_6$)-alkyl, ($C_1$-$C_6$)-alkylsulfonyloxy, ($C_1$-$C_6$)-alkylcarbonyl, ($C_1$-$C_6$)-alkylthiocarbonyl, ($C_1$-$C_6$)-haloalkylcarbonyl, ($C_1$-$C_6$)-alkylcarbonyloxy, ($C_1$-$C_6$)-alkoxycarbonyl, ($C_1$-$C_6$)-haloalkoxycarbonyl, aminocarbonyl, ($C_1$-$C_6$)-alkylaminocarbonyl, ($C_1$-$C_6$)-alkylaminothiocarbonyl, di-($C_1$-$C_6$)-alkylaminocarbonyl, di-($C_1$-$C_6$)-alkylaminothiocarbonyl, ($C_2$-$C_6$)-alkenylaminocarbonyl, di-($C_2$-$C_6$)-alkenylaminocarbonyl, ($C_3$-$C_8$)-cycloalkylaminocarbonyl, ($C_1$-$C_6$)-alkylsulfonylamino, ($C_1$-$C_6$)-alkylamino, di-($C_1$-$C_6$)-alkylamino, aminosulfonyl, ($C_1$-$C_6$)-alkylaminosulfonyl, di-($C_1$-$C_6$)-alkylaminosulfonyl, ($C_1$-$C_6$)-alkylsulfoximino, aminothiocarbonyl, ($C_1$-$C_6$)-alkylaminothiocarbonyl, di-($C_1$-$C_6$)-alkylaminothiocarbonyl, ($C_3$-$C_8$)-cycloalkylamino, NHCO—($C_1$-$C_6$)-alkyl (($C_1$-$C_6$)-alkylcarbonylamino), or are in each case optionally singly or multiply, identically or differently substituted aryl or hetaryl, where (in the case of hetaryl) at least one carbonyl group may optionally be present and/or where possible substituents in each case are as follows: cyano, carboxyl, halogen, nitro, acetyl, hydroxyl, amino, SCN, tri-($C_1$-$C_6$)-alkylsilyl, ($C_3$-$C_8$)cycloalkyl, ($C_3$-$C_8$)cycloalkyl-($C_3$-$C_8$)cycloalkyl, ($C_1$-$C_6$)alkyl-($C_3$-$C_8$)cycloalkyl, halo($C_3$-$C_8$)cycloalkyl, ($C_1$-$C_6$)alkyl, ($C_1$-$C_6$)haloalkyl, ($C_1$-$C_6$)cyanoalkyl, ($C_1$-$C_6$)hydroxyalkyl, hydroxycarbonyl-($C_1$-$C_6$)-alkoxy, ($C_1$-$C_6$)alkoxycarbonyl-($C_1$-$C_6$)alkyl, ($C_1$-$C_6$)alkoxy-($C_1$-$C_6$)alkyl, ($C_2$-$C_6$)alkenyl, ($C_2$-$C_6$)haloalkenyl, ($C_2$-$C_6$)cyanoalkenyl, ($C_2$-$C_6$)alkynyl, ($C_2$-$C_6$)haloalkynyl, ($C_2$-$C_6$)cyanoalkynyl, ($C_1$-$C_6$)alkoxy, ($C_1$-$C_6$)haloalkoxy, ($C_1$-$C_6$)cyanoalkoxy, ($C_1$-$C_6$)alkoxycarbonyl-($C_1$-$C_6$)alkoxy, ($C_1$-$C_6$)alkoxy-($C_1$-$C_6$)alkoxy, ($C_1$-$C_6$)alkylhydroxyimino, ($C_1$-$C_6$)alkoxyimino, ($C_1$-$C_6$)alkyl-($C_1$-$C_6$)alkoxyimino, ($C_1$-$C_6$)haloalkyl-($C_1$-$C_6$)alkoxyimino, ($C_1$-$C_6$)alkylthio, ($C_1$-$C_6$)haloalkylthio, ($C_1$-$C_6$)alkoxy-($C_1$-$C_6$)alkylthio, ($C_1$-$C_6$)alkylthio-($C_1$-$C_6$)alkyl, ($C_1$-$C_6$)alkylsulfinyl, ($C_1$-$C_6$)haloalkylsulfinyl, ($C_1$-$C_6$)alkoxy-($C_1$-$C_6$)alkylsulfinyl, ($C_1$-$C_6$)alkylsulfinyl-($C_1$-$C_6$)alkyl, ($C_1$-$C_6$)alkylsulfonyl, ($C_1$-$C_6$)haloalkylsulfonyl, ($C_1$-$C_6$)alkoxy-($C_1$-$C_6$)alkylsulfonyl, ($C_1$-$C_6$)alkylsulfonyl-($C_1$-$C_6$)alkyl, ($C_1$-$C_6$)alkyl sulfonyloxy, ($C_1$-$C_6$)alkylcarbonyl, ($C_1$-$C_6$)haloalkylcarbonyl, ($C_1$-$C_6$)alkylcarbonyloxy, ($C_1$-$C_6$)alkoxycarbonyl, ($C_1$-$C_6$)haloalkoxycarbonyl, aminocarbonyl, ($C_1$-$C_6$)alkylaminocarbonyl, di-($C_1$-$C_6$)alkylaminocarbonyl, ($C_2$-$C_6$)alkenylaminocarbonyl, di-($C_1$-$C_6$)-alkenylaminocarbonyl, ($C_3$-$C_8$)cycloalkylaminocarbonyl, ($C_1$-$C_6$)alkylsulfonylamino, ($C_1$-$C_6$)alkylamino, di-($C_1$-$C_6$)alkylamino, aminosulfonyl, ($C_1$-$C_6$)alkylaminosulfonyl, di-($C_1$-$C_6$)alkylaminosulfonyl, ($C_1$-$C_6$)alkylsulfoximino, aminothiocarbonyl, ($C_1$-$C_6$)alkylaminothiocarbonyl, di-($C_1$-$C_6$)alkylaminothiocarbonyl, ($C_3$-$C_8$)cycloalkylamino, ($C_1$-$C_6$)alkylcarbonylamino, where only one or two of the $R^{10}$, $R^{11}$, $R^{12}$ radicals is/are a substituent other than hydrogen, Q is a partly saturated or saturated heterocyclic or heteroaromatic 8-, 9-, 10-, 11- or 12-membered fused bicyclic or tricyclic ring system where at least one carbonyl group may optionally be present and/or where the ring system is optionally mono- or polysubstituted identically or differently, and where the substituents may independently be selected from cyano, halogen, nitro, acetyl, hydroxyl, amino, SCN, tri-($C_1$-$C_6$)-alkylsilyl, ($C_3$-$C_8$)-cycloalkyl, ($C_3$-$C_8$)-cycloalkyl-($C_3$-$C_8$)- cycloalkyl, $(C_1-C_6)$-alkyl-$(C_3-C_8)$-cycloalkyl, halo-$(C_3-C_8)$-cycloalkyl, $(C_1-C_6)$-alkyl, $(C_1-C_6)$-haloalkyl, $(C_1-C_6)$-cyanoalkyl, $(C_1-C_6)$-hydroxyalkyl, hydroxycarbonyl-$(C_1-C_6)$-alkoxy, $(C_1-C_6)$-alkoxycarbonyl-$(C_1-C_6)$-alkyl, $(C_1-C_6)$-alkoxy-$(C_1-C_6)$-alkyl, $(C_2-C_6)$-alkenyl, $(C_2-C_6)$-haloalkenyl, $(C_2-C_6)$-cyanoalkenyl, $(C_2-C_6)$-alkynyl, $(C_2-C_6)$-alkynyloxy-$(C_1-C_4)$-alkyl, $(C_2-C_6)$-haloalkynyl, $(C_2-C_6)$-cyanoalkynyl, $(C_1-C_6)$-alkoxy, $(C_1-C_6)$-haloalkoxy, $(C_1-C_6)$-haloalkoxy-$(C_1-C_6)$-alkyl, $(C_2-C_6)$-alkenyloxy-$(C_1-C_6)$-alkyl, $(C_2-C_6)$-haloalkenyloxy-$(C_1-C_6)$-alkyl, $(C_1-C_6)$-cyanoalkoxy, $(C_1-C_6)$-alkoxycarbonyl-$(C_1-C_6)$-alkoxy, $(C_1-C_6)$-alkoxy-$(C_1-C_6)$-alkoxy, $(C_1-C_6)$-alkylhydroxyimino, $(C_1-C_6)$-alkoxyimino, $(C_1-C_6)$-alkyl-$(C_1-C_6)$-alkoxyimino, $(C_1-C_6)$-haloalkyl-$(C_1-C_6)$-alkoxyimino, $(C_1-C_6)$-alkylthio, $(C_1-C_6)$-haloalkylthio, $(C_1-C_6)$-alkoxy-$(C_1-C_6)$-alkylthio, $(C_1-C_6)$-alkylthio-$(C_1-C_6)$-alkyl, $(C_1-C_6)$-alkylsulfinyl, $(C_1-C_6)$-haloalkylsulfinyl, $(C_1-C_6)$-alkoxy-$(C_1-C_6)$-alkylsulfinyl, $(C_1-C_6)$-alkylsulfinyl-$(C_1-C_6)$-alkyl, $(C_1-C_6)$-alkylsulfonyl, $(C_1-C_6)$-haloalkylsulfonyl, $(C_1-C_6)$-alkoxy-$(C_1-C_6)$-alkyl sulfonyl, $(C_1-C_6)$-alkylsulfonyl-$(C_1-C_6)$-alkyl, $(C_1-C_6)$-alkylsulfonyloxy, $(C_1-C_6)$-alkylcarbonyl, $(C_1-C_6)$-alkylcarbonyl-$(C_1-C_6)$-alkyl, $(C_1-C_6)$-alkylthiocarbonyl, $(C_1-C_6)$-haloalkylcarbonyl, $(C_1-C_6)$-alkylcarbonyloxy, $(C_1-C_6)$-alkoxycarbonyl, $(C_1-C_6)$-haloalkoxycarbonyl, aminocarbonyl, $(C_1-C_6)$-alkylaminocarbonyl, $(C_1-C_6)$-alkylaminothiocarbonyl, di-$(C_1-C_6)$-alkyl-aminocarbonyl, di-$(C_1-C_6)$-alkylaminothiocarbonyl, $(C_2-C_6)$-alkenylaminocarbonyl, di-$(C_2-C_6)$-alkenylaminocarbonyl, $(C_3-C_8)$-cycloalkylaminocarbonyl, $(C_1-C_6)$-alkylsulfonylamino, $(C_1-C_6)$-alkylamino, di-$(C_1-C_6)$-alkylamino, aminosulfonyl, $(C_1-C_6)$-alkylaminosulfonyl, di-$(C_1-C_6)$-alkylaminosulfonyl, $(C_1-C_6)$-alkylsulfoximino, aminothiocarbonyl, $(C_1-C_6)$-alkylaminothiocarbonyl, di-$(C_1-C_6)$-alkyl-aminothiocarbonyl, $(C_3-C_8)$-cycloalkylamino, NHCO—$(C_1-C_6)$-alkyl ($(C_1-C_6)$-alkylcarbonylamino), or where the substituents may independently be selected from phenyl or a 5- or 6-membered heteroaromatic ring, where phenyl or the ring may optionally be mono- or polysubstituted identically or differently by $C_1-C_6$-alkyl, $C_2-C_6$-alkenyl, $C_2-C_6$-alkynyl, $C_3-C_6$-cycloalkyl, $C_1-C_6$ haloalkyl, $C_2-C_6$-haloalkenyl, $C_2-C_6$-haloalkynyl, $C_3-C_6$-halocycloalkyl, halogen, CN, NO$_2$, $C_1-C_4$-alkoxy, $C_1-C_4$-haloalkoxy, n is 0, 1 or 2.

2. Compound of formula (I) according to claim 1 in which

Aa is nitrogen or $=C(R^{10})-$,

Ab is nitrogen or $=C(R^{11})-$,

Ac is nitrogen or $=C(R^{12})-$,

Ad is nitrogen, where not more than two of Aa, Ab, Ac and Ad can be nitrogens, $R^1$ is $(C_1-C_4)$alkyl, $(C_1-C_4)$hydroxyalkyl, $(C_1-C_4)$haloalkyl, $(C_1-C_4)$cyanoalkyl, $(C_1-C_4)$alkoxy-$(C_1-C_4)$alkyl, $(C_1-C_4)$haloalkoxy-$(C_1-C_4)$alkyl, $(C_2-C_4)$alkenyl, $(C_2-C_4)$alkenyloxy-$(C_1-C_4)$alkyl, $(C_2-C_4)$haloalkenyloxy-$(C_1-C_4)$alkyl, $(C_2-C_4)$haloalkenyl, $(C_2-C_4)$cyanoalkenyl, $(C_2-C_4)$alkynyl, $(C_2-C_4)$alkynyloxy-$(C_1-C_4)$alkyl, $(C_2-C_4)$haloalkynyloxy-$(C_1-C_4)$alkyl, $(C_2-C_4)$haloalkynyl, $(C_2-C_4)$cyanoalkynyl, $(C_3-C_6)$cycloalkyl, $(C_3-C_6)$cycloalkyl($C_3-C_6$)cycloalkyl, $(C_1-C_4)$alkyl-$(C_3-C_6)$cycloalkyl, halo($C_3-C_6$)cycloalkyl, di-$(C_1-C_4)$alkylamino, di-$(C_1-C_4)$alkyl-amino, $(C_3-C_6)$cycloalkylamino, $(C_1-C_4)$alkylcarbonyl-amino, $(C_1-C_4)$alkylthio-$(C_1-C_4)$alkyl, $(C_1-C_4)$haloalkylthio-$(C_1-C_4)$alkyl, $(C_1-C_4)$alkylsulfinyl-$(C_1-C_4)$alkyl, $(C_1-C_4)$haloalkylsulfinyl-$(C_1-C_4)$alkyl, $(C_1-C_4)$alkylsulfonyl-$(C_1-C_4)$alkyl, $(C_1-C_4)$alkylcarbonyl-$(C_1-C_4)$alkyl, $(C_1-C_4)$haloalkylcarbonyl-$(C_1-C_4)$alkyl, $(C_1-C_4)$alkylsulfonyl amino, or is in each case optionally identically or differently mono- or di-aryl-, -hetaryl- or -heterocyclyl-substituted $(C_1-C_4)$alkyl, $(C_1-C_4)$alkoxy, $(C_2-C_4)$alkenyl, $(C_2-C_4)$alkynyl, $(C_3-C_6)$cycloalkyl, where aryl, hetaryl or heterocyclyl are each optionally identically or differently mono- or disubstituted by halogen, cyano, carbamoyl, aminosulfonyl, $(C_1-C_4)$alkyl, $(C_3-C_4)$cycloalkyl, $(C_1-C_4)$alkoxy, $(C_1-C_4)$haloalkyl, $(C_1-C_4)$haloalkoxy, $(C_1-C_4)$alkylthio, $(C_1-C_4)$alkylsulfinyl, $(C_1-C_4)$alkylsulfonyl, $(C_1-C_4)$alkylsulfimino, or $R^1$ is aryl, hetaryl or heterocyclyl, each of which is optionally mono- or disubstituted identically or differently by halogen, cyano, carbamoyl, $(C_1-C_4)$-alkyl, $(C_3-C_6)$-cycloalkyl, $(C_1-C_4)$-alkoxy, $(C_1-C_4)$-haloalkyl, $(C_1-C_4)$-haloalkoxy, $(C_1-C_4)$-alkylthio, $(C_1-C_4)$-alkylsulfinyl, $(C_1-C_4)$-alkylsulfonyl, $(C_1-C_4)$-alkylsulfimino, $(C_1-C_4)$-alkylsulfoximino, $(C_1-C_4)$-alkylcarbonyl, $(C_3-C_4)$-trialkylsilyl, $(=O)$ (in the case of heterocyclyl only) and $(=O)_2$ (in the case of heterocyclyl only), $R^{10}$, $R^{11}$, $R^{12}$ are independently hydrogen, cyano, halogen, nitro, acetyl, hydroxyl, amino, SCN, tri-$(C_1-C_4)$alkylsilyl, $(C_3-C_6)$cycloalkyl, $(C_3-C_6)$cycloalkyl-$(C_3-C_6)$cycloalkyl, $(C_1-C_4)$alkyl-$(C_3-C_6)$cycloalkyl, halo $(C_3-C_6)$cycloalkyl, $(C_1-C_4)$alkyl, $(C_1-C_4)$haloalkyl, $(C_1-C_4)$cyanoalkyl, $(C_1-C_4)$hydroxyalkyl, $(C_1-C_4)$alkoxy-$(C_1-C_4)$alkyl, $(C_2-C_4)$alkenyl, $(C_2-C_4)$haloalkenyl, $(C_2-C_4)$cyanoalkenyl, $(C_2-C_4)$alkynyl, $(C_2-C_4)$haloalkynyl, $(C_2-C_4)$cyanoalkynyl, $(C_1-C_4)$alkoxy, $(C_1-C_4)$haloalkoxy, $(C_1-C_4)$cyanoalkoxy, $(C_1-C_4)$alkoxy-$(C_1-C_4)$alkoxy, $(C_1-C_4)$alkylhydroxyimino, $(C_1-C_4)$alkoxyimino, $(C_1-C_4)$alkyl-$(C_1-C_4)$alkoxyimino, $(C_1-C_4)$haloalkyl-$(C_1-C_4)$alkoxyimino, $(C_1-C_4)$alkylthio, $(C_1-C_4)$haloalkylthio, $(C_1-C_4)$alkylthio-$(C_1-C_4)$alkyl, $(C_1-C_4)$alkylsulfinyl, $(C_1-C_4)$haloalkylsulfinyl, $(C_1-C_4)$alkylsulfinyl-$(C_1-C_4)$alkyl, $(C_1-C_4)$alkylsulfonyl, $(C_1-C_4)$haloalkylsulfonyl, $(C_1-C_4)$alkylsulfonyl-$(C_1-C_4)$alkyl, $(C_1-C_4)$alkylsulfonyloxy, $(C_1-C_4)$alkylcarbonyl, $(C_1-C_4)$haloalkylcarbonyl, aminocarbonyl, aminothiocarbonyl, $(C_1-C_4)$alkylaminocarbonyl, di-$(C_1-C_4)$alkylaminocarbonyl, $(C_1-C_4)$alkylsulfonylamino, $(C_1-C_4)$alkylamino, di-$(C_1-C_4)$alkylamino, aminosulfonyl, $(C_1-C_4)$alkylaminosulfonyl, di-$(C_1-C_4)$alkylaminosulfonyl, aminothiocarbonyl, NHCO—$(C_1-C_4)$alkyl ($(C_1-C_4)$alkylcarbonylamino), and also are phenyl or hetaryl, each of which is optionally mono- or disubstituted identically or differently, where (in the case of hetaryl) at least one carbonyl group may optionally be present and/or where possible substituents are in each case as follows: cyano, halogen, nitro, acetyl, amino, $(C_3-C_6)$cycloalkyl, $(C_3-C_6)$cycloalkyl-$(C_3-C_6)$cycloalkyl, $(C_1-C_4)$alkyl-$(C_3-C_6)$cycloalkyl, halo($C_3-C_6$)cycloalkyl, $(C_1-C_4)$alkyl, $(C_1-C_4)$haloalkyl, $(C_1-C_4)$cyanoalkyl, $(C_1-C_4)$hydroxyalkyl, $(C_1-C_4)$alkoxy-$(C_1-C_4)$alkyl, $(C_2-C_4)$alkenyl, $(C_2-C_4)$haloalkenyl, $(C_2-C_4)$cyanoalkenyl, $(C_2-C_4)$alkynyl, $(C_2-C_4)$haloalkynyl, $(C_2-C_4)$cyanoalkynyl, $(C_1-C_4)$alkoxy, $(C_1-C_4)$haloalkoxy, $(C_1-C_4)$cyanoalkoxy, $(C_1-C_4)$alkoxy-$(C_1-C_4)$alkoxy, $(C_1-C_4)$alkylhydroxyimino, $(C_1-C_4)$alkoxyimino, $(C_1-C_4)$alkyl-$(C_1-C_4)$alkoxyimino, $(C_1-C_4)$haloalkyl-$(C_1-C_4)$alkoxyimino, $(C_1-C_4)$ alkylthio, $(C_1-C_4)$haloalkylthio, $(C_1-C_4)$alkylthio-$(C_1-C_4)$alkyl, $(C_1-C_4)$alkylsulfinyl, $(C_1-C_4)$haloalkylsulfinyl, $(C_1-C_4)$alkylsulfinyl-$(C_1-C_4)$alkyl, $(C_1-C_4)$alkylsulfonyl, $(C_1-C_4)$haloalkylsulfonyl, $(C_1-C_4)$alkylsulfonyl-$(C_1-C_4)$alkyl, $(C_1-C_4)$alkyl sulfonyloxy, $(C_1-C_4)$alkylcarbonyl, $(C_1-C_4)$haloalkylcarbonyl, aminocarbonyl, $(C_1-C_4)$alkylaminocarbonyl, di-$(C_1-C_4)$alkylaminocarbonyl, $(C_1-C_4)$alkylsulfonylamino, $(C_1-C_4)$alkylamino, di-$(C_1-C_4)$alkylamino, aminosulfonyl, $(C_1-C_4)$alkylaminosulfonyl, di-$(C_1-C_4)$alkylaminosulfonyl, NHCO—$(C_1-C_4)$alkyl ($(C_1-C_4)$alkylcarbonylamino), where only one or two of the $R^{10}$, $R^{11}$, $R^{12}$ radicals is/are a substituent other than hydrogen, Q is a heteroaromatic 8-, 9-, 10-, 11- or 12-membered fused bicyclic or tricyclic ring system, where the ring system is optionally mono- or polysubstituted identically or differently and where the substituents may independently be selected from cyano, halogen, nitro, acetyl, hydroxyl, amino, SCN, tri-$(C_1-C_6)$-alkylsilyl, $(C_3-C_8)$-cycloalkyl, $(C_3-C_8)$-cycloalkyl-$(C_3-C_8)$-cycloalkyl, $(C_1-C_6)$-alkyl-$(C_3-C_8)$-cycloalkyl, halo-$(C_3-C_8)$-cycloalkyl, $(C_1-C_6)$-alkyl, $(C_1-C_6)$-haloalkyl, $(C_1-C_6)$-cyanoalkyl, $(C_1-C_6)$-hydroxyalkyl, $(C_1-C_6)$-alkoxy-$(C_1-C_6)$-alkyl, $(C_2-C_6)$-alkenyl, $(C_2-C_6)$-haloalkenyl, $(C_2-C_6)$-cyanoalkenyl, $(C_2-C_6)$-alkynyl, $(C_2-C_6)$-alkynyloxy-$(C_1-C_4)$-alkyl, $(C_2-C_6)$-haloalkynyl, $(C_1-C_6)$-alkoxy, $(C_1-C_6)$-haloalkoxy, $(C_1-C_6)$-haloalkoxy-$(C_1-C_6)$-alkyl, $(C_2-C_6)$-alkenyloxy-$(C_1-C_6)$-alkyl, $(C_2-C_6)$-haloalkenyloxy-$(C_1-C_6)$-alkyl, $(C_1-C_6)$-cyanoalkoxy, $(C_1-C_6)$-alkoxy-$(C_1-C_6)$-alkoxy, $(C_1-C_6)$-alkylhydroxyimino, $(C_1-C_6)$-alkoxyimino, $(C_1-C_6)$-alkyl-$(C_1-C_6)$-alkoxyimino, $(C_1-C_6)$-alkylthio, $(C_1-C_6)$-haloalkylthio, $(C_1-C_6)$-alkoxy-$(C_1-C_6)$-alkylthio, $(C_1-C_6)$-alkylthio-$(C_1-C_6)$-alkyl, $(C_1-C_6)$-alkylsulfinyl, $(C_1-C_6)$-haloalkylsulfinyl, $(C_1-C_6)$-alkoxy-$(C_1-C_6)$-alkylsulfinyl, $(C_1-C_6)$-alkylsulfinyl-$(C_1-C_6)$-alkyl, $(C_1-C_6)$-alkylsulfonyl, $(C_1-C_6)$-haloalkylsulfonyl, $(C_1-C_6)$-alkoxy-$(C_1-C_6)$-alkylsulfonyl, $(C_1-C_6)$-alkylsulfonyl-$(C_1-C_6)$-alkyl, $(C_1-C_6)$-alkylsulfonyloxy, $(C_1-C_6)$-alkylcarbonyl, $(C_1-C_6)$-alkylcarbonyl-$(C_1-C_6)$-alkyl, $(C_1-C_6)$-alkylthiocarbonyl, $(C_1-C_6)$-haloalkylcarbonyl, $(C_1-C_6)$-alkylcarbonyloxy, $(C_1-C_6)$-alkoxycarbonyl, $(C_1-C_6)$-haloalkoxycarbonyl, aminocarbonyl, $(C_1-C_6)$-alkylaminocarbonyl, $(C_1-C_6)$-alkylaminothiocarbonyl, di-$(C_1-C_6)$-alkylaminocarbonyl, di-$(C_1-C_6)$-alkylaminothiocarbonyl, $(C_3-C_8)$-cycloalkylaminocarbonyl, $(C_1-C_6)$-alkylsulfonylamino, $(C_1-C_6)$-alkylamino, di-$(C_1-C_6)$-alkylamino, aminosulfonyl, $(C_1-C_6)$-alkylaminosulfonyl, di-$(C_1-C_6)$-alkylaminosulfonyl, $(C_1-C_6)$-alkylsulfoximino, aminothiocarbonyl, $(C_1-C_6)$-alkylaminothiocarbonyl, di-$(C_1-C_6)$-alkylaminothiocarbonyl, $(C_3-C_8)$-cycloalkylamino, NHCO—$(C_1-C_6)$-alkyl ($(C_1-C_6)$-alkylcarbonylamino), or where the substituents may independently be selected from phenyl or a 5- or 6-membered heteroaromatic ring, where phenyl or the ring may optionally be mono- or polysubstituted identically or differently by $C_1-C_6$-alkyl, $C_2-C_6$-alkenyl, $C_2-C_6$-alkynyl, $C_3-C_6$-cycloalkyl, $C_1-C_6$-haloalkyl, $C_2-C_6$-haloalkenyl, $C_2-C_6$-haloalkynyl, $C_3-C_6$-halocycloalkyl, halogen, CN, $C_1-C_4$-alkoxy, $C_1-C_4$-haloalkoxy, n is 0, 1 or 2.

3. Compound of formula (I) according to claim 1 in which
Aa is nitrogen or =C($R^{10}$)—,
Ab is nitrogen or =C($R^{11}$)—,
Ac is nitrogen or =C($R^{12}$)—,
Ad is nitrogen or,
where not more than two of Aa, Ab, Ac and Ad can be nitrogens, $R^1$ is $(C_1-C_4)$-alkyl, $(C_1-C_4)$-hydroxyalkyl, $(C_1-C_4)$-haloalkyl, $(C_2-C_4)$-alkenyl, $(C_2-C_4)$-haloalkenyl, $(C_2-C_4)$-alkynyl, $(C_2-C_4)$-haloalkynyl, $(C_3-C_6)$-cycloalkyl, $(C_1-C_4)$-alkylthio-$(C_1-C_4)$-alkyl, $(C_1-C_4)$-alkylsulfinyl-$(C_1-C_4)$-alkyl or $(C_1-C_4)$-alkylsulfonyl-$(C_1-C_4)$-alkyl, $R^{10}$, $R^{11}$, $R^{12}$ are independently hydrogen, cyano, halogen, nitro, hydroxyl, amino, SCN, $(C_3-C_6)$cycloalkyl, $(C_3-C_6)$cycloalkyl-$(C_3-C_6)$cycloalkyl, $(C_1-C_4)$alkyl-$(C_3-C_6)$cycloalkyl, halo($C_3-C_6$)cycloalkyl, $(C_1-C_4)$alkyl, $(C_1-C_4)$haloalkyl, $(C_1-C_4)$cyanoalkyl, $(C_1-C_4)$alkoxy-$(C_1-C_4)$alkyl, $(C_2-C_4)$alkenyl, $(C_2-C_4)$haloalkenyl, $(C_2-C_4)$cyanoalkenyl, $(C_2-C_4)$alkynyl, $(C_2-C_4)$haloalkynyl, $(C_2-C_4)$cyanoalkynyl, $(C_1-C_4)$alkoxy, $(C_1-C_4)$haloalkoxy, $(C_1-C_4)$cyanoalkoxy, $(C_1-C_4)$alkylhydroxyimino, $(C_1-C_4)$alkoxyimino, $(C_1-C_4)$alkyl-$(C_1-C_4)$alkoxyimino, $(C_1-C_4)$alkylthio, $(C_1-C_4)$haloalkylthio, $(C_1-C_4)$alkylsulfinyl, $(C_1-C_4)$haloalkylsulfinyl, $(C_1-C_4)$alkylsulfonyl, $(C_1-C_4)$haloalkylsulfonyl, $(C_1-C_4)$alkylsulfonyloxy, $(C_1-C_4)$alkylcarbonyl, $(C_1-C_4)$haloalkylcarbonyl, aminocarbonyl, $(C_1-C_4)$alkylaminocarbonyl, di-$(C_1-C_4)$alkylaminocarbonyl, $(C_1-C_4)$alkylsulfonylamino, $(C_1-C_4)$alkylamino, di-$(C_1-C_4)$alkylamino, aminosulfonyl, $(C_1-C_4)$alkylaminosulfonyl, di-$(C_1-C_4)$alkylaminosulfonyl, NHCO—$(C_1-C_4)$alkyl ($(C_1-C_4)$alkylcarbonylamino), and also are phenyl or hetaryl, each of which is optionally mono- or disubstituted identically or differently, where (in the case of hetaryl) at least one carbonyl group may optionally be present and/or where possible substituents are in each case as follows: cyano, halogen, $(C_3-C_6)$cycloalkyl, $(C_3-C_6)$cycloalkyl-$(C_3-C_6)$cycloalkyl, $(C_1-C_4)$alkyl-$(C_3-C_6)$cycloalkyl, halo($C_3-C_6$)cycloalkyl, $(C_1-C_4)$alkyl, $(C_1-C_4)$haloalkyl, $(C_1-C_4)$cyanoalkyl, $(C_2-C_4)$alkenyl, $(C_2-C_4)$haloalkenyl, $(C_2-C_4)$cyanoalkenyl, $(C_2-C_4)$alkynyl, $(C_2-C_4)$haloalkynyl, $(C_2-C_4)$cyanoalkynyl, $(C_1-C_4)$alkoxy, $(C_1-C_4)$haloalkoxy, $(C_1-C_4)$alkylhydroxyimino, $(C_1-C_4)$alkoxyimino, $(C_1-C_4)$alkyl-$(C_1-C_4)$alkoxyimino, $(C_1-C_4)$alkylthio, $(C_1-C_4)$haloalkylthio, $(C_1-C_4)$alkylsulfinyl, $(C_1-C_4)$haloalkylsulfinyl, $(C_1-C_4)$alkylsulfonyl, $(C_1-C_4)$haloalkylsulfonyl, $(C_1-C_4)$alkylsulfonyloxy, $(C_1-C_4)$alkylcarbonyl, $(C_1-C_4)$haloalkylcarbonyl, aminocarbonyl, $(C_1-C_4)$alkylaminocarbonyl, di-$(C_1-C_4)$alkylaminocarbonyl, $(C_1-C_4)$alkylsulfonylamino, $(C_1-C_4)$alkylamino, di-$(C_1-C_4)$alkylamino, aminosulfonyl, $(C_1-C_4)$alkylaminosulfonyl, di-$(C_1-C_4)$alkylaminosulfonyl, NHCO—$(C_1-C_4)$alkyl ($(C_1-C_4)$alkylcarbonylamino), where only one or two of the $R^{10}$, $R^{11}$, $R^{12}$ radicals is/are a substituent other than hydrogen, Q is a heteroaromatic 9-membered or 12-membered fused bicyclic or tricyclic ring system from the group of Q1 to Q20,

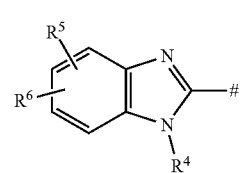

Q1

Q2 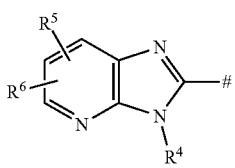

Q3 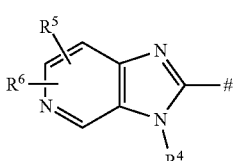

Q4 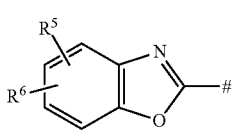

Q5 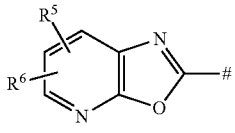

Q6 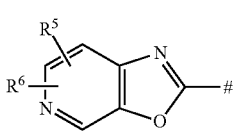

Q7 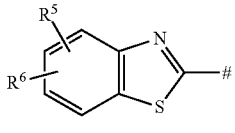

Q8 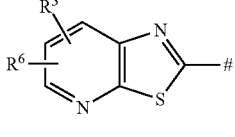

Q9 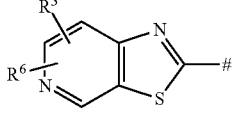

Q10 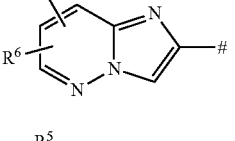

Q11 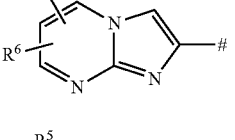

Q14 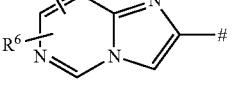

Q15 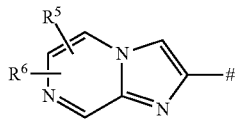

Q16 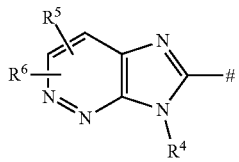

Q17 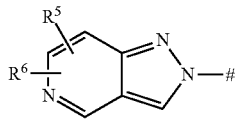

Q18 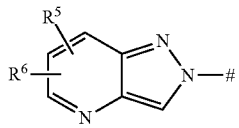

Q19 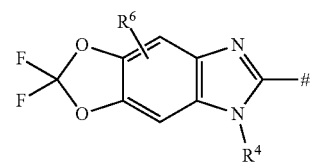

Q20 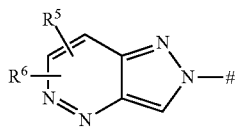

$R^4$ is $(C_1-C_4)$-alkyl, $(C_1-C_4)$-haloalkyl, $(C_1-C_4)$-cyanoalkyl, $(C_1-C_4)$-hydroxyalkyl, $(C_1-C_4)$-alkoxy-$(C_1-C_4)$-alkyl, $(C_1-C_4)$-haloalkoxy-$(C_1-C_4)$-alkyl, $(C_2-C_4)$-alkenyl, $(C_2-C_4)$-alkenyloxy-$(C_1-C_4)$-alkyl, $(C_2-C_4)$-haloalkenyloxy-$(C_1-C_4)$-alkyl, $(C_2-C_4)$-haloalkenyl, $(C_2-C_4)$-cyanoalkenyl, $(C_2-C_4)$-alkynyl, $(C_2-C_4)$-alkynyloxy-$(C_1-C_4)$-alkyl, $(C_2-C_4)$-haloalkynyl, $(C_3-C_6)$-cycloalkyl, $(C_3-C_6)$-cycloalkyl-$(C_3-C_6)$-cycloalkyl, $(C_1-C_4)$-alkyl-$(C_3-C_6)$-cycloalkyl, halo-$(C_3-C_6)$-cycloalkyl, $(C_1-C_4)$-alkylthio-$(C_1-C_4)$-alkyl, $(C_1-C_4)$-alkylsulfinyl-$(C_1-C_4)$-alkyl, $(C_1-C_4)$-alkylsulfonyl-$(C_1-C_4)$-alkyl or $(C_1-C_4)$-alkylcarbonyl-$(C_1-C_4)$-alkyl, $R^5$, $R^6$ are independently hydrogen, cyano, halogen, $(C_1-C_4)$-alkyl, $(C_1-C_4)$-haloalkyl, $(C_2-C_4)$-alkenyl, $(C_2-C_4)$-haloalkenyl, $(C_2-C_4)$-alkynyl, $(C_2-C_4)$-haloalkynyl, $(C_3-C_6)$-cycloalkyl, $(C_3-C_6)$-cycloalkyl-$(C_3-C_6)$-cycloalkyl, $(C_1-C_4)$-alkyl-$(C_3-C_6)$-cycloalkyl, $(C_1-C_4)$-alkoxy, $(C_1-C_4)$-haloalkoxy, $(C_1-C_4)$-alkoxyimino, $(C_1-C_4)$-alkylthio, $(C_1-C_4)$-haloalkylthio, $(C_1-C_4)$-alkylsulfinyl, $(C_1-C_4)$-haloalkylsulfinyl, $(C_1-C_4)$-alkylsulfonyl, $(C_1-C_4)$-haloalkylsulfonyl, $(C_1-C_4)$-alkylsulfonyloxy, $(C_1-C_4)$-alkylcarbonyl, $(C_1-C_4)$-haloalkylcarbonyl, aminocarbonyl, $(C_1-C_4)$-alkylaminocarbonyl, di-$(C_1-C_4)$-alkylaminocarbonyl, $(C_1-C_4)$-alkylsulfonylamino, $(C_1-C_4)$-alkylamino, di-$(C_1-C_4)$-alkylamino, aminosulfonyl, $(C_1-C_4)$-alkylaminosulfonyl or di-$(C_1-C_4)$-alkylaminosulfonyl, n is 0, 1 or 2.

4. Compound of formula (I) according to claim 1 in which
Aa is nitrogen or =C($R^{10}$)—,
Ab is nitrogen or =C($R^{11}$)—,
Ac is nitrogen or =C($R^{12}$)—,
Ad is nitrogen,
where not more than two of Aa, Ab, Ac and Ad can be nitrogens,
$R^1$ is methyl, ethyl, n-propyl, isopropyl, cyclopropyl, n-butyl, isobutyl, tert-butyl, cyclobutyl, fluoromethyl, difluoromethyl, trifluoromethyl, fluoroethyl, difluoroethyl, trifluoroethyl, tetrafluoroethyl or pentafluoroethyl,
$R^{10}$, $R^{11}$, $R^{12}$ are independently hydrogen, cyano, halogen, ($C_1$-$C_4$)alkyl, ($C_3$-$C_6$)cycloalkyl, aminocarbonyl, ($C_1$-$C_4$)haloalkyl, ($C_1$-$C_4$)alkoxy, ($C_1$-$C_4$)haloalkoxy, ($C_1$-$C_4$)alkylthio, ($C_1$-$C_4$)alkylsulfinyl, ($C_1$-$C_4$)alkylsulfonyl, ($C_1$-$C_4$)haloalkylthio, ($C_1$-$C_4$)haloalkylsulfinyl, ($C_1$-$C_4$)haloalkylsulfonyl or NHCO—($C_1$-$C_4$)alkyl (($C_1$-$C_4$)alkylcarbonylamino),
where only one or two of the $R^{10}$, $R^{11}$, $R^{12}$ radicals is/are a substituent other than hydrogen,
Q is a heteroaromatic 9-membered or 12-membered fused bicyclic or tricyclic ring system from the group of Q2, Q3, Q5, Q6, Q8, Q9, Q10, Q11, Q14, Q15, Q16 or Q19,

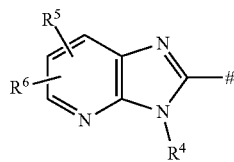

Q2

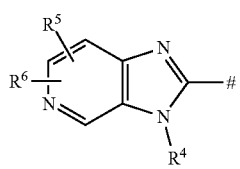

Q3

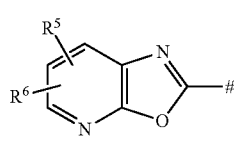

Q5

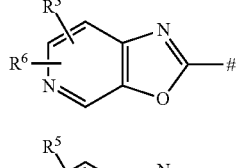

Q6

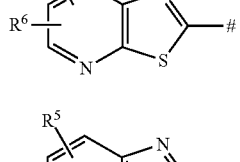

Q8

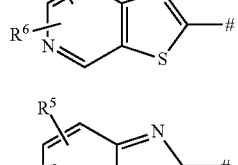

Q9

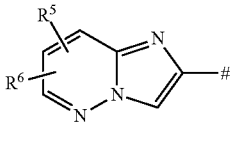

Q10

-continued

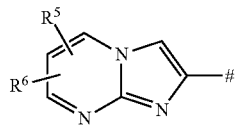

Q11

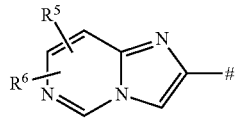

Q14

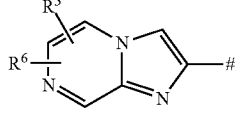

Q15

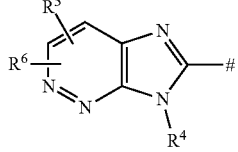

Q16

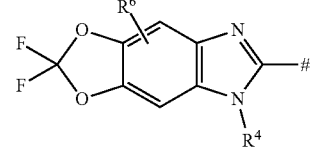

Q19

$R^4$ is ($C_1$-$C_4$)alkyl or ($C_1$-$C_4$)alkoxy-($C_1$-$C_4$)-alkyl,
$R^5$ is hydrogen, cyano, halogen, ($C_1$-$C_4$)alkyl, ($C_1$-$C_4$)haloalkyl, ($C_3$-$C_6$)cycloalkyl, ($C_3$-$C_6$)cycloalkyl-($C_3$-$C_6$)cycloalkyl, ($C_1$-$C_4$)alkyl-($C_3$-$C_6$)cycloalkyl, ($C_1$-$C_4$)alkoxy, ($C_1$-$C_4$)haloalkoxy, ($C_1$-$C_4$)alkoxyimino, ($C_1$-$C_4$)alkylthio, ($C_1$-$C_4$)haloalkylthio, ($C_1$-$C_4$)alkylsulfinyl, ($C_1$-$C_4$)haloalkylsulfinyl, ($C_1$-$C_4$)alkylsulfonyl, ($C_1$-$C_4$)haloalkylsulfonyl, ($C_1$-$C_4$)alkylcarbonyl, ($C_1$-$C_4$)haloalkylcarbonyl, ($C_1$-$C_4$)alkylaminocarbonyl, di-($C_1$-$C_4$)alkylaminocarbonyl, ($C_1$-$C_4$)alkylsulfonylamino, ($C_1$-$C_4$)alkylaminosulfonyl or di-($C_1$-$C_4$)alkylaminosulfonyl,
$R^6$ is hydrogen,
n is 0, 1 or 2.

5. Compound of formula (I) according to claim 1 in which
Aa is nitrogen or =C($R^{10}$)—,
Ab is nitrogen or =C($R^{11}$)—,
Ac is nitrogen or =C($R^{12}$)—,
Ad is nitrogen,
where not more than two of Aa, Ab, Ac and Ad can be nitrogens,
$R^1$ is methyl, ethyl, n-propyl, i-propyl or cyclopropyl,
$R^{10}$, $R^{11}$, $R^{12}$ are independently hydrogen, fluorine, chlorine, bromine, iodine, cyano, methyl, ethyl, cyclopropyl, aminocarbonyl, trifluoromethyl, trifluoromethoxy, trifluoromethylthio, trifluoromethylsulfinyl, trifluoromethylsulfonyl or methoxy,
where only one or two of the $R^{10}$, $R^{11}$, $R^{12}$ radicals is/are a substituent other than hydrogen,
Q is a heteroaromatic 9-membered fused bicyclic ring system from the group of Q2, Q3, Q10, Q14 or Q16, $R^4$ is methyl, ethyl, isopropyl, methoxymethyl or methoxyethyl, $R^5$ is fluorine, chlorine, bromine, fluoromethyl, difluoromethyl, trifluoromethyl, fluoroethyl ($CH_2CFH_2$, $CHFCH_3$), difluoroethyl ($CF_2CH_3$, $CH_2CHF_2$, $CHFCFH_2$), trifluoroethyl ($CH_2CF_3$, $CHFCHF_2$, $CF_2CFH_2$), tetrafluoroethyl ($CHFCF_3$, $CF_2CHF_2$), pentafluoroethyl, trifluoromethoxy, difluorochloromethoxy, dichlorofluoromethoxy, trifluoromethylthio, trifluoromethylsulfinyl or trifluoromethylsulfonyl, $R^6$ is hydrogen, n is 0, 1 or 2.

6. Compound of formula (I) according to claim 3 in which

Aa is $=C(R^{10})-$,

Ab is $=C(R^{11})-$,

Ac is $=C(R^{12})-$,

Ad is nitrogen or, $R^1$ is ethyl, $R^{10}$ is hydrogen or methyl, $R^{11}$ is hydrogen, chlorine, cyano, aminocarbonyl or cyclopropyl, $R^{12}$ is hydrogen or methyl, Q is a heteroaromatic 9-membered fused bicyclic ring system from the group of Q2 or Q3, $R^4$ is methyl, $R^5$ is trifluoromethyl, $R^6$ is hydrogen, n is 2.

7. Agrochemical formulation comprising a Compound of formula (I) according to claim 1 and one or more extenders and/or surfactants.

8. Agrochemical formulation according to claim 7, additionally comprising a further agrochemically active ingredient.

9. Method for controlling one or more animal pests, comprising allowing a compound of formula (I) according to claim 1 or an agrochemical formulation thereof to act on the animal pests and/or a habitat thereof.

10. A Compound of formula (I) according to claim 1 or agrochemical formulation thereof for controlling one or more animal pests.

11. The compound of formula (I) according to claim 6, wherein $R^{10}$ is hydrogen, $R^{11}$ is hydrogen, $R^{12}$ is hydrogen, and Q is Q3.

12. The compound of formula (I) according to claim 6, wherein $R^{10}$ is methyl, $R^{11}$ is hydrogen, $R^{12}$ is methyl, and Q is Q3.

13. The compound of formula (I) according to claim 6, wherein $R^{10}$ is methyl, $R^{11}$ is hydrogen, $R^{12}$ is methyl, and Q is Q2.

14. The compound of formula (I) according to claim 6, wherein $R^{10}$ is hydrogen, $R^{11}$ is hydrogen, $R^{12}$ is hydrogen, and Q is Q2.

* * * * *